(12) United States Patent
Martel et al.

(10) Patent No.: US 10,329,307 B2
(45) Date of Patent: Jun. 25, 2019

(54) HETEROCYCLIC COMPOUNDS AS INHIBITORS OF PLATELET AGGREGATION

(71) Applicant: UNIVERSITE DE MONTREAL, Montreal, Quebec (CA)

(72) Inventors: Alain Martel, Montreal (CA); Francois Tremblay, Montreal (CA)

(73) Assignee: Universite de Montreal, Montreal, QC (CA)

( * ) Notice: Subject to any disclaimer, the term of this patent is extended or adjusted under 35 U.S.C. 154(b) by 0 days.

(21) Appl. No.: 15/767,795

(22) PCT Filed: Sep. 19, 2016

(86) PCT No.: PCT/CA2016/000237
§ 371 (c)(1),
(2) Date: Apr. 12, 2018

(87) PCT Pub. No.: WO2017/066863
PCT Pub. Date: Apr. 27, 2017

(65) Prior Publication Data
US 2018/0298030 A1  Oct. 18, 2018

Related U.S. Application Data

(60) Provisional application No. 62/243,224, filed on Oct. 19, 2015.

(51) Int. Cl.
| | | |
|---|---|---|
| C07D 513/04 | (2006.01) |
| C07D 487/04 | (2006.01) |
| C07D 498/04 | (2006.01) |
| A61P 7/02 | (2006.01) |
| A61K 31/433 | (2006.01) |
| A61K 31/454 | (2006.01) |
| A61K 31/4545 | (2006.01) |
| A61K 31/496 | (2006.01) |

(52) U.S. Cl.
CPC .......... C07D 513/04 (2013.01); A61K 31/433 (2013.01); A61K 31/454 (2013.01); A61K 31/4545 (2013.01); A61K 31/496 (2013.01); A61P 7/02 (2018.01); C07D 487/04 (2013.01); C07D 498/04 (2013.01)

(58) Field of Classification Search
CPC .. C07D 513/04; C07D 487/04; C07D 498/04; A61P 7/02
USPC ........................................................ 514/248
See application file for complete search history.

(56) References Cited

FOREIGN PATENT DOCUMENTS

| WO | 2013163241 A1 | 10/2013 |
| WO | 2013163244 A1 | 10/2013 |
| WO | 2013163279 A1 | 10/2013 |
| WO | 2016134450 A1 | 9/2016 |

*Primary Examiner* — Kristin A Vajda
(74) *Attorney, Agent, or Firm* — Hoffmann & Baron, LLP

(57) ABSTRACT

The present invention provides compounds of Formula I: wherein Y, AA, W, $R^{3'}$ $R^2$, $R^4$, $R^5$, $R^6$, $R^7$, $X^1$, $X^2$, $X^3$, $X^4$ and $X^5$ are as defined herein, or a stereoisomer, tautomer, pharmaceutically acceptable salt, prodrug or esters or solvate form thereof, wherein all of the variables are as defined herein. These compounds are inhibitors of platelet aggregation and thus can be used as medicaments for treating or preventing thromboembolic disorders.

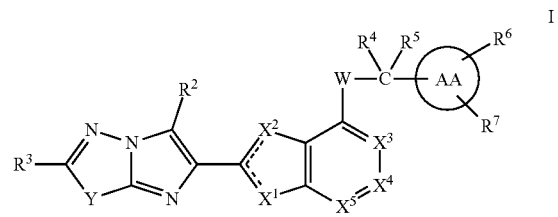

19 Claims, No Drawings

HETEROCYCLIC COMPOUNDS AS INHIBITORS OF PLATELET AGGREGATION

CROSS-REFERENCE TO RELATED APPLICATION

This application is the U.S. National Phase of, and Applicant claims priority from, International Patent Application No. PCT/CA2016/000237, filed on Sep. 19, 2016, and also claims priority to U.S. Provisional Application No. 62/243,224, filed on Oct. 19, 2015, each of which is incorporated herein by reference in their entirety.

FIELD OF THE INVENTION

The present invention provides novel heterocyclic compounds and analogues thereof, which are inhibitors of platelet aggregation and which are useful in preventing or treating thromboembolic disorders. This invention also relates to pharmaceutical compositions containing these compounds and methods of using the same.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S. R., *Nature*, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4. Inhibitors of PAR1 have been investigated extensively, and several compounds, including vorapaxar (now marketed as ZONTIVITY® by Merck & Co.) and atopaxar have advanced into late stage clinical trials. Recently, in the TRACER phase III trial in ACS patients, vorapaxar did not significantly reduce cardiovascular events, but significantly increased the risk of major bleeding (Tricoci, P. et al., *N. Eng. J. Med.*, 366(1):20-33 (2012). Thus, there remains a need to discover new antiplatelet agents with increased efficacy and reduced bleeding side effects.

There are several early reports of preclinical studies of PAR4 inhibitors. Lee, F-Y. et al., "Synthesis of 1-Benzyl-3-(5'-hydroxymethyl-2'-furyl)indazole Analogues as Novel Antiplatelet Agents", *J. Med. Chem.*, 44(22):3746-3749 (2001) discloses in the abstract that the compound

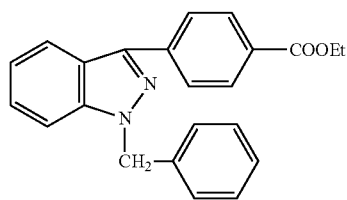

"was found to be a selective and potent inhibitor or protease-activated receptor type 4 (PAR4)-dependent platelet activation."

Compound 58 is also referred to as YD-3 in Wu, C-C. et al., "Selective Inhibition of Protease-activated Receptor 4-dependent Platelet Activation by YD-3", *Thromb. Haemost.*, 87:1026-1033 (2002). Also, see Chen, H. S. et al., "Synthesis and platelet activity", *J. Bioorg. Med. Chem.*, 16:1262-1278 (2008).

EP1166785 A1 and EP0667345 disclose various pyrazole derivatives which are useful as inhibitors of platelet aggregation.

The PCT publications WO2013/163279, WO2013/163244 and WO2013/163241 disclose various PAR4 antagonists which are useful as inhibitors of platelet aggregation.

SUMMARY OF THE INVENTION

It has been found that compounds of Formula (I) in accordance with the present invention are PAR4 antagonists which inhibit platelet aggregation in gamma-thrombin induced platelet aggregation assays.

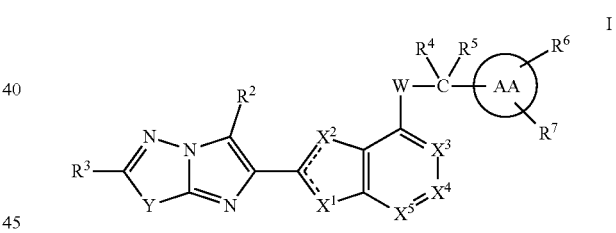

wherein the various moieties are as defined herein.

Accordingly, it has been found that compounds of Formula (I) are PAR4 antagonists which inhibit platelet aggregation in gamma-thrombin induced platelet aggregation assays. Moreover, a compound(s) of the present invention has been shown to inhibit platelet aggregation in an alpha-thrombin induced platelet aggregation assay.

Accordingly, the present invention provides novel compounds, and analogues thereof, which are PAR4 antagonists and are useful as selective inhibitors of platelet aggregation, including stereoisomers, tautomers, pharmaceutically acceptable salts, solvates, or prodrug or esters thereof.

The present invention also provides processes and intermediates for making the compounds of the present invention or stereoisomers, tautomers, pharmaceutically acceptable salts, solvates, or prodrug or esters thereof.

The present invention also provides pharmaceutical compositions comprising a pharmaceutically acceptable carrier and at least one of the compounds of the present invention or stereoisomers, tautomers, pharmaceutically acceptable salts, solvates, or prodrug or esters thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrug or esters thereof.

The present invention also provides the compounds of the present invention or stereoisomers, tautomers, pharmaceutically acceptable salts, solvates, or prodrug or esters thereof, for use in therapy.

The present invention also provides the use of the compounds of the present invention or stereoisomers, tautomers, pharmaceutically acceptable salts, solvates, or prodrug or esters thereof, for the manufacture of a medicament for the treatment or prophylaxis of a thromboembolic disorder.

Other features and advantages of the invention will be apparent from the following detailed description and claims.

DETAILED DESCRIPTION

In one embodiment, the present invention provides compounds, stereoisomers, tautomers, salts, solvates or prodrugs thereof, of Formula I having the structure:

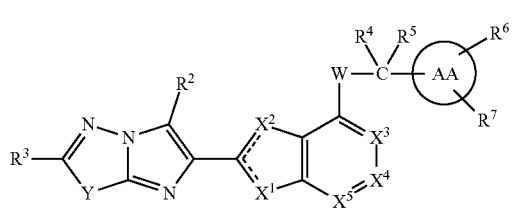

or a stereoisomer, tautomer, pharmaceutically acceptable salt, solvate or prodrug thereof, wherein:

the dashed lines represent double-bonds with the proviso that only one of the two dashed line double bonds exists at the same time;

$X^1$ is O and $X^2$ is =N— or $CR^{1a}$; or
$X^2$ is S and $X^1$ is =N— or $CR^{1a}$; or
$X^1$ is =N— and $X^2$ is O or $NR^{1b}$; or
$X^1$ is $NR^{1b}$ and $X^2$ is $CR^{1a}$; or
$X^1$ is $CR^{1a}$ and $X^2$ is $NR^{1b}$;

$X^3$, $X^4$, and $X^5$ are independently selected from $CR^{1d}$ and =N—;

$R^{1a}$ is selected from the group consisting of H, halo, cyano, $C_1$-$C_3$ alkyl, $C_3$-$C_5$ cycloalkyl, halo-$C_1$-$C_2$alkyl, and $C_1$-$C_3$ alkoxy;

$R^{1b}$ is selected from the group consisting of H, $C_1$-$C_3$ alkyl, $C_3$-$C_5$ cycloalkyl, and halo-$C_1$-$C_2$alkyl;

$R^{1d}$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $OCHF_2$, $OCH_2F$, $C_1$-$C_2$-alkoxy-$C_1$-$C_2$-alkoxy, halo-$C_1$-$C_3$-alkyl, halo-$C_{1-2}$-alkoxy, halo-$C_{1-2}$-alkylthio, benzyloxy substituted (on the phenyl of said benzyl) by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, and —(CH_2)_n-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;

n is 1 or 2;

Y is S, O or —$CR^{1e}$=$CR^{1f}$—;

$R^{1e}$ is independently at each occurrence selected from the group consisting of H, halo, cyano, $C_1$-$C_3$ alkyl, $C_3$-$C_5$ cycloalkyl, halo-$C_1$-$C_2$ alkyl, $C_1$-$C_3$ alkoxy, and halo-$C_1$-$C_3$ alkoxy;

$R^{1f}$ is independently at each occurrence selected from the group consisting of H, halo, cyano, $C_1$-$C_3$ alkyl, $C_3$-$C_5$ cycloalkyl, halo-$C_1$-$C_2$ alkyl, $C_1$-$C_3$ alkoxy, and halo-$C_1$-$C_3$ alkoxy;

$R^2$ is H, halo, $C_1$-$C_3$ alkyl, halo-$C_1$-$C_2$ alkyl, $C_1$-$C_3$ alkoxy, halo-$C_1$-$C_3$ alkoxy, or $C_3$-$C_5$ cycloalkyl;

$R^3$ is selected from the group consisting of $C_{1-4}$ alkyl, $C_{1-4}$ alkoxy, $C_{1-4}$ alkylthio, $C_{1-2}$ haloalkyl, $C_{1-2}$ haloalkoxy, $C_{1-2}$ haloalkylthio, $C_{3-4}$ cycloalkyl, halo-$C_{3-4}$ cycloalkyl, $C_{1-4}$ alkylamino, di-$C_{1-4}$ alkylamino, ($C_{1-2}$ alkoxy) $C_{1-2}$ alkyl, halo($C_{1-2}$ alkoxy) $C_{1-2}$ alkyl, $C_{2-3}$ alkenyl, $C_{2-3}$ alkynyl, tetrahydrofuran-2-yl, and halo;

W is O or S;

$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;

(AA)

is a 4-8 membered saturated heterocyclic ring containing 1-3 ring atoms which may be the same or different, each being independently selected from the group consisting of N, O and S, wherein said ring (AA)

may be optionally fused to a $C_6$-$C_{10}$ aryl or a 5-6 membered heteroaryl ring, further wherein said ring AA and optional fused ring may be unsubstituted or independently substituted with 0-1 $R^6$, 0-4 $R^7$ or both 0-1 $R^6$ and 0-4 $R^7$ substituents;

$R^6$ is selected from the group consisting of $C_6$-$C_{10}$ aryl, 5-10 membered heteroaryl, 4-8 membered saturated heterocyclic ring, or $C_3$-$C_8$ cycloalkyl ring, wherein each of said $C_6$-$C_{10}$ aryl, 5-10 membered heteroaryl, 4-8 membered saturated heterocyclic ring, or $C_3$-$C_8$ cycloalkyl ring, can be substituted with 0-4 $R^{7a}$ substituents;

$R^7$ is independently selected at each occurrence from the group consisting of halo, $C_1$-$C_4$ alkyl, $C_1$-$C_4$ alkoxy, halo $C_1$-$C_4$ alkyl, halo $C_1$-$C_4$ alkoxy, $C_1$-$C_4$ alkylthio, halo $C_1$-$C_4$ alkylthio, hydroxy, hydroxy $C_1$-$C_4$ alkyl, hydroxy $C_1$-$C_4$ alkoxy, ($C_1$-$C_6$ alkyl)carboxy-carboxy, —C(O)Oalkyl, —C(O)NH_2, —C(O)NHalkyl, —C(O)N-dialkyl, —NH_2, (alkyl)amino-, (dialkyl)amino-, —NH-carboxy-$C_1$-$C_6$ alkyl, nitro, cyano, oxo, (haloaryl)alkyl-, $C_3$-$C_6$ cycloalkyl, —S(O)-alkyl, —S(O)-aryl, —S(O)-heteroaryl, —S(O_2) alkyl, —S(O_2)aryl, —S(O_2)heteroaryl, —S(O_2)NH_2, —S(O_2)NHalkyl, —S(O_2)N-dialkyl, or if two $R^7$ substituents are attached to the same carbon atom, they may be taken together with the carbon atom to which they are attached to form a $C_3$-$C_6$ cycloalkyl group or a 3-6 membered heterocyclic ring, or if two $R^7$ substituents are attached to adjacent carbon atoms, they may be taken together with the carbon atoms to which they are attached to form a $C_3$-$C_6$ cycloalkyl group or a 3-6 membered heterocyclic ring; and $R^{7a}$ is independently selected at each occurrence from the group consisting of halo, $C_1$-$C_4$ alkyl, $C_1$-$C_4$ alkoxy, halo $C_1$-$C_4$ alkyl, halo $C_1$-$C_4$ alkoxy, $C_1$-$C_4$ alkylthio, halo $C_1$-$C_4$ alkylthio, hydroxy, hydroxy $C_1$-$C_4$ alkyl, hydroxy $C_1$-$C_4$ alkoxy, ($C_1$-$C_6$ alkyl)carboxy-, carboxy, —C(O)Oalkyl, —C(O)NH$_2$, —C(O)NHalkyl, —C(O)N-dialkyl, —NH$_2$, (alkyl)amino-, (dialkyl)amino-, —NHC(O)O—$C_1$-$C_6$ alkyl, —NHC(O)-halo $C_1$-$C_6$ alkyl, nitro, cyano, oxo, $C_3$-$C_6$ cycloalkyl, —S(O)-alkyl, —S(O)-aryl, —S(O)-heteroaryl, —S(O$_2$)alkyl, —S(O$_2$)aryl, —S(O$_2$)heteroaryl, —S(O$_2$)NH$_2$, —S(O$_2$)NHalkyl, —S(O$_2$)N-dialkyl, aryl $C_1$-$C_4$ alkoxy, —C(O)aryl, —C(O)—$C_1$-$C_6$ alkyl, or if two $R^{7a}$ substituents are attached to the same carbon atom, they may be taken together with the carbon atom to which they are attached to form a C3-C6 cycloalkyl group or a 3-6 membered heterocyclic ring, or if two $R^{7a}$ substituents are attached to adjacent carbon atoms, they may be taken together with the carbon atoms to which they are attached to form a $C_3$-$C_6$ cycloalkyl group or a 3-6 membered heterocyclic ring.

It should be understood that the term "

is selected from the group consisting of a 4-8 membered saturated heterocyclic ring containing 1-3 ring atoms which may be the same or different each being independently selected from the group consisting of N, O and S" means that the ring does not contain two adjacent oxygen atoms or sulfur atoms.

The present invention is further described by various embodiments described herein. It is understood that any and all embodiments of the present invention may be independently selected and taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

In an embodiment, $X^2$ is S and $X^1$ is =N—.
In an embodiment, $X^2$ is S and $X^1$ is —CR$^{1a}$.
In an embodiment, $X^2$ is O and $X^1$ is =N—.
In an embodiment, $X^2$ is NR$^{1b}$ and $X^1$ is =N—.
In an embodiment, $X^2$ is NR$^{1b}$ and $X^1$ is —CR$^{1a}$.
In an embodiment, $X^2$ is CR$^a$ and $X^1$ is NR$^{1b}$.
In an embodiment, $X^2$ is =N— and $X^1$ is O.
In an embodiment, $X^2$ is CR$^{1a}$ and $X^1$ is O.
In an embodiment R$^{1a}$ is H.
In an embodiment R$^{1b}$ is H.
In an embodiment, $X^3$, $X^4$, and $X^5$ are all CR$^{1d}$.
In an embodiment, $X^3$ is N, and $X^4$ and $X^5$ are CR$^{1d}$.
In an embodiment, $X^4$ is N, and $X^3$ and $X^5$ are CR$^{1d}$.
In an embodiment, $X^5$ is N, and $X^3$ and $X^4$ are CR$^d$.
In an embodiment, Y is S.
In an embodiment, Y is —(CH=CH)—.
In an embodiment, Y is O.
In an embodiment, W is O.
In an embodiment, W is S.
In an embodiment, Y is S and W is O.
In an embodiment, Y is —(CH=CH)— and W is O.
In an embodiment, $R^2$ is H.

In an embodiment, $R^2$ is halo.
In an embodiment, $R^2$ is methyl.
In an embodiment, $R^3$ is alkyl, alkoxy, alkylthio or haloalkyl.
In an embodiment, $R^3$ is methyl, ethyl, methoxy, methylthio, 1-fluoroethyl or 1,1-difluoroethyl.
In an embodiment, $R^4$ is H or methyl.
In an embodiment, $R^5$ is H or methyl.
In an embodiment, both $R^4$ and $R^5$ are H.
In an embodiment, ring

is a 4-8 membered saturated heterocyclic ring containing 1-3 ring atoms which may be the same or different each being independently selected from the group consisting of N, O and S, wherein said saturated heterocyclic ring is unsubstituted.

In an embodiment, ring

is a 4-8 membered saturated heterocyclic ring containing 1-3 ring atoms which may be the same or different each being independently selected from the group consisting of N, O and S, wherein said saturated heterocyclic ring is fused to a $C_6$-$C_{10}$ aryl or a 5-6 membered heteroaryl ring, wherein said ring AA and fused ring may be unsubstituted or independently substituted with 0-1 $R^6$, 0-4 $R^7$ substituents or both 0-1 $R^6$ and 0-4 $R^7$ substituents.

In an embodiment, ring

is a 4-8 membered saturated heterocyclic ring containing 1-3 ring atoms which may be the same or different each being independently selected from the group consisting of N, O and S, wherein said saturated heterocyclic ring is optionally fused to a 5-6 membered heteroaryl wherein said ring AA and optional fused ring is unsubstituted or optionally substituted with an $R^6$ substituent and 0-4 $R^7$ substituents.

In an embodiment, ring

is a 4-8 membered saturated heterocyclic ring containing 1-3 ring atoms which may be the same or different each being independently selected from the group consisting of N, O and S, wherein said saturated heterocyclic ring is optionally fused to a 5-6 membered heteroaryl wherein said ring AA and optional fused ring is unsubstituted or optionally substituted with 1-4 $R^7$ substituents.

In an embodiment, $R^6$ is a $C_6$-$C_{10}$ aryl.
In an embodiment, $R^6$ is a 5-10 membered heteroaryl.

In an embodiment, $R^6$ is a 4-8 membered saturated heterocyclic ring.

In an embodiment, $R^6$ is a $C_3$-$C_8$ cycloalkyl ring.

In an embodiment, $R^7$ is halo.

In an embodiment, $R^7$ is alkyl, alkoxy, haloalkyl, haloalkoxy, alkylthio, hydroxy, (haloaryl)alkyl-, hydroxyalkyl or hydroxyalkoxy.

In an embodiment, $R^{7a}$ is halo, alkyl, alkoxy, haloalkyl, haloalkoxy, alkylthio, haloalkylthio, hydroxy, hydroxyalkyl or hydroxyalkoxy.

In an embodiment, ring

is a pyrrolidine ring which may be unsubstituted or substituted with 0-1 $R^6$ and 0-4 $R^7$ substituents.

In an embodiment, ring

is a piperidine ring which may be unsubstituted or substituted with 0-1 $R^6$ and 0-4 $R^7$ substituents.

In an embodiment, ring

is a piperazine ring which may be unsubstituted or substituted with 0-1 $R^6$ and 0-4 $R^7$ substituents.

In an embodiment, ring

is a morpholine ring which may be unsubstituted or substituted with 0-1 $R^6$ and 0-4 $R^7$ substituents.

In an embodiment, ring

is a thiomorpholine ring which may be unsubstituted or substituted with 0-1 $R^6$ and 0-4 $R^7$ substituents.

In an embodiment, ring

is an azetidine ring which may be unsubstituted or substituted with 0-1 $R^6$ and 0-4 $R^7$ substituents.

In an embodiment, ring

is a pyrrolidine ring which may be unsubstituted or substituted with one $R^6$ and 0-4 $R^7$ substituents.

In an embodiment, ring

is a piperidine ring which may be unsubstituted or substituted with one $R^6$ and 0-4 $R^7$ substituents.

In an embodiment, ring

is a piperazine ring which may be unsubstituted or substituted one $R^6$ and 0-4 $R^7$ substituents.

In an embodiment, ring

is a morpholine ring which may be unsubstituted or substituted with one $R^6$ and 0-4 $R^7$ substituents.

In an embodiment, ring

is a thiomorpholine ring which may be unsubstituted or substituted with one $R^6$ and 0-4 $R^7$ substituents.

In an embodiment, ring

is an azetidine ring which may be unsubstituted or substituted with one $R^6$ and 0-4 $R^7$ substituents.

In an embodiment, ring

is a pyrrolidine ring which may be unsubstituted or substituted with 0-1 $R^6$ and 1-4 $R^7$ substituents.

In an embodiment, ring

is a piperidine ring which may be unsubstituted or substituted with 0-1 R⁶ and 1-4 R⁷ substituents.

In an embodiment, ring

is a piperazine ring which may be unsubstituted or substituted with 0-1 R⁶ and 1-4 R⁷ substituents.

In an embodiment, ring

is a morpholine ring which may be unsubstituted or substituted with 0-1 R⁶ and 1-4 R⁷ substituents.

In an embodiment, ring

is a thiomorpholine ring which may be unsubstituted or substituted with 0-1 R⁶ and 1-4 R⁷ substituents.

In an embodiment, ring

is an azetidine ring which may be unsubstituted or substituted with 0-1 R⁶ and 1-4 R⁷ substituents.

In an embodiment, ring

is a pyrrolidine ring which may be unsubstituted or substituted with 1-4 R⁷ substituents.

In an embodiment, ring

is a piperidine ring which may be unsubstituted or substituted with 1-4 R⁷ substituents.

In an embodiment, ring

is a piperazine ring which may be unsubstituted or substituted with 1-4 R⁷ substituents.

In an embodiment, ring

is a morpholine ring which may be unsubstituted or substituted with 1-4 R⁷ substituents.

In an embodiment, ring

is a thiomorpholine ring which may be unsubstituted or substituted with 1-4 R⁷ substituents.

In an embodiment, ring

is an azetidine ring which may be unsubstituted or substituted with 1-4 R⁷ substituents.

In an embodiment, illustrative examples of the compound of Formula I are the compounds of the following formulae:

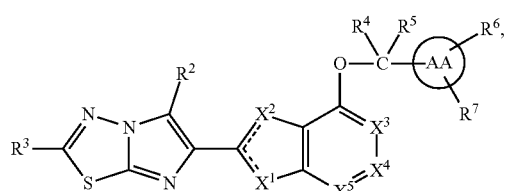

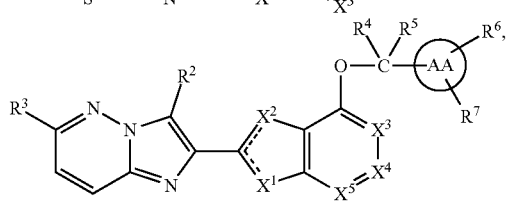

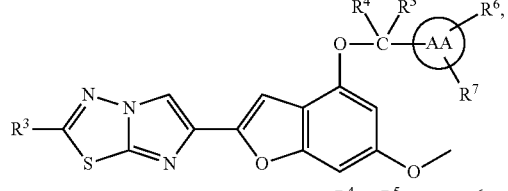

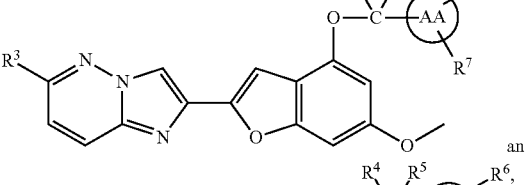

and

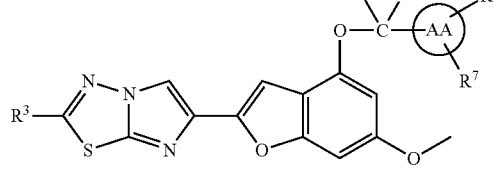

wherein the various moieties, as needed, are selected from the definitions described for Formula I.

In an embodiment, the compound I has the formula IA:

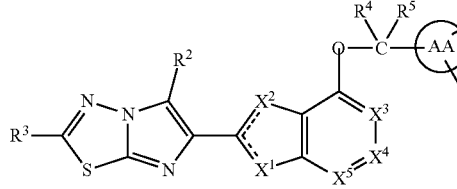

IA or a stereoisomer, tautomer, pharmaceutically acceptable salt, solvate or prodrug thereof, wherein:
the dashed lines represent double-bonds with the proviso that only one of the two dashed line double bonds exists at the same time;
$X^1$ is O and $X^2$ is =N— or $CR^{1a}$; or
$X^2$ is S and $X^1$ is =N—; or
$X^1$ is =N— and $X^2$ is O;
$X^3$, $X^4$, and $X^5$ are independently selected from $CR^{1d}$ and N;
$R^{1a}$ if present, is H or Me;
$R^{1d}$ is selected from the group consisting of $C_1$-$C_4$ alkoxy, halo, CN, $OCF_3$, $OCHF_2$, $OCH_2F$, halo-$C_1$-$C_3$-alkyl, or halo-$C_{1-2}$-alkoxy;
$R^2$ is H or Me;
$R^3$ is selected from the group consisting of $C_{1-4}$ alkyl, $C_{1-4}$ alkoxy, $C_{1-4}$ alkylthio, $C_{1-2}$ haloalkyl, $C_{1-2}$ haloalkoxy, $C_{1-2}$ haloalkylthio, $C_{3-4}$ cycloalkyl, halo-$C_{3-4}$ cycloalkyl; and
$R^4$ and $R^5$ are independently selected from H, $C_1$-$C_6$ alkyl, and $C_1$-$C_4$ fluoroalkyl.

In an embodiment, the compound I has the formula IB:

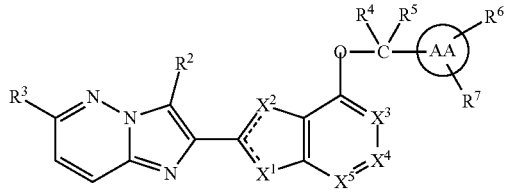

IB or a stereoisomer, tautomer, pharmaceutically acceptable salt, solvate or prodrug thereof, wherein:
the dashed lines represent double-bonds with the proviso that only one of the two dashed line double bonds exists at the same time;
$X^1$ is O and $X^2$ is =N— or $CR^1$a; or
$X^2$ is S and $X^1$ is =N—; or
$X^1$ is =N— and $X^2$ is O;
$X^3$, $X^4$, and $X^5$ are independently selected from $CR^{1d}$ and N;
$R^{1a}$ if present, is H or Me;
$R^{1d}$ is selected from the group consisting of $C_1$-$C_4$ alkoxy, halo, CN, $OCF_3$, $OCHF_2$, $OCH_2F$, halo-$C_1$-$C_3$-alkyl, or halo-$C_{1-2}$-alkoxy;
$R^2$ is H or Me;
$R^3$ is selected from the group consisting of $C_{1-4}$ alkyl, $C_{1-4}$ alkoxy, $C_{1-4}$ alkylthio, $C_{1-2}$ haloalkyl, $C_{1-2}$ haloalkoxy, $C_{1-2}$ haloalkylthio, $C_{3-4}$ cycloalkyl, halo-$C_{3-4}$ cycloalkyl; and
$R^4$ and $R^5$ are independently selected from H, $C_1$-$C_6$ alkyl, and $C_1$-$C_4$ fluoroalkyl.

In an embodiment, the compound I has the formula IC:

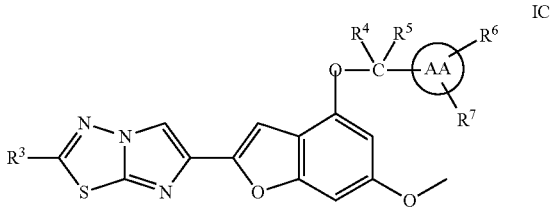

IC or a stereoisomer, tautomer, pharmaceutically acceptable salt, solvate or prodrug thereof, wherein:
$R^3$ is selected from the group consisting of methyl, ethyl, methoxy, fluoroethyl, and difluoroethyl; and
$R^4$ and $R^5$ are independently selected from H, and methyl.

is a piperidine, piperazine, morpholine, or pyrrolidine ring which may be unsubstituted or substituted at any open carbon atom valence with 0-1 $R^6$ and 0-4 $R^7$ substituents.

In an embodiment, the compound I has the formula ID:

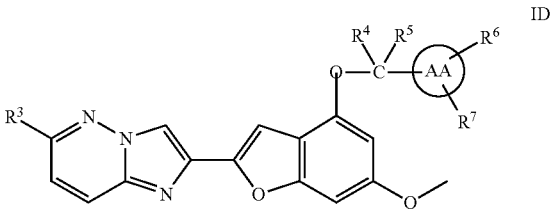

ID or a stereoisomer, tautomer, pharmaceutically acceptable salt, solvate or prodrug thereof, wherein:
$R^3$ is selected from the group consisting of methyl, ethyl, and chloro;
$R^4$ and $R^5$ are independently selected from H, and methyl; and

is a piperidine, piperazine, morpholine, or pyrrolidine ring which may be unsubstituted or substituted at any open carbon atom valence with 0-1 $R^6$ and 0-4 $R^7$ substituents.

In an embodiment, the compound I has the formula IE:

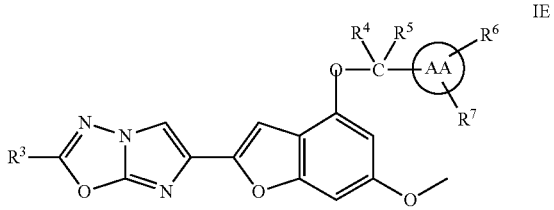

IE or a stereoisomer, tautomer, pharmaceutically acceptable salt, solvate or prodrug thereof, wherein:

the dashed lines represent double-bonds with the proviso that only one of the two dashed line double bonds exists at the same time;

$X^1$ is O and $X^2$ is =N— or $CR^{1a}$; or $X^2$ is S and $X^1$ is =N—; or $X^1$ is =N— and $X^2$ is O;

$X^3$, $X^4$, and $X^5$ are independently selected from $CR^{1d}$ and N;

$R^{1a}$ if present, is H or Me;

$R^{1d}$ is selected from the group consisting of $C_1$-$C_4$ alkoxy, halo, CN, $OCF_3$, $OCHF_2$, $OCH_2F$, halo-$C_1$-$C_3$-alkyl, or halo-$C_{1-2}$-alkoxy;

$R^2$ is H or Me;

$R^3$ is selected from the group consisting of $C_{1-4}$ alkyl, $C_{1-4}$ alkoxy, $C_{1-4}$ alkylthio, $C_{1-2}$ haloalkyl, $C_{1-2}$ haloalkoxy, $C_{1-2}$ haloalkylthio, $C_{3-4}$ cycloalkyl, halo-$C_{3-4}$ cycloalkyl; and $R^4$ and $R^5$ are independently selected from H, $C_1$-$C_6$ alkyl, and $C_1$-$C_4$ fluoroalkyl.

In an embodiment, any substitution on ring

is attached to the ring via a ring nitrogen on said substitution.

In an embodiment, any substitution on ring

is attached to the ring via a ring carbon on said substitution.

In an embodiment, the moiety

is attached to the ring

via a nitrogen atom on said ring

.

In an embodiment, the moiety

is attached to the ring

via a carbon atom on said ring

.

In an embodiment, any substitution on ring

is attached to the ring via any ring nitrogen on said substitution and a nitrogen on said ring.

In an embodiment, any substitution on ring

is attached to the ring via any ring carbon on said substitution and a carbon on said ring.

In an embodiment, any substitution on ring is attached to the ring via any ring nitrogen on said substitution and a carbon on said ring.

In an embodiment, any substitution on ring is attached to the ring via any carbon on said substitution and a nitrogen on said ring.

In one embodiment, the present invention provides compounds, stereoisomers, tautomers, salts, solvates or prodrugs thereof, wherein the compounds are compounds of Formula I.

In one embodiment, the present invention provides compounds, stereoisomers, tautomers, salts, solvates or prodrugs thereof, wherein the compounds are compounds of Formula IA.

In one embodiment, the present invention provides compounds, stereoisomers, tautomers, salts, solvates or prodrugs thereof, wherein the compounds are compounds of Formula IB.

In one embodiment, the present invention provides compounds, stereoisomers, tautomers, salts, solvates or prodrugs thereof, wherein the compounds are compounds of Formula IC.

In one embodiment, the present invention provides compounds, stereoisomers, tautomers, salts, solvates or prodrugs thereof, wherein the compounds are compounds of Formula ID.

In one embodiment, the present invention provides compounds, stereoisomers, tautomers, salts, solvates or prodrugs thereof, wherein the compounds are compounds of Formula IE.
In still yet another embodiment, the present invention provides compounds, stereoisomers, tautomers, salts, solvates, or prodrugs thereof, wherein the compounds are selected from:
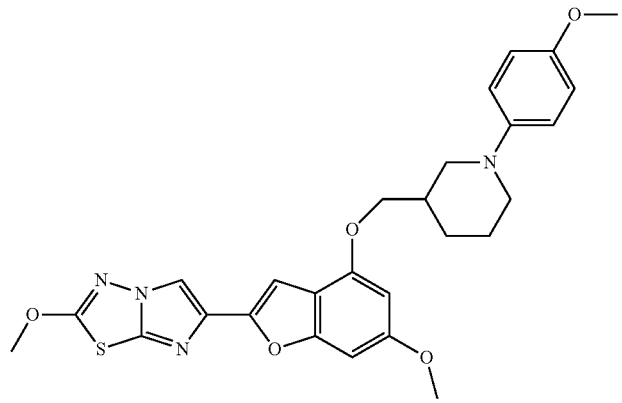
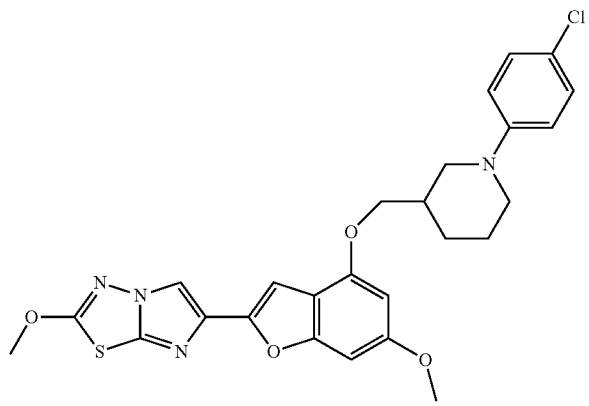
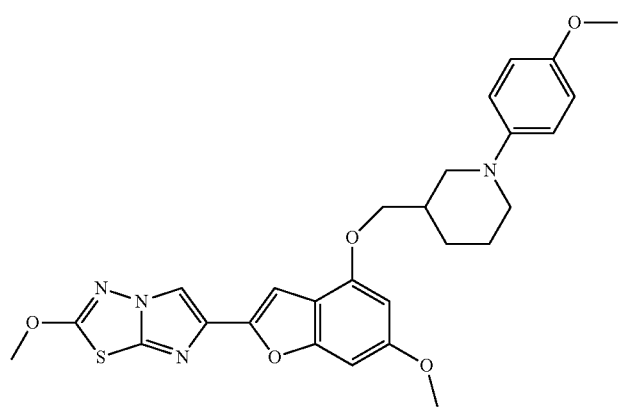
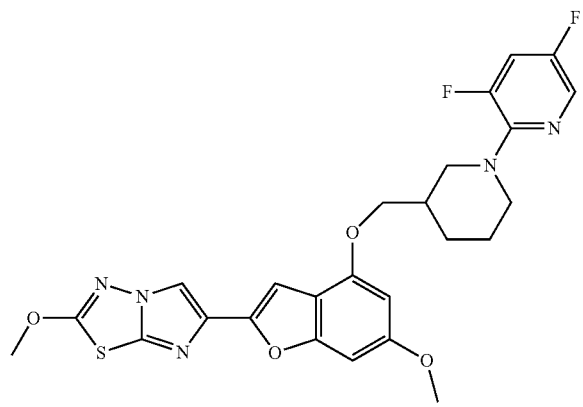
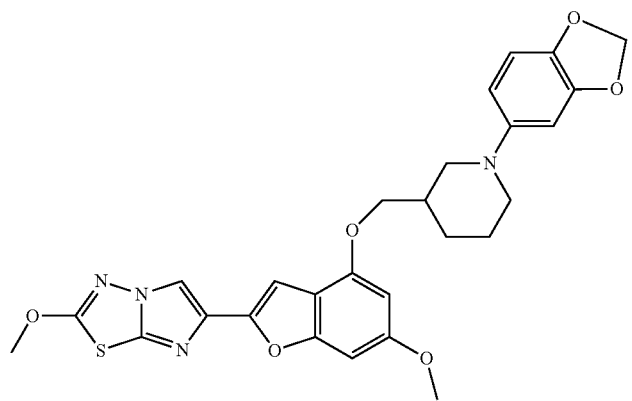

-continued
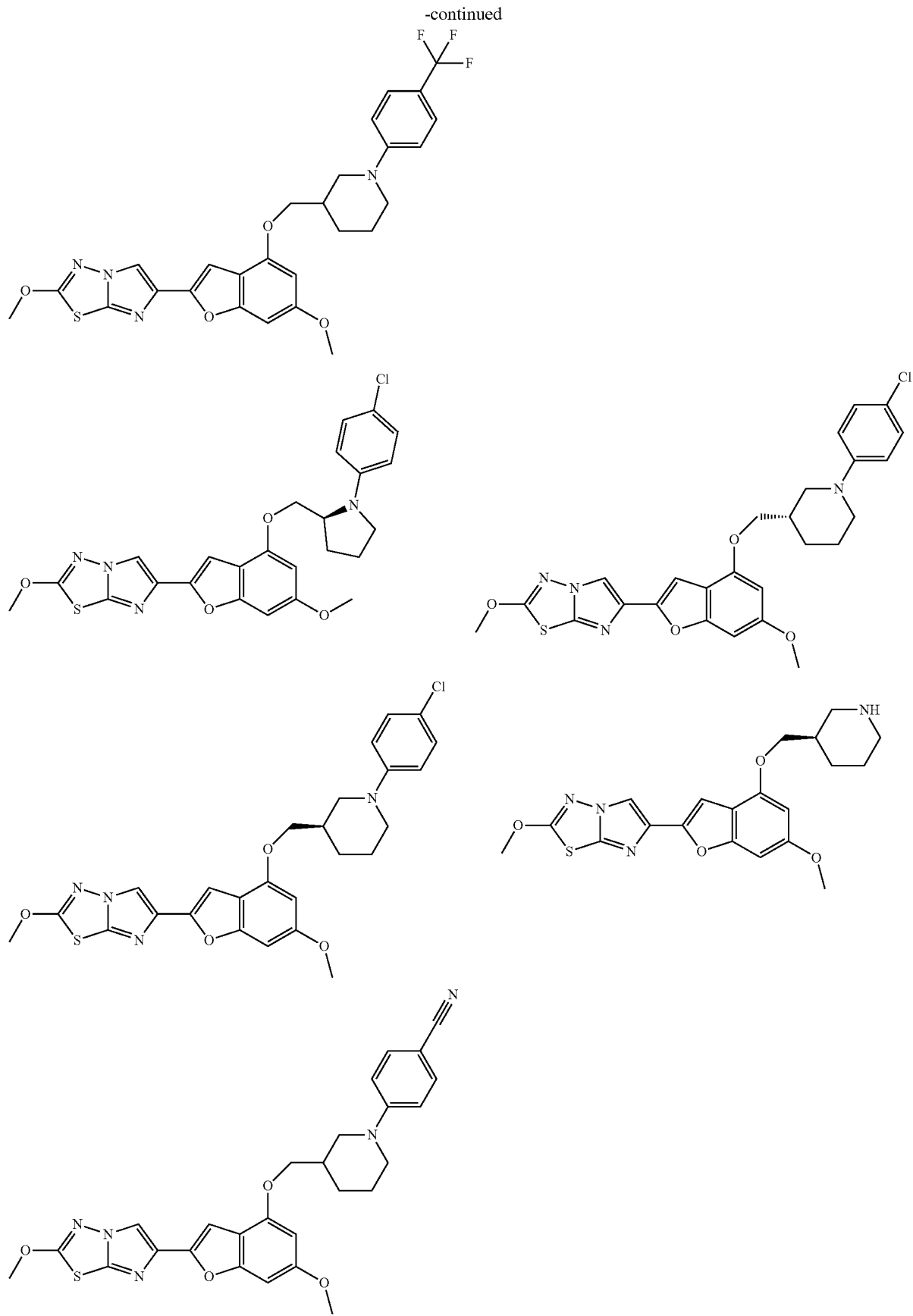

-continued
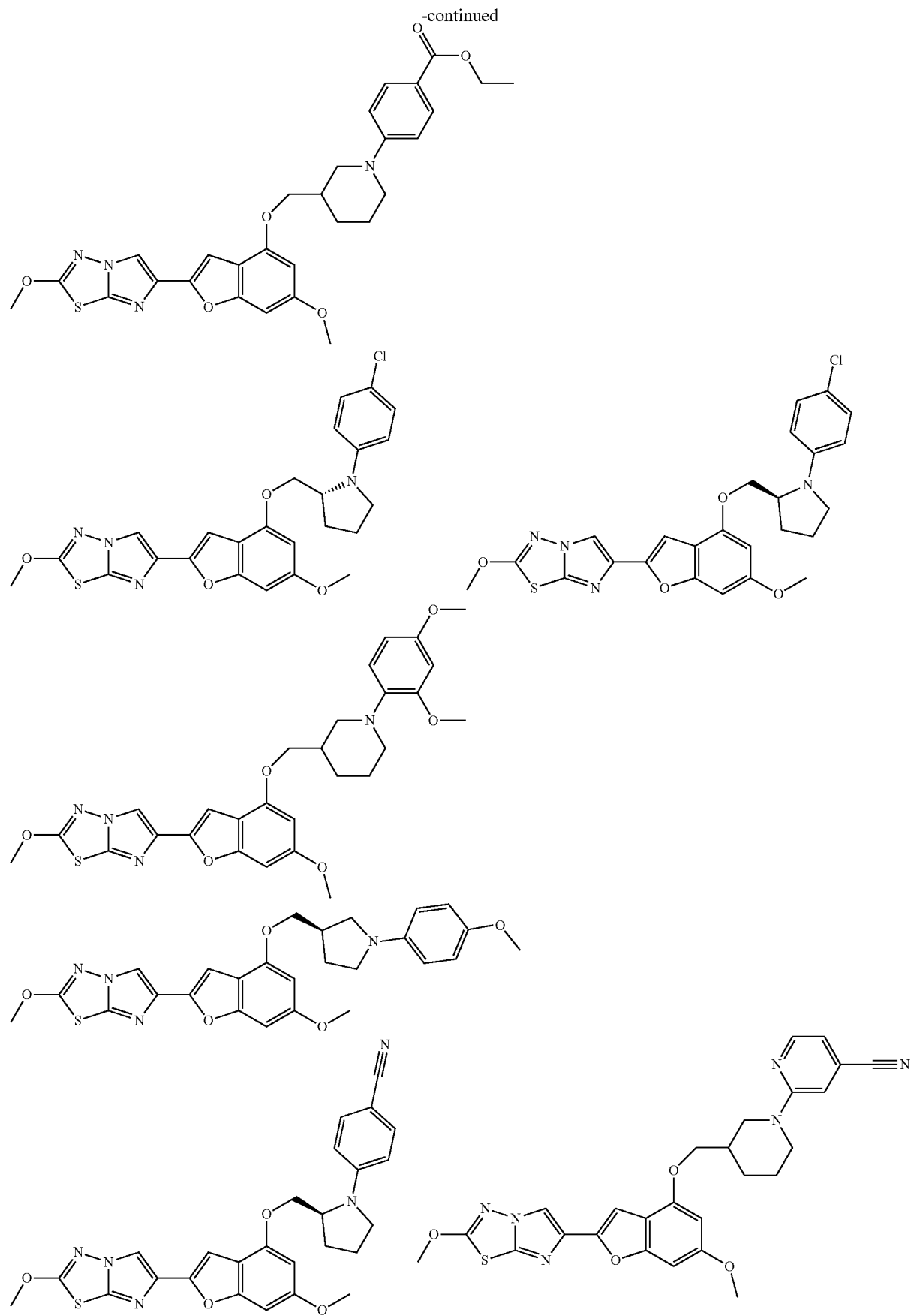

21
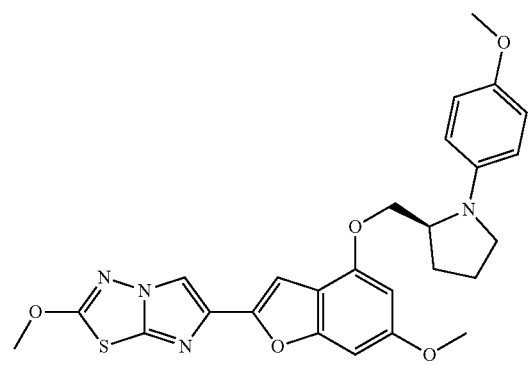
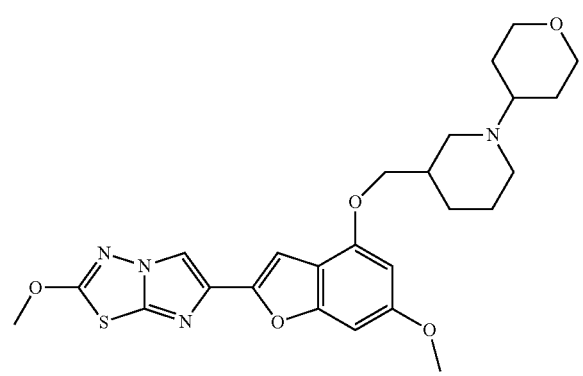
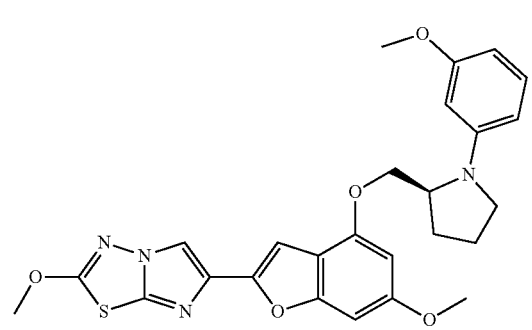
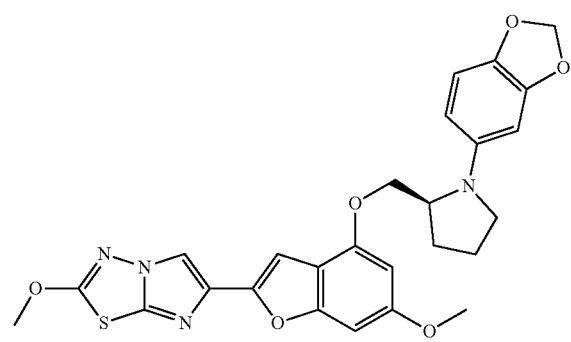
22
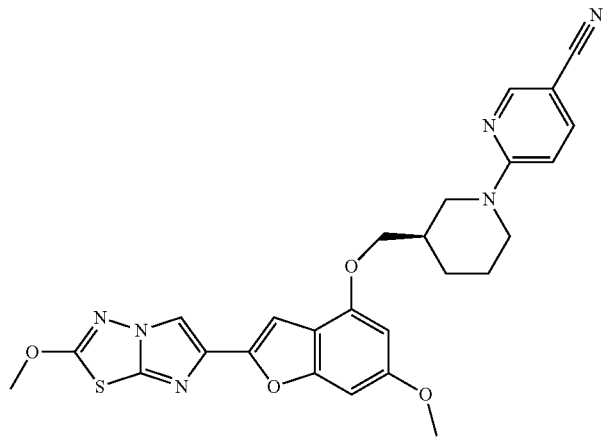
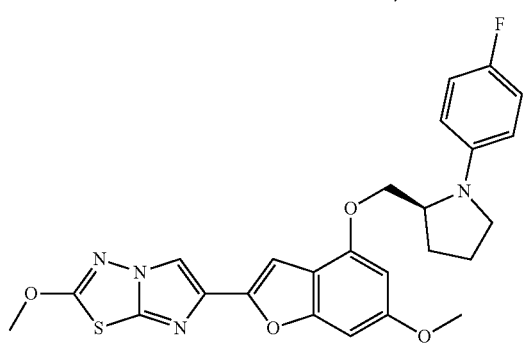
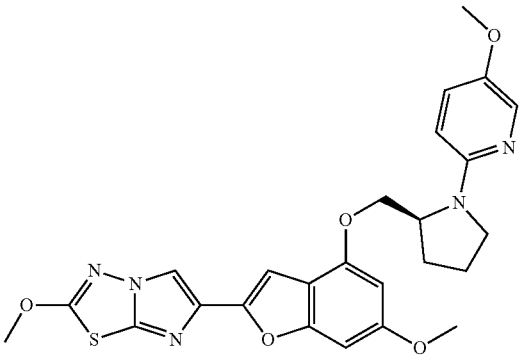
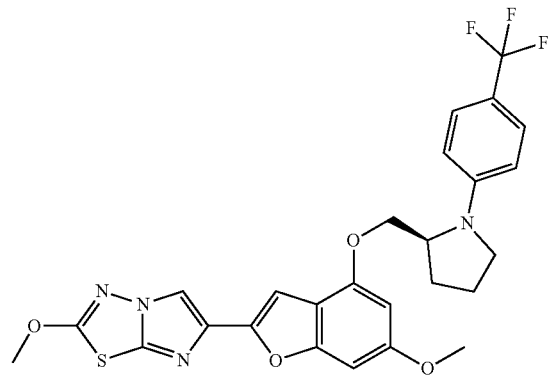

23                                                    24
-continued
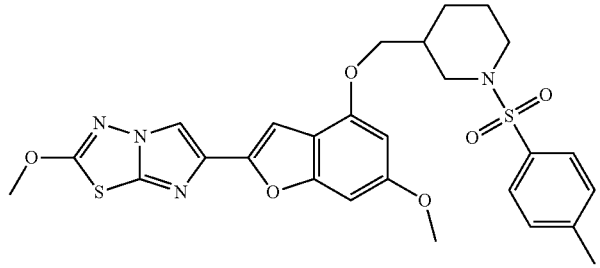
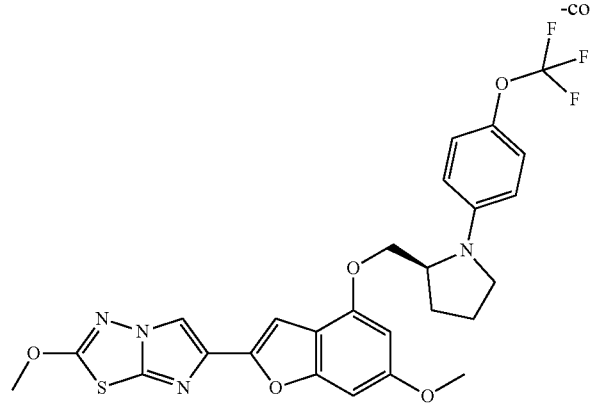
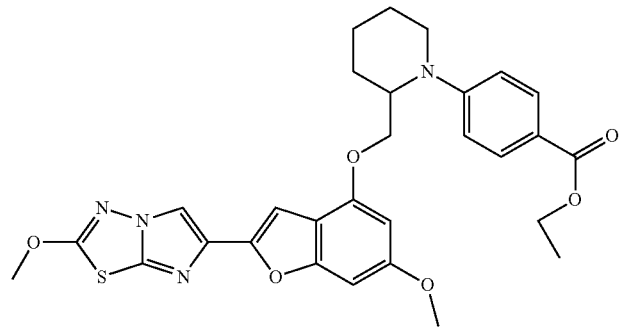
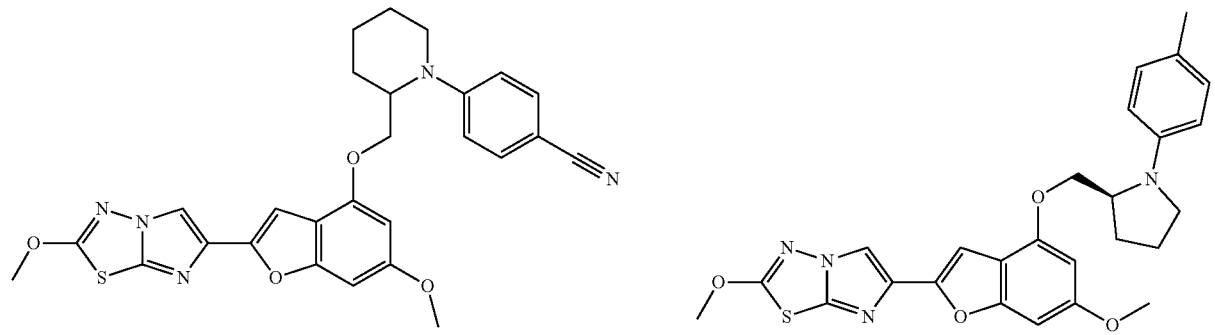
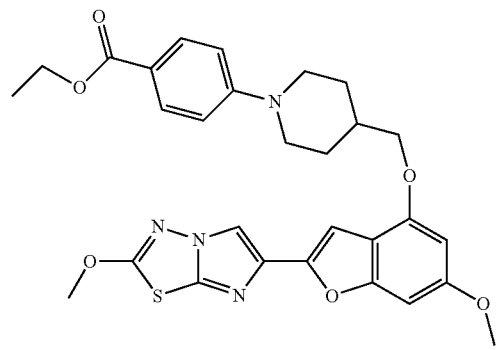
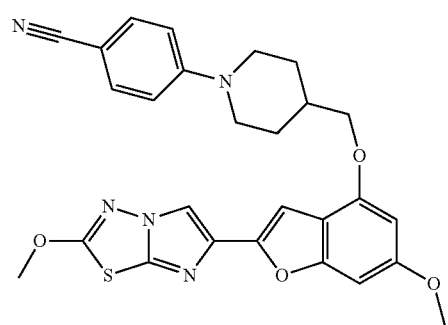

-continued
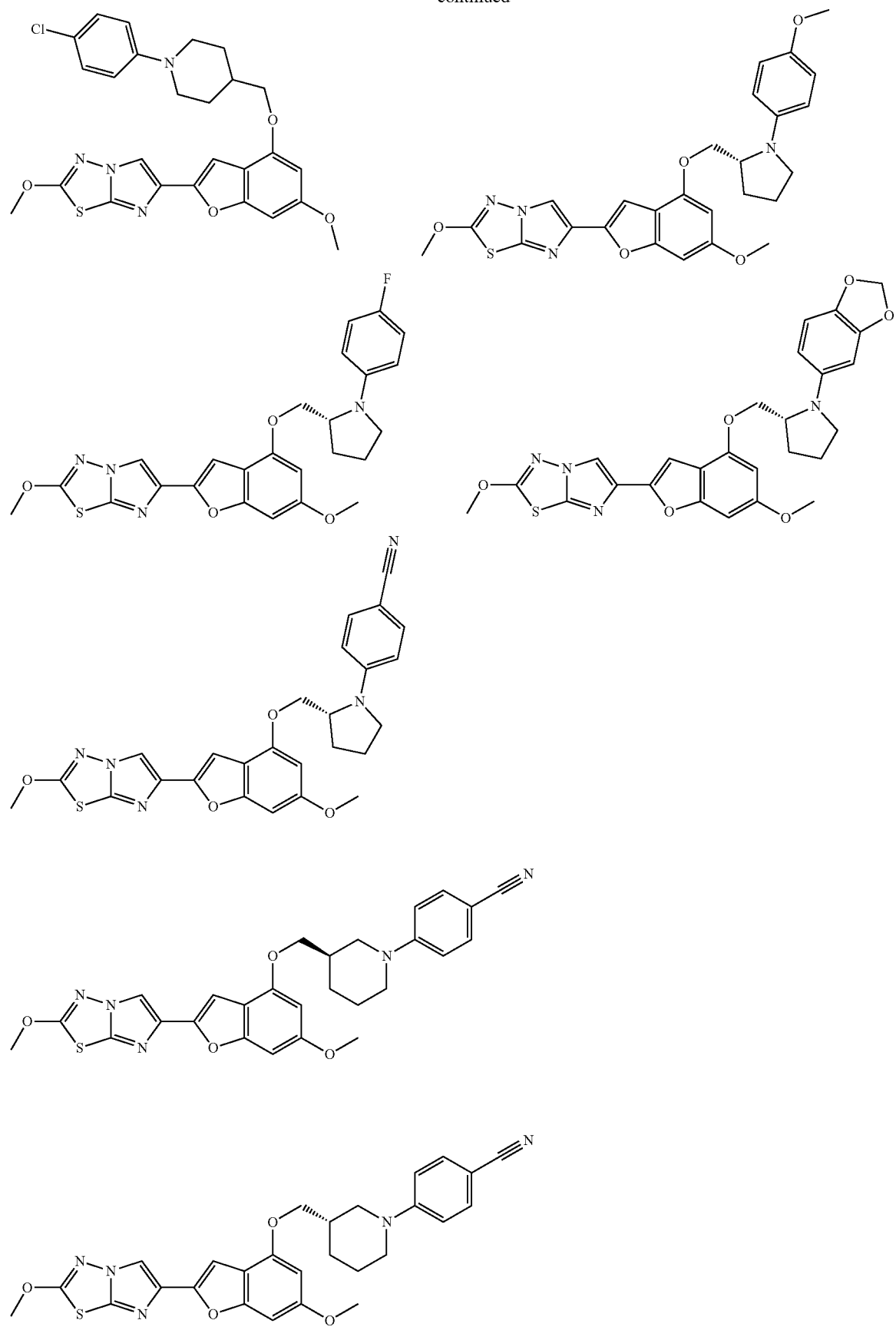

-continued
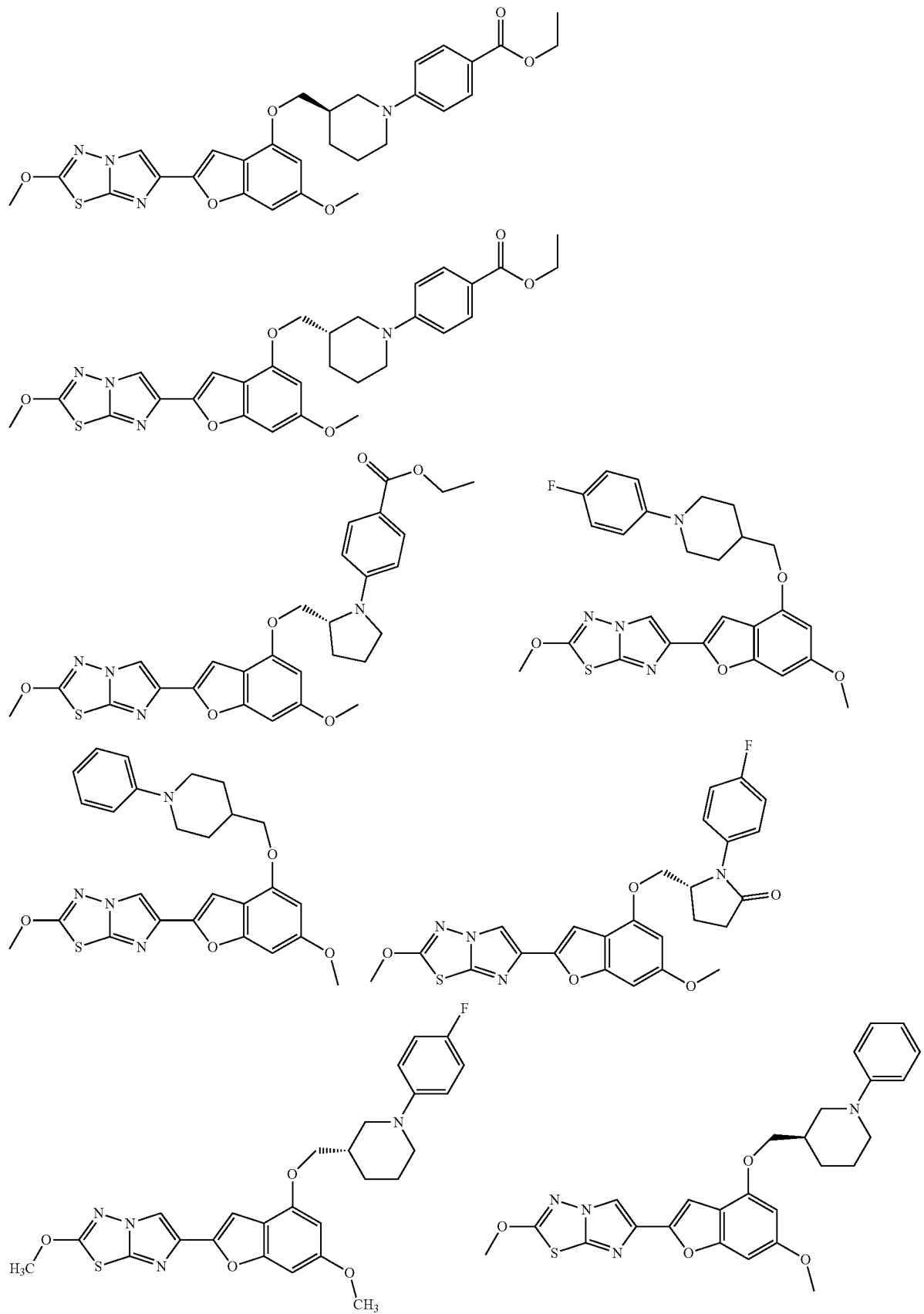

-continued
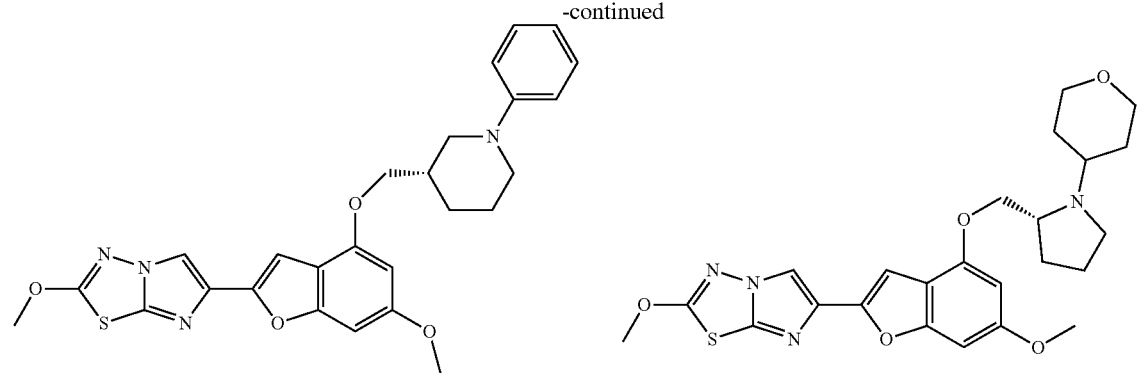
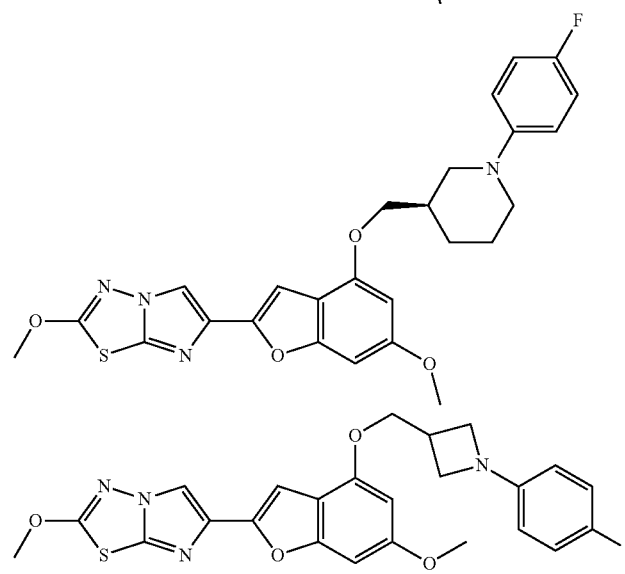
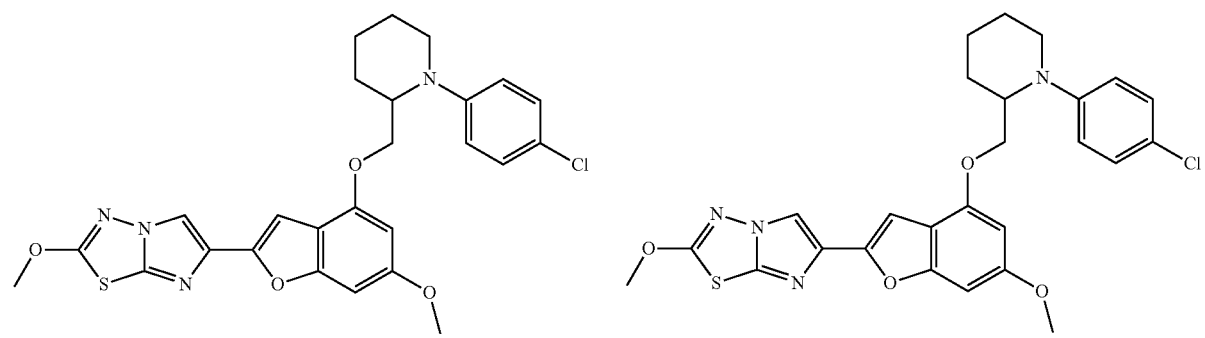
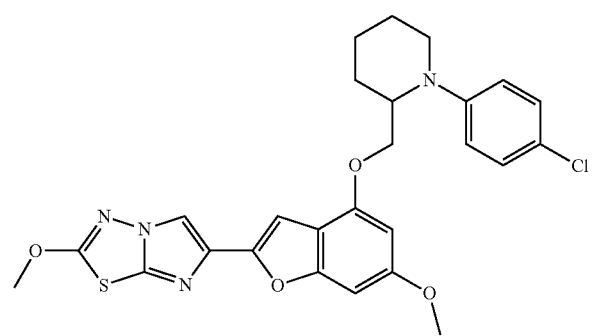

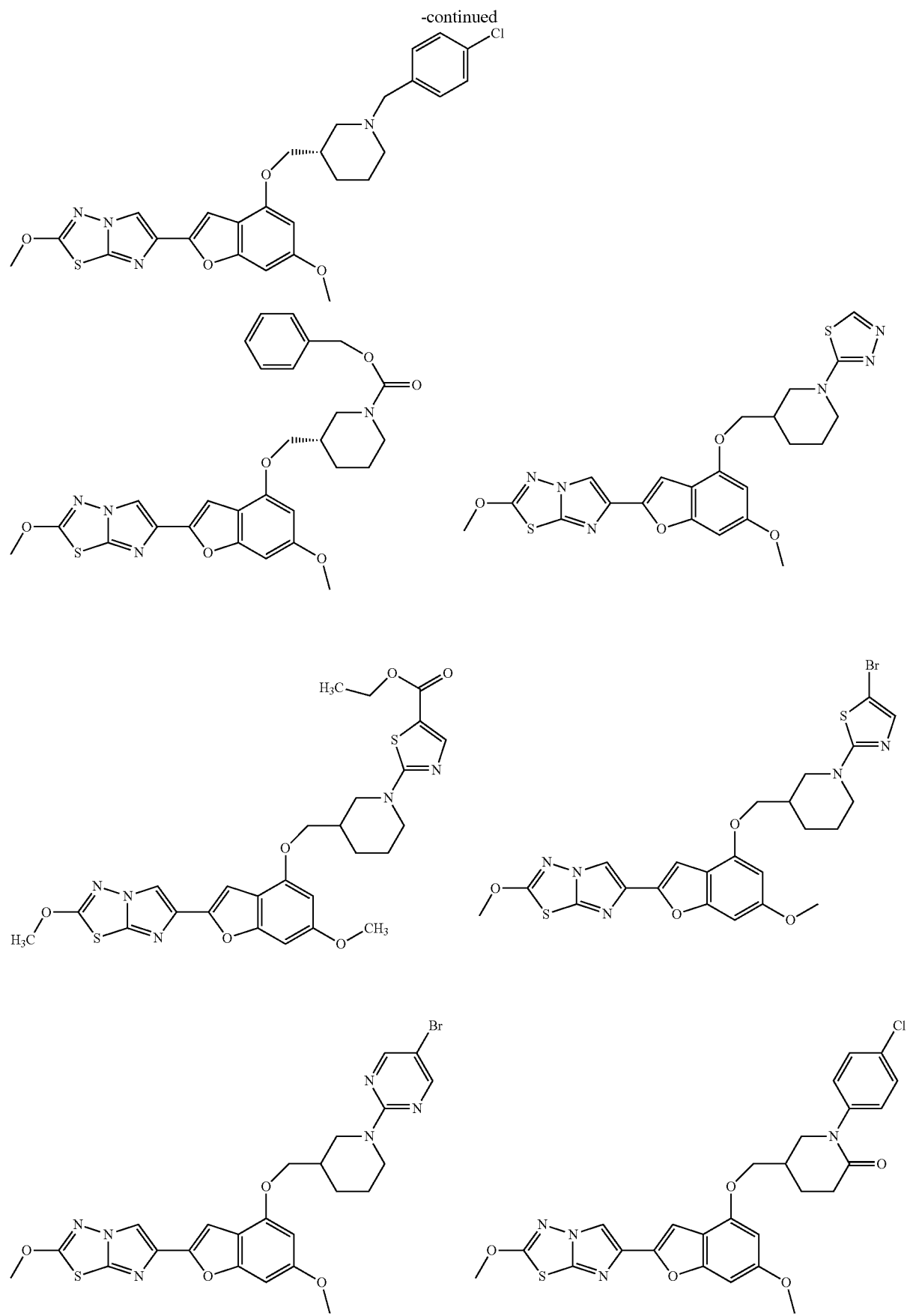

-continued
33
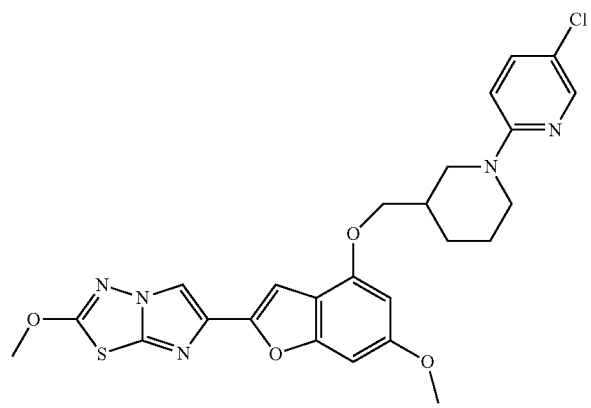
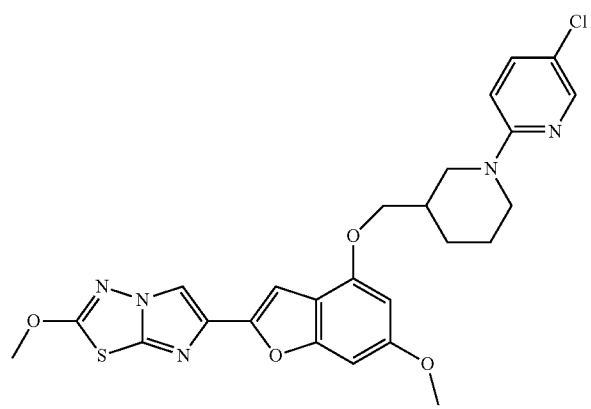
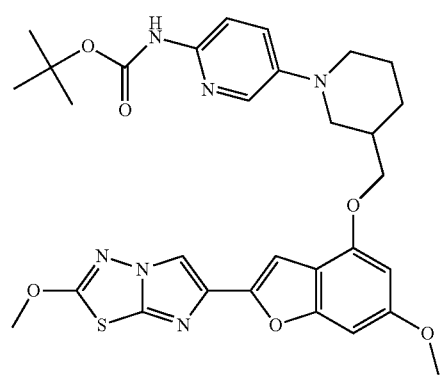
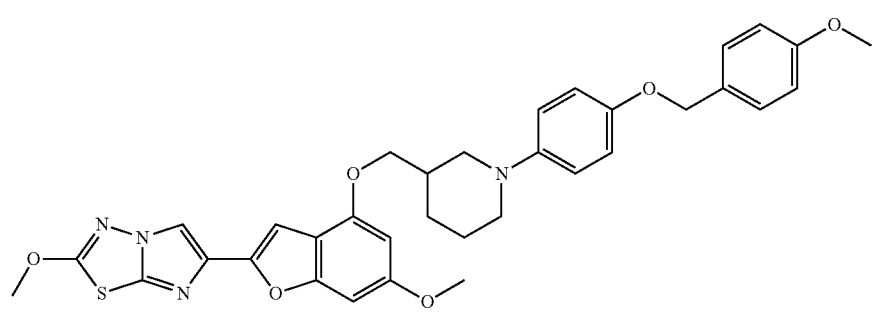
34
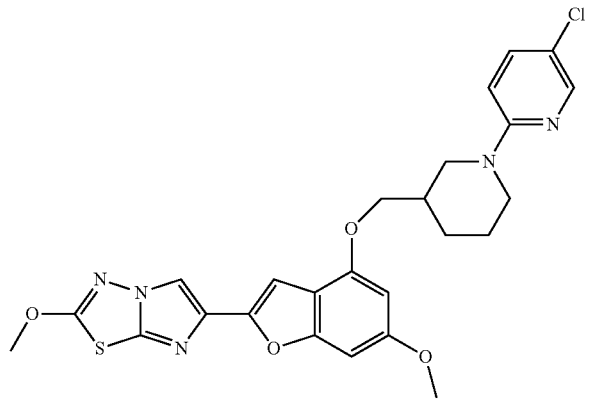
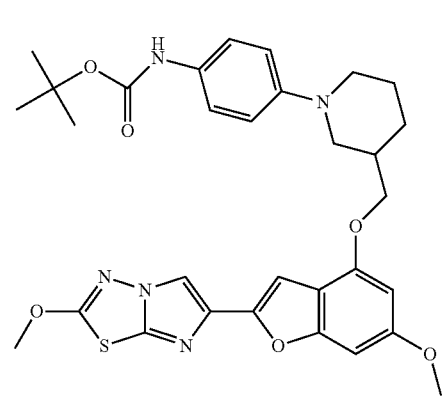
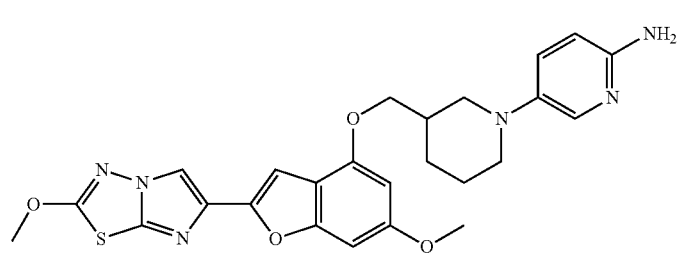

-continued

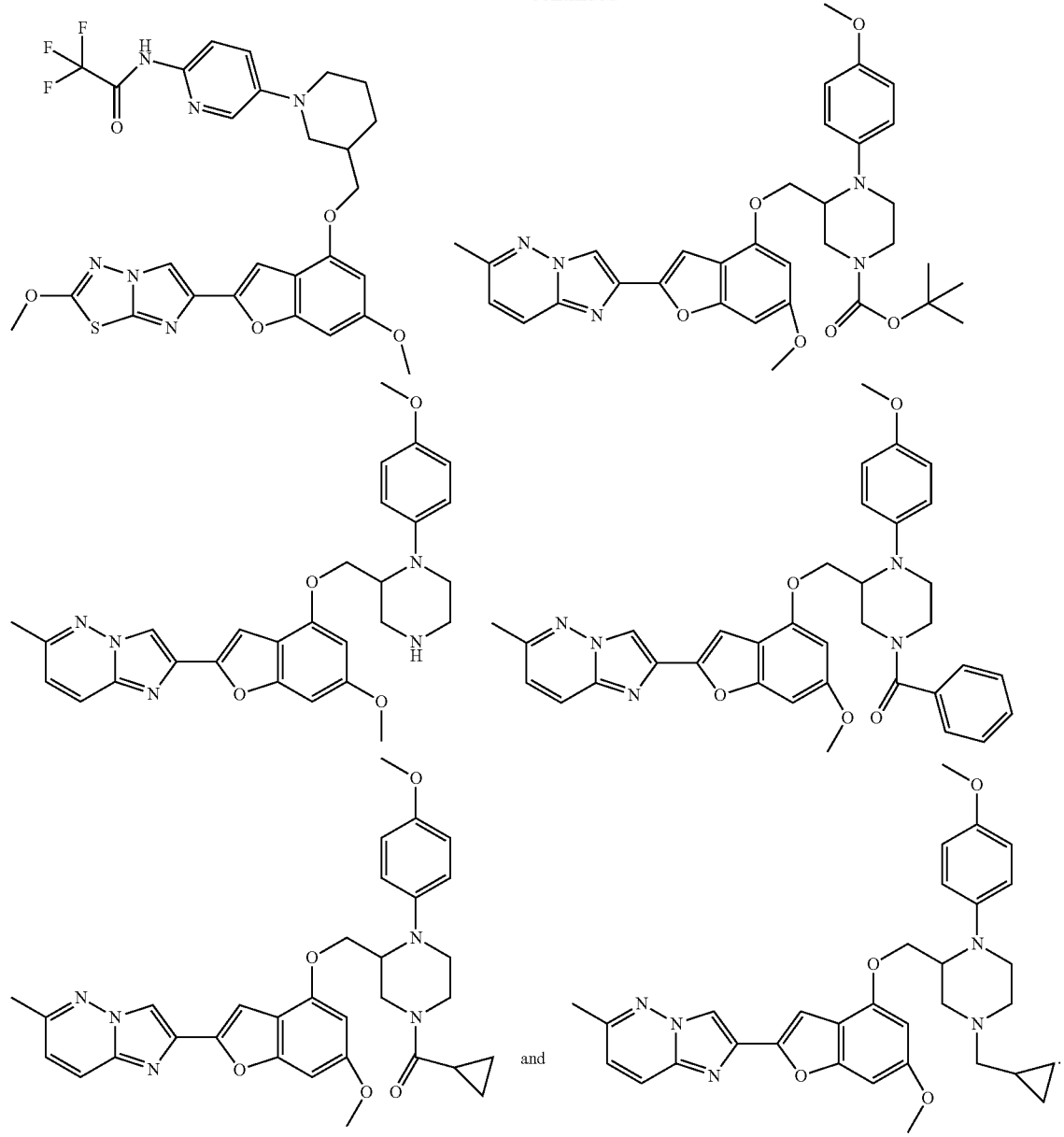

Preferably, PAR4 compounds of the invention have IC$_{50}$s in the FLIPR Assay (described hereinafter) of about 10 μM, preferably 5 μM or less, more preferably 500 nM or less, and even more preferably 10 nM or less. Activity data for a number of these compounds is presented in the table later in this specification.

In some embodiments, the present invention provides at least one compound of the present invention or a stereoisomer, tautomer, pharmaceutically acceptable salt, solvate, prodrug or esters thereof.

In some embodiments, the present invention provides a pharmaceutical composition, which includes a pharmaceutically acceptable carrier and a therapeutically effective amount of a compound of Formula I, IA, IB, IC, ID or IE, preferably, a compound selected from one of the examples, or stereoisomers, tautomers, pharmaceutically acceptable salts, prodrug or esters, or solvates thereof, alone or in combination with another therapeutic agent.

In some embodiments, the present invention provides a pharmaceutical composition which further includes another therapeutic agent(s). In a preferred embodiment, the present invention provides a pharmaceutical composition, wherein the additional therapeutic agent(s) are an anti-platelet agent or a combination thereof. Preferably, the anti-platelet agent(s) are P2Y12 antagonists and/or aspirin. Preferably, the P2Y12 antagonists are clopidogrel, ticagrelor, or prasugrel. In another preferred embodiment, the present invention provides a pharmaceutical composition, wherein the additional therapeutic agent(s) are an anticoagulant or a combination thereof. Preferably, the anticoagulant agent(s) are FXa inhibitors, FXIa inhibitors or thrombin inhibitors. Preferably, the FXa inhibitors are apixaban or rivaroxaban. Preferably, the thrombin inhibitor is dabigatran. For examples of FXIa inhibitors that may be useful in the present invention see International Patent Application Publication No. WO 2011/10040.

In some embodiments, the present invention provides a method for the treatment or prophylaxis of a thromboembolic disorder which includes the step of administering to a subject (for example, a human) in need of such treatment or prophylaxis a therapeutically effective amount of at least one of the compounds of the present invention or stereoisomers, tautomers, pharmaceutically acceptable salts, solvates, or prodrug or esters thereof.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB, IC, ID or IE, preferably, a compound selected from one of the examples, or stereoisomers, tautomers, pharmaceutically acceptable salts, prodrug or esters, or solvates thereof, or stereoisomers, tautomers, pharmaceutically acceptable salts, prodrug or esters, or solvates thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB, IC, ID or IE, preferably, a compound selected from one of the examples, or stereoisomers, tautomers, pharmaceutically acceptable salts, prodrug or esters, or solvates thereof, or stereoisomers, tautomers, pharmaceutically acceptable salts, prodrug or esters, or solvates thereof, wherein the thromboembolic disorder is selected from the group consisting of acute coronary syndrome, unstable angina, stable angina, ST-elevated myocardial infarction, non-ST-elevated myocardial infarction, atrial fibrillation, myocardial infarction, transient ischemic attack, stroke, atherosclerosis, peripheral arterial disease, venous thrombosis, deep vein thrombosis, thrombophlebitis, arterial embolism, coronary arterial thrombosis, cerebral arterial thrombosis, cerebral embolism, kidney embolism, pulmonary embolism, cancer-related thrombosis, and thrombosis resulting from medical implants, devices, and procedures in which blood is exposed to an artificial surface that promotes thrombosis.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB, IC, ID or IE, preferably, a compound selected from one of the examples, or stereoisomers, tautomers, pharmaceutically acceptable salts, prodrug or esters, or solvates thereof, or stereoisomers, tautomers, pharmaceutically acceptable salts, prodrug or esters, or solvates thereof, wherein the thromboembolic disorder is selected from the group consisting of acute coronary syndrome, unstable angina, stable angina, ST-elevated myocardial infarction, and non-ST-elevated myocardial infarction.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB, IC, ID or IE, preferably, a compound selected from one of the examples, or stereoisomers, tautomers, pharmaceutically acceptable salts, prodrug or esters, or solvates thereof, or stereoisomers, tautomers, pharmaceutically acceptable salts, prodrug or esters, or solvates thereof, wherein the thromboembolic disorder is selected from the group consisting of transient ischemic attack and stroke.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB, IC, ID or IE, preferably, a compound selected from one of the examples, or stereoisomers, tautomers, pharmaceutically acceptable salts, prodrug or esters, or solvates thereof, or stereoisomers, tautomers, pharmaceutically acceptable salts, prodrug or esters, or solvates thereof, wherein the thromboembolic disorder is peripheral arterial disease.

In some embodiments, the present invention includes a method as described above wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In some embodiments, the present invention includes a method of inhibiting or preventing platelet aggregation, which includes the step of administering to a subject (such as a human) in need thereof a therapeutically effective amount of a PAR4 antagonist, which is a compound of Formula I, IA, IB, IC, ID or IE, preferably, a compound selected from one of the examples, or stereoisomers, tautomers, pharmaceutically acceptable salts, prodrug or esters, or solvates thereof, of the invention.

OTHER EMBODIMENTS OF THE INVENTION

In some embodiments, the present invention provides a process for making a compound of the present invention or a stereoisomer, tautomer, pharmaceutically acceptable salt, solvate or prodrug or esters thereof.

In some embodiments, the present invention provides an intermediate for making a compound of the present invention or a stereoisomer, tautomer, pharmaceutically acceptable salt, solvate or prodrug or esters thereof.

In some embodiments, the invention provides a method of treatment or prophylaxis of a thromboembolic disorder involving administering to a subject in need thereof (e.g., a human) a therapeutically effective amount of a compound that binds to PAR4 (such as a compound of Formula I, IA, IB, IC, ID or IE of the invention) and inhibits PAR4 cleavage and/or signaling, wherein said subject has a dual PAR1/PAR4 platelet receptor repertoire.

In some embodiments, the present invention provides a compound of the present invention or stereoisomers, tautomers, pharmaceutically acceptable salts, solvates, or prodrug or esters thereof, for use in therapy for the treatment or prophylaxis of a thromboembolic disorder.

In some embodiments, the present invention also provides the use of a compound of the present invention or stereoisomers, tautomers, pharmaceutically acceptable salts, solvates, or prodrug or esters thereof, for the manufacture of a medicament for the treatment or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

Chemistry

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis-, trans- or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The molecular weight of compounds of the present invention is preferably less than about 800 grams per mole.

As used herein, the term "alkyl" or "alkylene", alone or as part of another group, is intended to include both branched and straight-chain saturated aliphatic hydrocarbon groups having from 1 to 10 carbons or the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl), as well as chain isomers thereof, and the like as well as such groups which may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio as well as (=O), $OR_a$, $SR_a$, (=S), —$NR_aR_b$, —$N(alkyl)_3^+$, —$NR_aSO_2$, —$NR_aSO_2R_c$, —$SO_2R$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_1$-$C_4$ alkylene)N-$R_aR_b$, —$C(=O)NR_a(SO_2)R_b$, —$CO_2(C_1$-$C_4$ alkylene) $NR_aR_b$, —$NR_aC(=O)R_b$, —$NR_aCO_2R_b$, —$NR_a(C_1$-$C_4$ alkylene)$CO_2R_b$, =N—OH, =N—O-alkyl, wherein $R_a$ and $R_b$ are the same or different and are independently selected from hydrogen, alkyl, alkenyl, $CO_2H$, $CO_2$(alkyl), $C_3$-$C_7$cycloalkyl, phenyl, benzyl, phenylethyl, naphthyl, a 4- to 7-membered heterocyclo, or a 5- to 6-membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each R group optionally has up to three further substituents attached at any available carbon or nitrogen atom of $R_a$, $R_b$, and/or R, said substituent(s) being the same or different and are independently selected from the group consisting of ($C_1$-$C_6$)alkyl, ($C_2$-$C_6$)alkenyl, hydroxy, halogen, cyano, nitro, $CF_3$, $O(C_1$-$C_6$ alkyl), $OCF_3$, $C(=O)H$, $C(=O)(C_1$-$C_6$ alkyl), $CO_2H$, $CO_2(C_1$-$C_6$ alkyl), $NHCO_2(C_1$-$C_6$ alkyl), —$S(C_1$-$C_6$ alkyl), —$NH_2$, $NH(C_1$-$C_6$ alkyl), $N(C_1$-$C_6$ alkyl)$_2$, $N(CH_3)_3^+$, $SO_2(C_1$-$C_6$ alkyl), $C(=O)(C_1$-$C_4$ alkylene)$NH_2$, $C(=O)(C_1$-$C_4$ alkylene)NH(alkyl), $C(=O)(C_1$-$C_4$ alkylene)N($C_1$-$C_4$ alkyl)$_2$, $C_3$-$C_7$ cycloalkyl, phenyl, benzyl, phenylethyl, phenyloxy, benzyloxy, naphthyl, a 4- to 7-membered heterocyclo, or a 5- to 6-membered heteroaryl. When a substituted alkyl is substituted with an aryl, heterocyclo, cycloalkyl, or heteroaryl group, said ringed systems are as defined below and thus may have zero, one, two, or three substituents, also as defined below.

"Alkenyl" or "alkenylene", alone or as part of another group, is intended to include hydrocarbon chains of either straight or branched configuration and having one or more carbon-carbon double bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, and/or alkylthio.

"Alkynyl" or "alkynylene", alone or as part of another group, is intended to include hydrocarbon chains of either straight or branched configuration and having one or more carbon-carbon triple bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio.

The term "alkoxy" or "alkyloxy", alone or as part of another group, refers to an —O-alkyl group, where alkyl is as defined above. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy", alone or as part of another group, represents an alkyl group or alkoxy group as defined above with the indicated number of carbon atoms attached through a sulfur bridge; for example methyl-S— and ethyl-S—.

"Halo" or "halogen", alone or as part of another group, includes fluoro, chloro, bromo, and iodo.

"Haloalkyl" is intended to include both branched and straight-chain saturated aliphatic hydrocarbon groups having the specified number of carbon atoms, substituted with 1 to 7 halogens, preferably 1 to 4 halogens, preferably F and/or $C_1$. Examples of haloalkyl include, but are not limited to, fluoromethyl, difluoromethyl, trifluoromethyl, trichloromethyl, pentafluoroethyl, pentachloroethyl, 1,1-difluoroethyl, 1-fluoroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 to 7 fluorine atoms, preferably 1 to 4 fluorine atoms.

"Halo-$C_1$-$C_2$-alkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulfur bridge; for example trifluoromethyl-S—, and pentafluoroethyl-S—.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 10 carbons forming the ring ($C_3$-$C_{10}$ cycloalkyl), and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl, norbornyl,

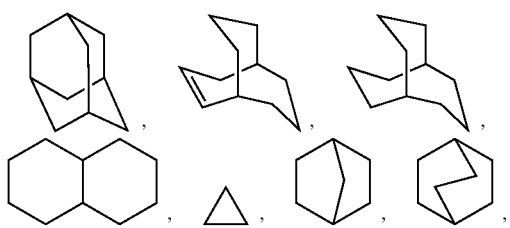

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl, as well as such groups including 2 free bonds and thus are linking groups.

As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_{6-10}$ aryl" refers to phenyl and naphthyl. Unless otherwise specified, "aryl", "$C_{6-10}$ aryl" or "aromatic residue" may be unsubstituted or substituted with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, $C(=O)CH_3$, $SCH_3$, $S(=O)CH_3$, $S(=O)_2CH_3$, $C_1$-$C_3$ alkyl, $CO_2H$, and $CO_2CH_3$.

As used herein, the term "heterocycle", "heterocyclo" or "heterocyclic" group is intended to mean a stable 4- to 14-membered monocyclic, bicyclic or tricyclic heterocyclic ring which is saturated and which consists of carbon atoms and 1, 2, 3, or 4 heteroatoms (or as disclosed herein) independently selected from the group consisting of N, NH, O and S and including any bicyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may optionally be substituted on carbon or on a nitrogen atom if the resulting compound is stable, with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, =O, $C(=O)CH_3$, $SCH_3$, S(=O)CH₃, S(=O)₂CH₃, C₁-C₃ alkyl, CO₂H and CO₂CH₃. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Spiro and bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. When the term "heterocycle" is used, it is not intended to include heteroaryl.

Exemplary monocyclic heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like.

Exemplary bicyclic heterocyclo groups include quinuclidinyl.

Preferred heterocyclo groups include

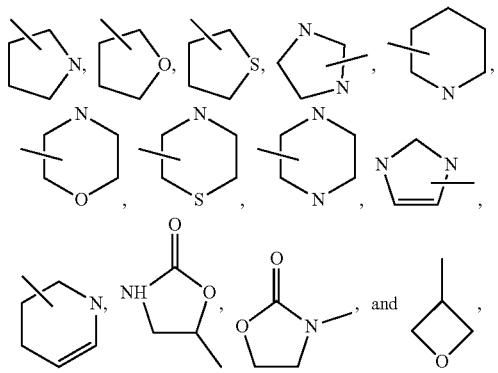

which optionally may be substituted.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are unsubstituted or substituted with 1 to 3 groups selected from OH, OC₁-C₃ alkoxy, Cl, F, Br, I, CN, NO₂, NH₂, N(CH₃)H, N(CH₃)₂, CF₃, OCF₃, OCHF₂, =O, C(=O)CH₃, SCH₃, S(=O)CH₃, S(=O)₂CH₃, C₁-C₃ alkyl, CO₂H and CO₂CH₃. The nitrogen atom is substituted or unsubstituted (i.e., N or NR wherein R is H or another substituent, if defined). The nitrogen and sulfur heteroatoms may optionally be oxidized (i.e., N→O and S(O)ₚ, wherein p is 0, 1 or 2). Bridged rings are also included in the definition of heteroaryl. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Preferred heteroaryl groups include

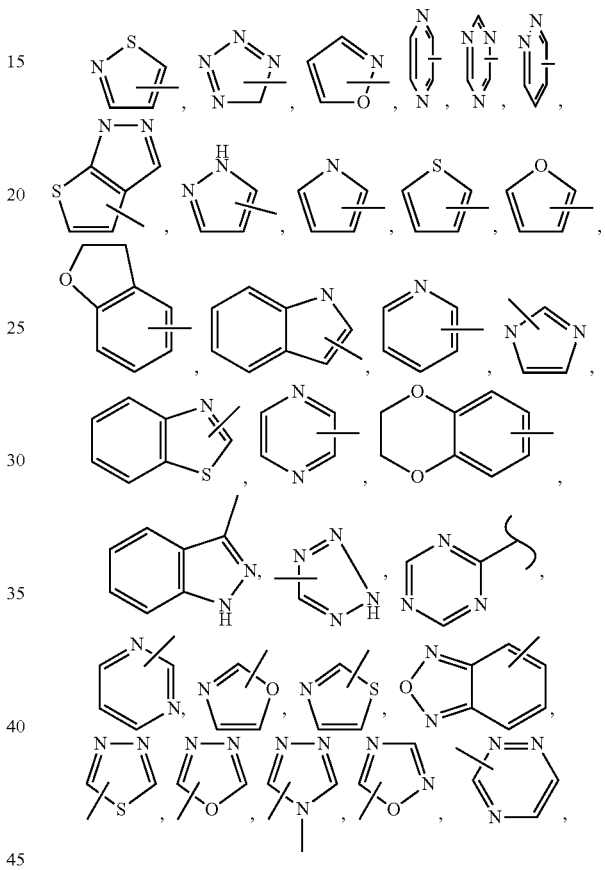

and the like.

When the term "unsaturated" is used herein to refer to a ring or group, which group may be fully unsaturated or partially unsaturated.

The term "acyl" alone or as part of another group refers to a carbonyl group linked to an organic radical, more particularly, the group C(=O)Rₑ, as well as the bivalent groups —C(=O)— or —C(=O)Rₑ—, which are linked to organic radicals. The group Rₑ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, and the like.

The designation "⌇" or "⸺" or "⸺" attached to a ring or other group refers to a free bond or linking group.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "counterion" is used to represent a negatively charged species such as chloride, bromide, hydroxide, acetate, and sulfate.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quaternary carbon atoms in compounds of the present invention, these can be replaced by silicon atoms, provided they do not form Si—N or Si—O bonds.

When any variable occurs more than one time in any constituent or formula for a compound, its definition at each occurrence is independent of its definition at every other occurrence. Thus, for example, if a group is shown to be substituted with 0 to 3 $R^{3a}$, then said group may optionally be substituted with up to three $R^{3a}$ groups, and at each occurrence $R^{3a}$ is selected independently from the definition of $R^{3a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V. Jr., ed., *Remington: The Science and Practice of Pharmacy*, 22nd Edition, Pharmaceutical Press, London, UK (2012), the disclosure of which is hereby incorporated by reference.

In addition, compounds of Formula I, IA, IB, IC or ID may have prodrug forms. Any compound that will be converted in vivo to provide the bioactive agent (i.e., a compound of Formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). Prodrugs and Targeted Delivery (*Methods and Principles in Medicinal Chemistry*), Vol 47, Wiley-VCH, 2011.

Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

Isotopically labeled compounds of the present invention, i.e., wherein one or more of the atoms described are replaced by an isotope of that atom (e.g., $^{12}C$ replaced by $^{13}C$ or by $^{14}C$; and isotopes of hydrogen including tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" for thin layer chromatography, "SM" for starting material, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "tlc" for thin layer chromatography. "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| AcOH | acetic acid |
| MeOH | methanol |
| EtOH | ethanol |
| EtOAc | ethyl acetate |
| Et$_2$O | diethyl ether |
| i-PrOH or IPA | isopropanol |
| HOAc | acetic acid |
| BOP reagent | benzotriazol-1-yloxytris(dimethylamino)phosphonium hexafluorophosphate |
| BBr$_3$ | boron tribromide |
| Boc | tert-butyloxycarbonyl |
| cDNA | complimentary DNA |
| CDCl$_3$ | deuterated chloroform |
| CH$_2$Cl$_2$ | dichloromethane |
| CH$_3$CN | acetonitrile |
| ACN | acetonitrile |
| DABCO | 1,4-diazabicyclo[2.2.2]octane |
| DCE | 1,2 dichloroethane |
| DCM | dichloromethane |
| DCC | dicyclohexylcarbodiimide |
| DIAD | diisopropyl azodicarboxylate |
| DIEA or DIPEA | N,N-diisopropylethylamine |
| DME | 1,2-dimethoxyethane |
| DMF | dimethyl formamide |
| DMAP | N,N-dimethylaminopyridine |
| DMSO | dimethyl sulfoxide |
| DPPA | diphenyl phosphoryl azide |
| EDC (or EDC•HCl) or EDCI (or EDCI•HCl) or EDAC | 3-ethyl-3'-(dimethylamino)propyl-carbodiimide hydrochloride or 1-(3-dimethylaminopropyl)-3-ethylcarbodiimide hydrochloride |
| EDTA | ethylenediaminetetraacetic acid |
| HATU | O-(7-azabenzotriazol-1-yl)-N,N,N',N'-tetramethyluronium hexafluorophosphate |
| HCl | hydrochloric acid |
| HEPES | 4-(2-hydroxyethyl)piperazine-1-ethanesulfonic acid |
| Hex | hexane |
| HOBt or HOBT | 1-hydroxybenzotriazole monohydrate |
| Hunig's base | N,N-diisopropylethyl amine |
| LAH | lithium aluminum hydride |
| LDA | Lithium diisopropylamide |
| LiHMDS | Lithium bis(trimethylsilyl) amide |
| mCPBA or m-CPBA | meta-chloroperbenzoic acid |
| NMM | N-methylmorpholine |
| Pd/C | palladium on carbon |
| PPA | polyphosphoric acid |
| PS | polystyrene |
| PXPd2 | bis[di-tert-butyl phosphinous chloride-kP]di-m-chlorodichloro dipalladium |
| PyBOP | (benzotriazol-1-yloxy)tripyrrolidino-phosphonium hexafluorophosphate |
| TEA | triethylamine |
| TFA | trifluoroacetic acid |
| THF | tetrahydrofuran |
| TRIS | tris(hydroxymethyl)aminomethane |
| KOAc | potassium acetate |
| K$_3$PO$_4$ | potassium phosphate |
| MgSO$_4$ | magnesium sulfate |
| NaCl | sodium chloride |
| NaH | sodium hydride |
| NaHCO$_3$ | sodium bicarbonate |
| NaOH | sodium hydroxide |
| Na$_2$SO$_3$ | sodium sulfite |
| Na$_2$SO$_4$ | sodium sulfate |
| NH$_3$ | ammonia |
| NH$_4$Cl | ammonium chloride |
| NH$_4$OH | ammonium hydroxide |
| OTs | tosylate, para-toluenesulfonate |
| PBr$_3$ | phosphorous tribromide |
| Pd(PPh$_3$)$_4$ | tetrakis(triphenylphosphine) palladium (0) |
| (S,S)-EtDuPhosRh(I) | (+)-1,2-bis((2S,5S)-2,5-diethyl-phospholano)benzene (cyclooctadiene)rhodium (I) trifluoromethanesulfonate |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (Greene's Protective Groups In Organic Synthesis, 4th Edition, Wiley-Interscience (2006)).

Synthetic Schemes

Compounds of formula I of this invention can be obtained by condensation of an amine of formula III with a ketone of formula IV which contains a leaving group Z such as a bromide, iodide or tosylate and a protecting group PG such as benzyl as shown in Scheme 1. Both compounds of formula III and IV are commercially available or can be prepared by means known to one skilled in the art. This condensation is promoted by heating, either thermally or preferably by microwave irradiation. The protecting group can be removed by methods known in the art, such as $BCl_3$ at −78° C. in the presence of pentamethylbenzene. Subsequent alkylation using either an alcohol VI under Mitsunobu conditions or a bromide VII in the presence of base such as potassium carbonate provides the compounds of Formula I. Alcohols and bromides VI and VII are commercially available or can be prepared by methods known in the art.

Substituted benzofurans XI, bearing α-bromoketone substituents at the 2-position, can be prepared as shown in Scheme 2. o-Hydroxy benzaldehydes VIII can be prepared by methods known to one skilled in the art of organic synthesis, and can be condensed with ketones of formula IX, bearing a leaving group Q such as chloro, bromo or tosyloxy, to give benzofurans X. Bromination of compounds of formula X affords bromoketones XI, which can be condensed with a substituted aminoheterocycle III according to Scheme 1 to give compounds of Formula I. Bromoketones XI are a specific subset of compounds IV in Scheme 1.

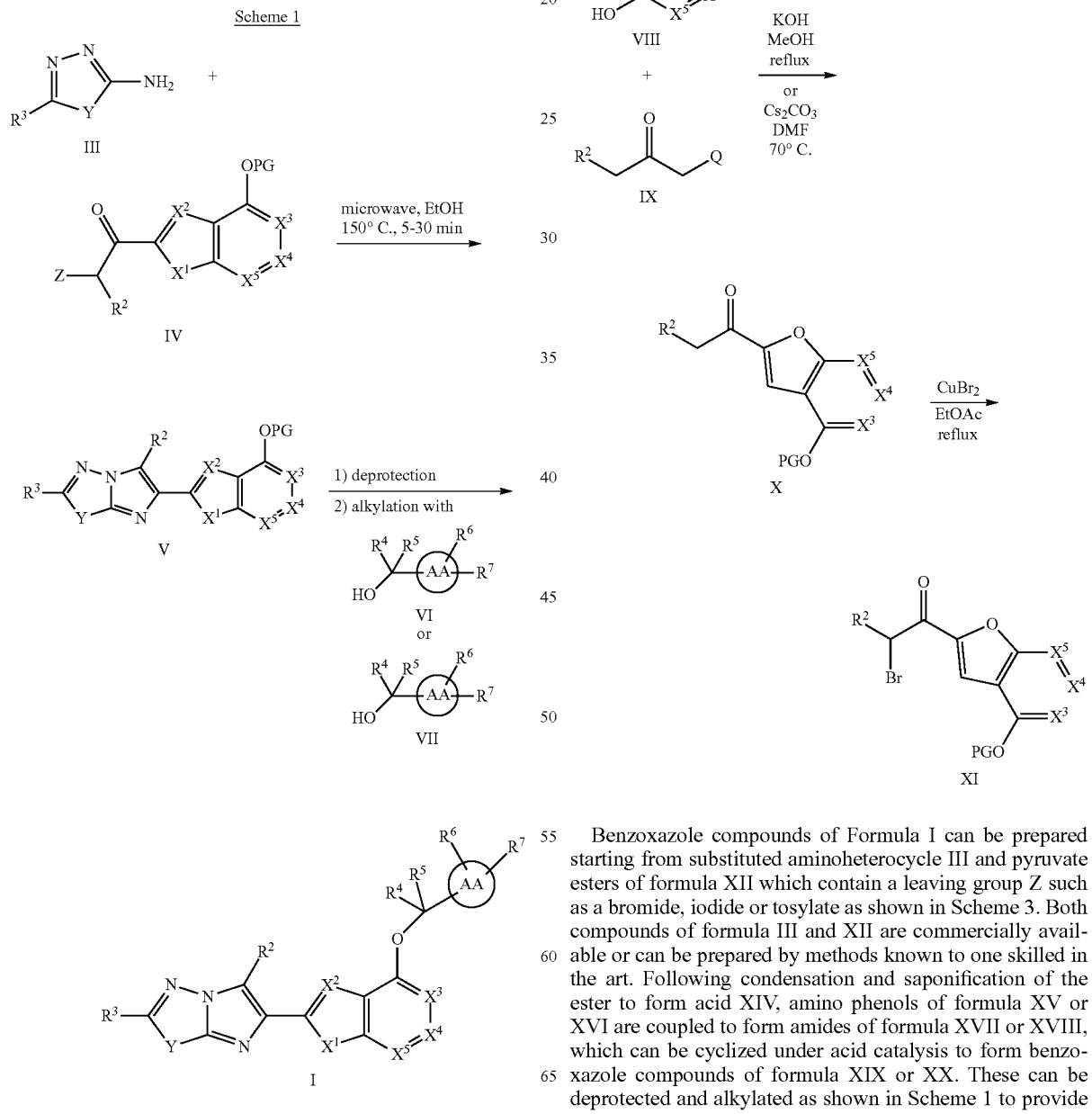

Benzoxazole compounds of Formula I can be prepared starting from substituted aminoheterocycle III and pyruvate esters of formula XII which contain a leaving group Z such as a bromide, iodide or tosylate as shown in Scheme 3. Both compounds of formula III and XII are commercially available or can be prepared by methods known to one skilled in the art. Following condensation and saponification of the ester to form acid XIV, amino phenols of formula XV or XVI are coupled to form amides of formula XVII or XVIII, which can be cyclized under acid catalysis to form benzoxazole compounds of formula XIX or XX. These can be deprotected and alkylated as shown in Scheme 1 to provide compounds of Formula I.

Scheme 3

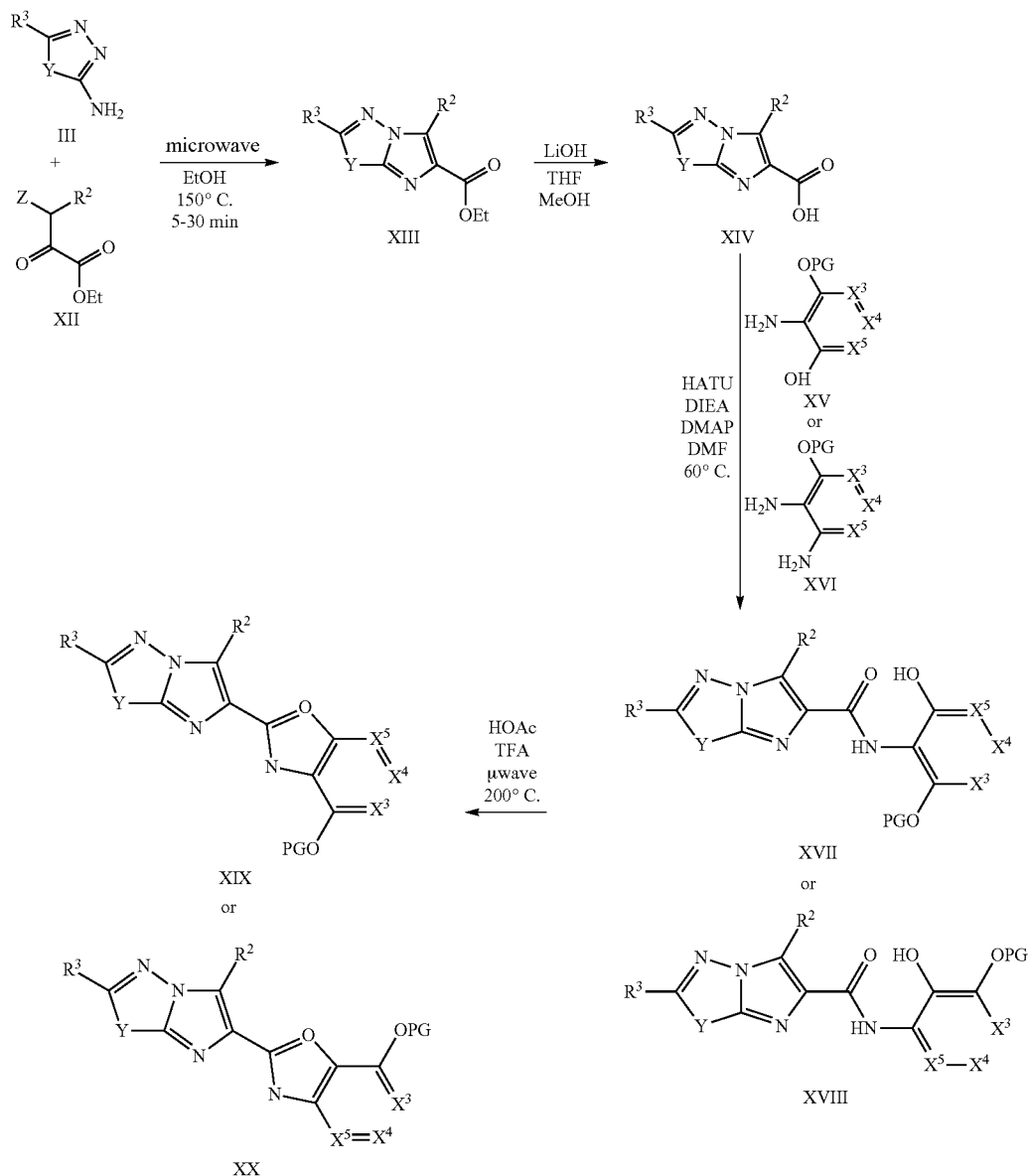

Aminoheterocycles XXII can be prepared from carbon disulfide via the thioxanthate intermediate XXI as shown in Scheme 4. These aminoheterocycles are a specific subset of compounds III in Scheme I, and are useful for the preparation of compounds of Formula I.

Scheme 4

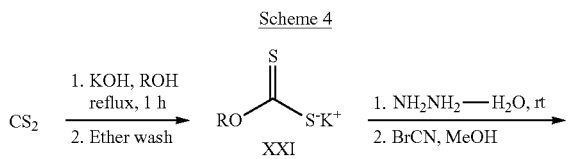

-continued

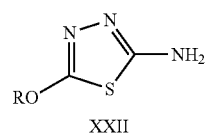

Aminoheterocycles XXVIII, which are useful intermediates for preparation of compounds of Formula I where Y=—CH$_2$CH$_2$—, can be prepared from ketoesters XXIII. Cyclization with hydrazine, followed by oxidation with bromine gives pyridazinones XXV. Chlorination, displacement with hydrazine, and subsequent hydrogenation provides aminoheterocycles XXVIII, which are a specific subset of compounds III in Scheme I. As such, these aminoheterocycles are useful for the preparation of compounds of Formula I.

Scheme 5

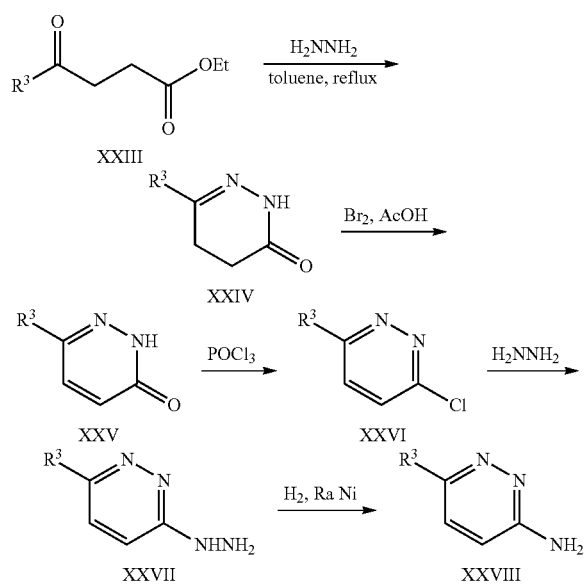

Compounds of formula XXXIII of this invention can be obtained by condensation of an amine of formula XXIX with a ketone of formula XXX which contains a leaving group V such as a bromide, chloride, iodide or tosylate and a protecting group PG such as benzyl as shown in Scheme 6. Both compounds of formula XXIX and XXX are commercially available or can be prepared by means known to one skilled in the art. This condensation is promoted by heating, either thermally or preferably by microwave irradiation. The protecting group can be removed by methods known in the art, such as BCl$_3$ at −78° C. in the presence of pentamethylbenzene, to give intermediates XXXII. Subsequent alkylation using either an alcohol VI under Mitsunobu conditions or a bromide VII in the presence of base such as cesium carbonate provides the compounds of Formula XXXIII. Alcohols VI and bromides VII are commercially available or can be prepared by methods known in the art.

Scheme 6

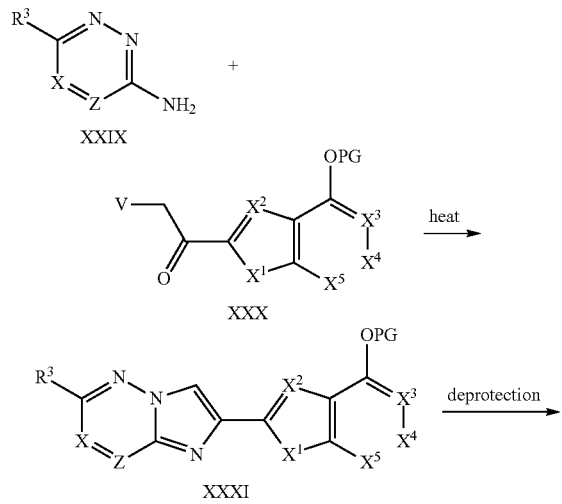

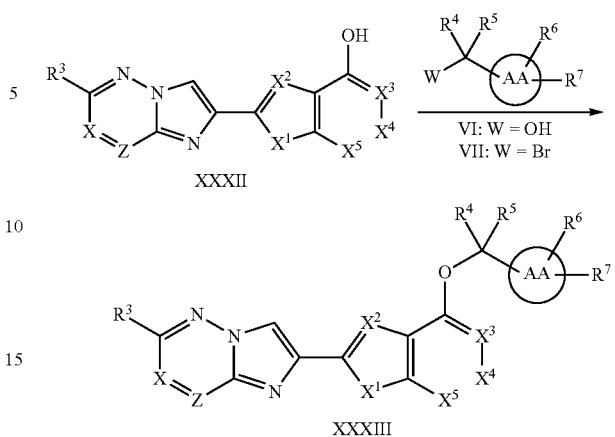

Compounds of formula XXXVI of this invention can be obtained by condensation of an amine of formula XXXIV with a ketone of formula XXX which contains a leaving group V such as a bromide, chloride, iodide or tosylate and a protecting group PG such as benzyl as shown in Scheme 7. Both compounds of formula XXXIV and XXX are commercially available or can be prepared by means known to one skilled in the art. This condensation is promoted by heating, either thermally or preferably by microwave irradiation. The protecting group can be removed by methods known in the art, such as BCl$_3$ at −78° C. in the presence of pentamethylbenzene. Subsequent alkylation using either an alcohol VI under Mitsunobu conditions or a bromide VII in the presence of base such as cesium carbonate provides the compounds of Formula XXXVI. Alcohols VI and bromides VII are commercially available or can be prepared by methods known in the art.

Scheme 7

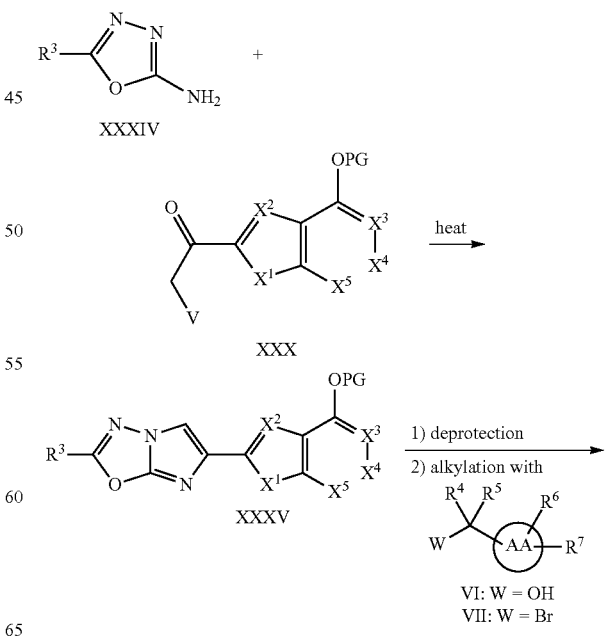

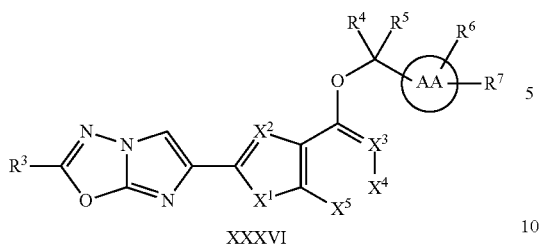

XXXVI

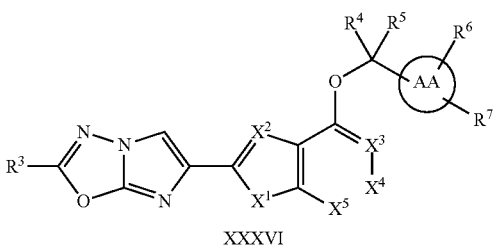

XXXVI

In the event that the condensation of an amine of formula XXXIV with a ketone of formula XXX does not proceed to compounds of Formula XXXV in a single step, compounds of Formula XXXV can be prepared from dehydration of intermediates of Formula XXXVIII with POCl$_3$, as shown in Scheme 8. Compounds of formula XXXVIII can be prepared from the hydrolysis of compounds of Formula XXXVII, which in turn can be derived from the reaction of an amine of formula XXXIV with a ketone of formula XXX. Compounds XXXV can be converted to compounds of Formula XXXVI by removal of the protecting group (PG) and alkylation as discussed in Scheme 7.

Benzothiazole compounds of the invention can be prepared from intermediates described in Scheme 9. Reaction of bromo anilines XXXVII, which are commercially available or can be prepared by one skilled in the art, with benzoylisothiocyanate affords thioureas XXXIX, which are hydrolyzed with NaOH and heat to afford thioureas XL. These thioureas can be oxidatively cyclized with, for instance, bromine in a solvent such as chloroform, to give aminobenzothiazoles XLI. Reaction with an organic nitrite provides benzothiazoles XLII. Subsequent deprotonation and reaction with a Weinreb amide gives acylbenzothiazoles XLIII. These intermediates can be brominated, with for instance, phenyltrimethylammonium tribromide, to give bromoketones XLIV. These intermediates can be converted to compounds of the invention using chemistry shown in Scheme 1, followed by derivatization of the aryl bromide using methods known to one skilled in the art.

Scheme 8

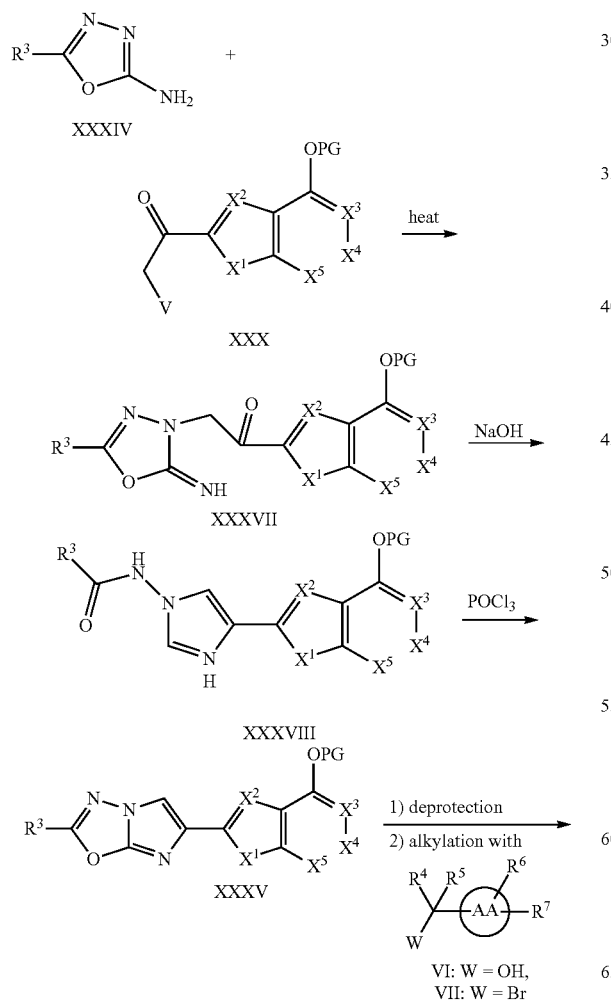

Scheme 9

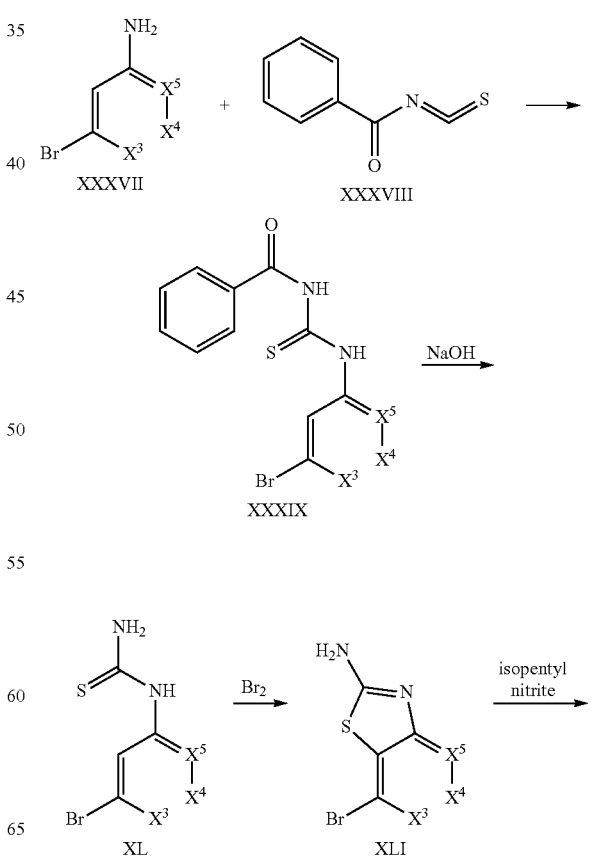

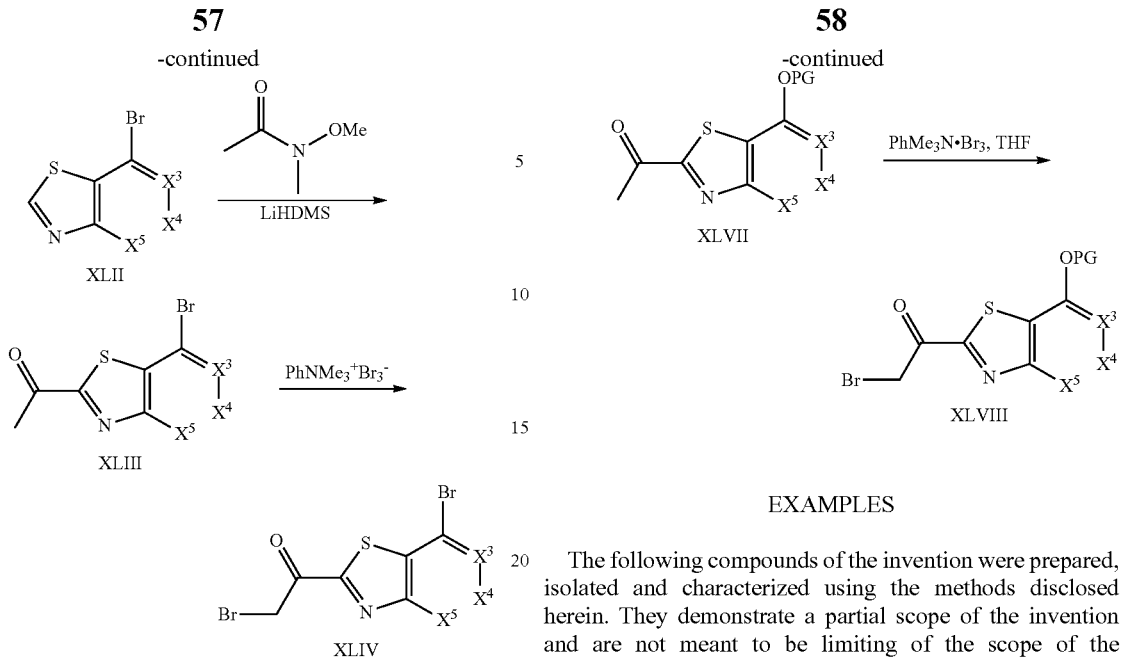

Benzothiazole compounds of the invention can also be prepared with intermediates shown in Scheme 10. Bromobenzothiazoles XLII, prepared as shown in Scheme 9, can be converted to a boronate and oxidized to phenols XLV. Reaction with a protecting group containing a reactive halogen, such as benzyl bromide, in the presence of base, such as potassium carbonate, affords protected benzothiazole XLVI. Acylation of the benzothiazole 2-position using a Weinreb amide and strong base, and subsequent bromination gives bromoketones XLVIII, which can be converted to compounds of Formula I as shown in Scheme 1.

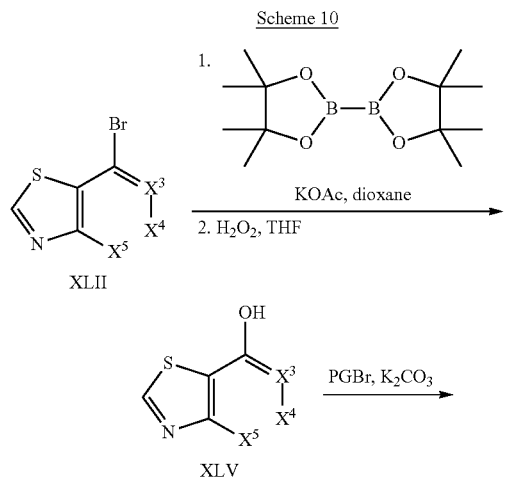

EXAMPLES

The following compounds of the invention were prepared, isolated and characterized using the methods disclosed herein. They demonstrate a partial scope of the invention and are not meant to be limiting of the scope of the invention. In the experimental procedures, solution ratios express a volume relationship, unless stated otherwise. NMR chemical shifts (δ) are reported in parts per million (ppm). Products were analyzed by reverse phase analytical HPLC using the following methods:

Method A: Column Zorbax® XDB-C18 3.5 microns, 4.6×30 mm eluted at 3 ml/min; 2 min gradient from 100% A to 100% B; Mobile phase: A=MeOH:H₂O:TFA (5:95:0.05), B=MeOH:H₂O:TFA (95:5:0.05).

Method B: Column Phenomenex® Kinetex-C18 2.6 microns, 4.6×30 mm eluted at 2 ml/min; 1.5 min gradient from 100% A to 100% B; Mobile phase: A=MeOH:H₂O:TFA (5:95:0.05), B=MeOH:H₂O:TFA (95:5:0.05).

Method C: Column Zorbax® SB-Phenyl, 3.5 microns, 4.6×50 mm eluted at 3 ml/min; 2 min gradient from 100% A to 100% B; Mobile phase: A=MeOH:H₂O:TFA (5:95:0.05), B=MeOH:H₂O:TFA (95:5:0.05).

Method D: Sunfire C18 3.5 micron column (4.6×30 mm) eluted at 3 mL/min with a 2 min. gradient from 100% A to 100% B (A: 5% methanol, 94.95% water, 0.05% TFA; B: 5% water, 94.95% methanol, 0.05% TFA, UV 220 nm).

Method E: Eclipse XDB-C18 3.5 micron column (4.6×30 mm) eluted at 3 mL/min with a 2 min gradient from 100% A to 100% B (A: 5% methanol, 94.95% water, 0.05% TFA; B: 5% water, 94.95% methanol, 0.05% TFA, UV 220 nm).

Method F: Eclipse XDB-C18 3.5 micron column (4.6×30 mm) eluted at 3 mL/min with a 2 min gradient from 100% A to 100% B (A: 5% acetonitrile, 94.95% water, 0.05% TFA; B: 5% water, 94.95% acetonitrile, 0.05% TFA, UV 220 nm).

Intermediate 1. 6-Methoxy-2-(2-methoxyimidazo[2,1-b][1,3,4]thiadiazol-6-yl)benzofuran-4-ol

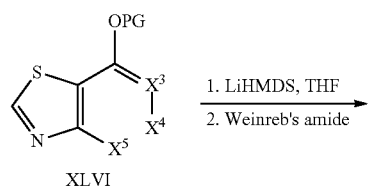

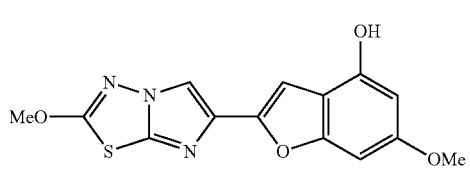

Intermediate 1A. 5-(Benzyloxy)-7-methoxy-2,2-dimethyl-4H-benzo[d][1,3]dioxin-4-one

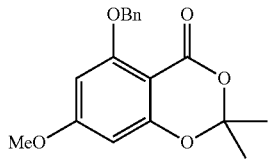

A solution of 5-hydroxy-7-methoxy-2,2-dimethyl-4H-benzo[d][1,3]dioxin-4-one (30.00 g, 0.134 mol, see Kamisuki, S. et al. Tetrahedron 2004, 60, 5695-5700 for preparation) in N,N-dimethylformamide (400 mL) was treated with powdered anhydrous potassium carbonate (19.41 g, 0.14 mol) added all at once. The resulting mixture was stirred in vacuo for 10 min. and then flushed with nitrogen. The reaction flask was placed in a water bath (22° C.) and treated with benzyl bromide (24.03 g, 0.14 mol) added dropwise over 15 min. The resulting mixture was then stirred at 22° C. for 18 h (no starting material left by tlc). The solid was filtered and washed with N,N-dimethylformamide. The filtrate was evaporated in vacuo and the residual oil was diluted with ethyl acetate (500 mL), washed with cold 0.1 N hydrochloric acid, saturated sodium bicarbonate and brine. After drying over anhydrous magnesium sulfate, evaporation of the solvent gave a thick syrup. Crystallization form ethyl acetate (50 mL) and hexane (150 mL) gave 35.17 g of 5-(benzyloxy)-7-methoxy-2,2-dimethyl-4H-benzo[d][1,3]dioxin-4-one as large colorless prisms. Chromatography of the mother liquors on silica gel (4×13 cm, elution toluene-ethyl acetate 0-5%) gave 6.64 g of additional material to afford a total yield of 41.81 g (99%). HRMS (ESI) calcd for $C_{18}H_{19}O_5[M+H]^+$ m/z 315.1227, found 315.1386. $^1$H NMR (CDCl$_3$, 600 MHz) δ 1.68 (s, 6H), 3.77 (s, 3H), 5.19 (s, 2H), 5.19 (s, 2H), 6.04 (d, J=2.03 Hz, 1H), 6.15 (d, J=2.03 Hz, 1H), 7.27 (broad t, 1H), 7.36 (broad t, 2H), 7.52 (broad d, 2H).

Intermediate 1B. 2-(Benzyloxy)-6-hydroxy-4-methoxybenzaldehyde

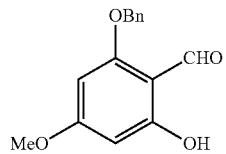

A solution of 5-(benzyloxy)-7-methoxy-2,2-dimethyl-4H-benzo[d][1,3]dioxin-4-one (Intermediate 1A, 6.76 g, 21.5 mmol) in dichloromethane (120 mL) was cooled to −78° C. and treated with 43 mL (64.5 mmol) of a 1.5 M solution of diisobutylaluminum hydride in toluene added dropwise over 20 min. The resulting mixture was then stirred at −78° C. for 3 h. The reaction mixture was quenched by the careful addition of methanol (5 mL) added dropwise over 15 min, followed by 1N hydrochloric acid (50 mL) added dropwise over 15 min. The cooling bath was then removed and an additional 150 mL of 1N hydrochloric acid was added over 20 min. The mixture was then stirred at 22° C. for 2 h and diluted with dichloromethane (400 mL). The organic phase was collected and the aqueous phase (pH~1) was extracted with dichloromethane (3×50 mL). The combined organic extracts were washed with brine, dried over anhydrous magnesium sulfate and concentrated in vacuo. The residual oil was diluted with tetrahydrofuran (70 mL), treated with 10 mL of 0.1N hydrochloric acid and stirred at 20° C. for 2 h. The reaction mixture was diluted with ethyl acetate (300 mL), washed with brine, dried over anhydrous magnesium sulfate, evaporated in vacuo to give a clear oil. Chromatography on silica gel (4×13 cm, elution toluene) gave 4.08 g (73% yield) of the title aldehyde as a clear oil which solidified on standing. LC (Method D): 2.237 min. HRMS (ESI) calcd for $C_{15}H_{15}O_4$ [M+H]$^+$ m/z 259.0965, found 259.1153. $^1$H NMR (CDCl$_3$, 600 MHz) δ 3.80 (s, 3H), 5.07 (s, 2H), 5.97 (d, J=2.1 Hz, 1H), 6.01 (d, J=2.1 Hz, 1H), 7.3-7.4 (m, 5H), 10.15 (s, 1H), 12.49 (s, 1H).

Intermediate 1C. 1-(4-(Benzyloxy)-6-methoxybenzofuran-2-yl)ethanone

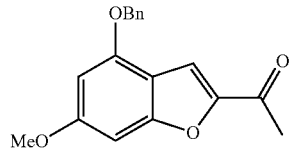 [SMILES: COc1cc(OCc2ccccc2)c2cc(C(C)=O)oc2c1]

A solution of 2-(benzyloxy)-6-hydroxy-4-methoxybenzaldehyde (Intermediate 1B, 3.46 g, 13.4 mmol) in N,N-dimethylformamide (50 mL) was treated with powdered anhydrous cesium carbonate (4.58 g, 14.05 mmol) added all at once. The resulting mixture was stirred in vacuo for 10 min. and then flushed with nitrogen. The reaction flask was placed in a water bath (22° C.) and treated with chloroacetone (1.74 g, 18.7 mmol) added dropwise over 5 min. The resulting mixture was then stirred at 22° C. for 18 h (no starting aldehyde left by tlc and formation of the intermediate alkylated aldehyde). The solid was filtered and washed with N,N-dimethylformamide. The filtrate was evaporated in vacuo and the residual oil was diluted with ethyl acetate (300 mL), washed with cold 0.1 N hydrochloric acid, saturated sodium bicarbonate and brine. After drying over anhydrous magnesium sulfate, evaporation of the solvent gave a thick syrup. This syrup was diluted with tetrahydrofuran (50 mL) and ethyl acetate (50 mL), treated p-toluenesulfonic acid monohydrate (0.2 g) and stirred at 20° C. for 1 h (tlc indicated complete cyclization of the intermediate alkylated aldehyde to the benzofuran). The reaction mixture was diluted with ethyl acetate (300 mL), washed with saturated sodium bicarbonate and brine. After drying over anhydrous magnesium sulfate, evaporation of the solvent gave a thick syrup. Chromatography on silica gel (4×12 cm, elution toluene-ethyl acetate 2-4%) gave 3.51 g (88% yield) of the title benzofuran as a yellow solid. Recrystallization from ethyl acetate (10 mL) and hexane (20 mL) gave the title material as large yellow prisms (3.15 g). LC (Method E): 2.148 min. HRMS (ESI) calcd for $C_{18}H_{17}O_4$ [M+H]$^+$ m/z 297.1121, found 297.1092. $^1$H NMR (CDCl$_3$, 600 MHz) δ 2.51 (s, 3H), 3.82 (s, 3H), 5.13 (s, 2H), 6.37 (d, J=1.77 Hz, 1H), 6.63 (broad s, 1H), 7.34 (broad t, 1H), 7.39 (broad t, 2H), 7.44 (broad d, 2H), 7.55 (d, J=0.7 Hz, 1H).

Intermediate 1D. 1-(4-(Benzyloxy)-6-methoxybenzofuran-2-yl)-2-bromoethanone

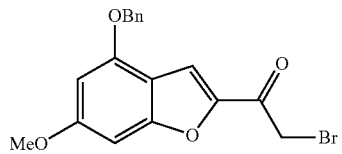 [SMILES: COc1cc(OCc2ccccc2)c2cc(C(=O)CBr)oc2c1]

A 250-mL, three-necked flask is equipped with a magnetic stirring bar and purged with a nitrogen atmosphere was charged with anhydrous tetrahydrofuran (25 mL) followed by 9.3 mL (9.3 mmol) of a 1M solution of lithium bis(trimethylsilyl)amide in tetrahydrofuran. The mixture was cooled to −78° C. and treated with a solution of 1-(4-(benzyloxy)-6-methoxybenzofuran-2-yl)ethanone (Intermediate IC, 2.40 g, 8.1 mmole) in tetrahydrofuran (20 mL) added dropwise over 10 min. The resulting mixture was then stirred at −78° C. for 45 min. Then chlorotrimethylsilane (1.18 mL, 9.31 mmol) was added dropwise over 5 min and the resulting solution was stirred at −78° C. for another 20 min. The cooling bath was then removed and the mixture is allowed to warm to room temperature over 30 min. The reaction mixture was then quenched by addition to a cold solution of ethyl acetate (200 mL), saturated sodium bicarbonate (30 mL) and ice. The organic phase was rapidly dried over anhydrous magnesium sulfate (magnetic stirring) and evaporated in vacuo to give the silyl enol ether as an oil which is co-evaporated with toluene (20 mL). The silyl enol ether was then dissolved in dry tetrahydrofuran (40 mL), cooled to −20° C. and treated with solid sodium bicarbonate (0.10 g) followed by N-bromosuccinimide (1.44 g, 8.1 mmol) added in small portions over 15 min. The reaction mixture was allowed to warm to 0° C. over 2 h and then quenched by addition of ethyl acetate (300 mL) and saturated sodium bicarbonate. The organic phase was washed with brine, dried over anhydrous magnesium sulfate and evaporated to give an orange oil. Chromatography on silica gel (4×12 cm, elution toluene-ethyl acetate 0-5%) gave 2.62 g (86% yield) of the title bromomethylketone as a yellow solid. Recrystallization from ethyl acetate (10 mL) and hexane (20 mL) gave yellow prisms (2.30 g). LC (Method F): 1.977 min. HRMS (ESI) calcd for $C_{18}H_{16}BrO_4$ [M+H]$^+$ m/z 375.0226, found 375.0277. $^1$H NMR (CDCl$_3$, 600 MHz) δ 3.84 (s, 3H), 4.33 (s, 2H), 5.14 (s, 2H), 6.38 (d, J=1.76 Hz, 1H), 6.64 (broad s, 1H), 7.35 (broad t, 1H), 7.40 (broad t, 2H), 7.44 (broad d, 2H), 7.70 (s, 1H).

Intermediate 1E. 6-(4-(Benzyloxy)-6-methoxybenzofuran-2-yl)-2-bromoimidazo[2,1-b][1,3,4]thiadiazole

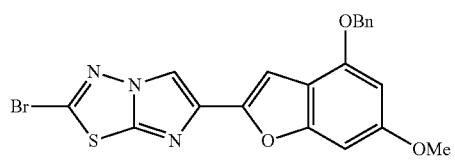 [SMILES: COc1cc(OCc2ccccc2)c2cc(-c3cn4nc(Br)sc4n3)oc2c1]

A mixture of 1-(4-(benzyloxy)-6-methoxybenzofuran-2-yl)-2-bromoethanone (Intermediate ID, 3.00 g, 8.0 mmol) and 5-bromo-1,3,4-thiadiazol-2-amine (1.65 g, 9.16 mmol) in isopropanol (100 mL) was heated in a pressure flask equipped with a magnetic stirring bar at 78-80° C. for 18 h (homogeneous after 20 min and then formation of a precipitate after 2 h). The cooled mixture is then transferred into five 20 mL microwave vials and then heated in a microwave apparatus to 150° C. for 30 min. Each vial was then diluted with dichloromethane (250 mL) washed with saturated sodium bicarbonate (25 mL) and brine (25 mL), dried over anhydrous magnesium sulfate. The fractions were combined and concentrated in vacuo. Chromatography of the orange-brown residual solid on silica gel (4×10 cm, slow elution with dichloromethane due to poor solubility) gave 2.96 g of the title imidazothiadiazole contaminated with some 1-(4-(benzyloxy)-6-methoxybenzofuran-2-yl)ethanone. The solid material was triturated with ethyl acetate (20 mL), filtered, washed with ethyl acetate (10 ml) and dried in vacuo to give 2.34 g (64% yield) of pure title imidazothiadiazole as an off white solid which is used as such for the next step. LC (Method F): 2.188 min. HRMS (ESI) calcd for $C_{20}H_{15}BrN_3O_3S$ [M+H]$^+$ m/z 456.00175, found 456.00397. $^1$H NMR (CDCl$_3$, 600 MHz) δ 3.82 (s, 3H), 5.16 (s, 2H), 6.38 (d, J=1.67 Hz, 1H), 6.66 (broad s, 1H), 7.15 (s, 1H), 7.31 (broad t, 1H), 7.38 (broad t, 2H), 7.45 (broad d, 2H), 8.02 (s, 1H).

Intermediate 1F. 6-(4-(Benzyloxy)-6-methoxybenzofuran-2-yl)-2-methoxyimidazo[2,1-b][1,3,4]thiadiazole

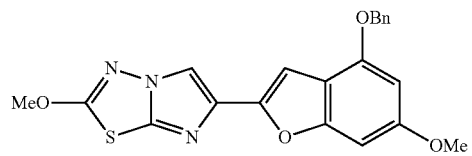 [SMILES: COc1cc(OCc2ccccc2)c2cc(-c3cn4nc(OC)sc4n3)oc2c1]

A solution of 6-(4-(benzyloxy)-6-methoxybenzofuran-2-yl)-2-bromoimidazo[2,1-b][1,3,4]thiadiazole (Intermediate 1E, 2.30 g, 5.04 mmol) in a mixture of dichloromethane (180 mL) and methanol (45 mL) was treated at 22° C. with 4.2 mL of a 25 wt. % solution of sodium methoxide in methanol (0.2 mmol) added in one portion. More methanol (45 mL) was added and the mixture was stirred for 1 h. The reaction mixture was quenched by the addition of 25 mL of 1N hydrochloric acid followed by 20 ml of saturated sodium bicarbonate. The solvent was evaporated under reduced pressure and the residue was diluted with dichloromethane (400 mL), washed with brine, dried over anhydrous magnesium sulfate and evaporated in vacuo. Chromatography of the residue on silica gel (3×10 cm, elution with dichloromethane-ethyl acetate 0-4%) gave 1.70 g (83% yield) of the title compound as a white solid. This material was recrystallized from ethyl acetate (30 mL per gram, 80% recovery) to give white needles. LC (Method E): 2.293 min. HRMS (ESI) calcd for $C_{21}H_{18}N_3O_4S$ [M+H]$^+$ m/z 408.1013, found 408.1024. $^1$H NMR (CDCl$_3$, 600 MHz) δ 3.81 (s, 3H), 4.18 (s, 3H), 5.16 (s, 2H), 6.37 (d, J=1.75 Hz, 1H), 6.67 (broad s, 1H), 7.07 (s, 1H), 7.31 (broad t, 1H), 7.37 (broad t, 2H), 7.45 (broad d, 2H), 7.81 (s, 1H).

Intermediate 1. 6-Methoxy-2-(2-methoxyimidazo[2,1-b][1,3,4]thiadiazol-6-yl)benzofuran-4-ol

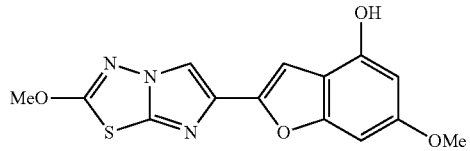 [SMILES: COc1cc(O)c2cc(-c3cn4nc(OC)sc4n3)oc2c1]

A mixture of 6-(4-(benzyloxy)-6-methoxybenzofuran-2-yl)-2-methoxyimidazo[2,1-b][1,3,4]thiadiazole (Intermediate 1F, 1.250 g, 3.06 mmol) and pentamethylbenzene (3.17 g, 21.4 mmol) in dichloromethane (200 mL) was cooled to −78° C. under a nitrogen atmosphere and then treated immediately (to avoid crystallization) with 8 mL (8 mmol) of a 1 M solution of boron trichloride in dichloromethane added dropwise over 3 min. The resulting mixture was stirred at −78° C. for 1 h. The reaction mixture was then quenched by the addition of a solution of sodium bicarbonate (6 g) in water (100 mL) added in one portion. The cooling bath was removed and the resulting mixture was stirred at room temperature for 1 h. The solid formed was filtered, washed successively with water (50 m) and dichloromethane (50 mL). The filter cake was allowed to soak with anhydrous ethanol (15 ml) and then sucked dry. The white solid obtained was then dried under vacuum for 24 h to give 0.788 g (80% yield) of pure title material (>95% by hplc). The combined filtrate and washings were diluted with dichloromethane (600 mL) and stirred in a warm water bath till the organic phase was clear with no apparent solid in suspension. The organic phase was collected, dried over anhydrous magnesium sulfate and rapidly filtered while still warm. The filtrate was evaporated and the residue (product and pentamethylbenzene) was triturated with toluene (20 mL), the solid collected and washed with toluene (20 mL) to give 0.186 g (19% yield, 99% combined yield) of title material as a tan solid (>95% by hplc). LC (Method F): 1.444 min. HRMS (ESI) calcd for $C_{14}H_{12}N_3O_4S$ $[M+H]^+$ m/z 318.0543, found 318.0578. $^1H$ NMR (DMSO-$d_6$, 600 MHz) δ 3.71 (s, 3H), 4.16 (s, 3H), 6.21 (d, J=1.87 Hz, 1H), 6.61 (broad s, 1H), 6.95 (s, 1H), 8.29 (s, 1H), 9.96 (s, 1H).

Intermediate 2. 6-Methoxy-2-(6-methylimidazo[1,2-b]pyridazin-2-yl)benzofuran-4-ol

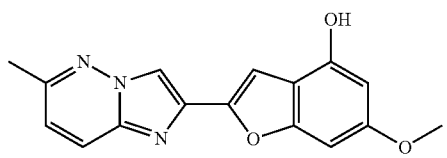

Intermediate 2A. 2-(4-(Benzyloxy)-6-methoxybenzofuran-2-yl)-6-methylimidazo[1,2-b]pyridazine

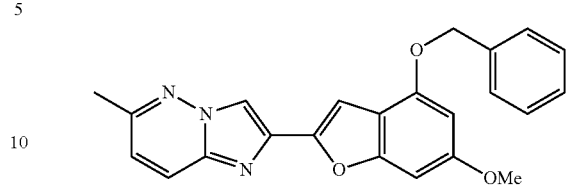

A mixture of 6-methylpyridazin-3-amine (1.52 g, 13.93 mmol), 1-(4-(benzyloxy)-6-methoxybenzofuran-2-yl)-2-bromoethanone (Intermediate 1D, 5.00 g, 13.33 mmol) and 2-propanol (110 mL) in a 150 mL pressure flask was heated at 65° C. The mixture was almost homogeneous after 30 min of heating and precipitated again after 40 min. The mixture was heated for a total of 48 h. The cooled reaction mixture was diluted with dichloromethane (600 mL), washed with saturated sodium bicarbonate, brine and dried over anhydrous magnesium sulfate. Evaporation gave an orange brown solid which was chromatographed on silica gel (4×9 cm, elution dichloromethane-ethyl acetate 0-5%) to give the title material (3.64 g) as an orange brown solid. The solid was boiled with ethyl acetate (30 mL, partially soluble) and allowed to stand at room temperature for 2 h. The crystals were collected by filtration and dried overnight in vacuo to give the title material (3.440 g, 67%) as pale yellow brown needles. LC (Method A): 2.279 min. HRMS (ESI) calcd for $C_{23}H_{20}N_3O_3$ $[M+H]^+$ m/z 386.1505, found 386.1532. $^1H$ NMR (CDCl$_3$, 400 MHz) δ ppm: 2.59 (s, 3H), 3.86 (s, 3H), 5.21 (s, 2H), 6.43 (d, J=1.96 Hz, 1H), 6.75 (broad d, 1H), 6.94 (d, J=9.39 Hz, 1H), 7.31-7.38 (m, 2H), 7.38-7.45 (m, 2H), 7.50 (broad d, J=7.43 Hz, 2H), 7.82 (d, J=9.39 Hz, 1H), 8.19 (s, 1H).

Intermediate 2. 6-Methoxy-2-(6-methylimidazo[1,2-b]pyridazin-2-yl)benzofuran-4-ol

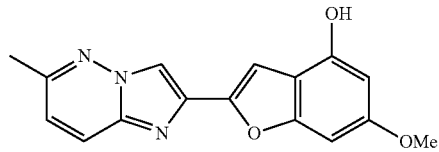 [SMILES: COc1cc(O)c2cc(-c3cn4nc(C)ccc4n3)oc2c1]

A solution of 2-(4-(benzyloxy)-6-methoxybenzofuran-2-yl)-6-methylimidazo[1,2-b]pyridazine (Intermediate 2A, 1.00 g, 2.59 mmol) in a mixture of dichloromethane (420 mL) and methanol (150 mL) in a 1 L flask was hydrogenated over 10% Palladium over carbon (0.30 g, i.e., 30 mg Pd) and under 1 atm of hydrogen for 6 h. The reaction mixture was maintained under vacuum for 2 min and then flushed with nitrogen. The catalyst was filtered and washed with warm dichloromethane-methanol (8:2, 100 mL) and the combined filtrate was concentrated under reduced pressure. The yellow residue was boiled with 1,2-dichloroethane (30 mL) and allowed to stand at room temperature for 18 h. The solid was filtered (contains methanol by NMR) and dried in vacuo at 120° C. for 12 h to give the title material (0.760 g, 99% yield) of a yellow solid. LC (Method A): 1.844 min. $^1H$ NMR (DMSO-$d_6$, 400 MHz) δ ppm: 2.54 (s, 3H), 3.77 (s, 3H), 6.28 (d, J=1.96 Hz, 1H), 6.70 (dd, J=1.96, 1.17 Hz, 1H), 7.20 (d, J=9.39 Hz, 1H), 7.24 (d, J=0.78 Hz, 1H), 8.03 (d, J=9.78 Hz, 1H), 8.50 (s, 1H), 10.10 (br s, 1H).

The following general methods were used for the preparation of intermediate alcohols, which were used to prepare the subsequently described example compounds.

General Method 1: (R)-ethyl 4-(2-(hydroxymethyl)pyrrolidin-1-yl)benzoate

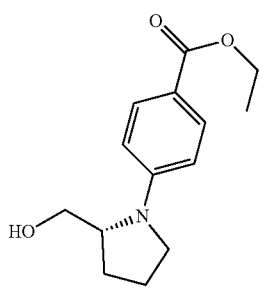 [SMILES: CCOC(=O)c1ccc(N2CCC[C@@H]2CO)cc1]

A 10 ml round-bottomed flask was charged with (R)-pyrrolidin-2-ylmethanol (0.11 ml, 1.115 mmol), ethyl 4-iodobenzoate (0.17 ml, 1.016 mmol), cesium carbonate (0.672 g, 2.062 mmol) and degassed DMF (1.5 ml). The flask was evacuated and backfilled with nitrogen three times. BINOL (0.144 g, 0.503 mmol) and copper(I) bromide (0.077 g, 0.537 mmol) were added and the mixture was stirred overnight at room temperature. The reaction mixture was diluted with ethyl acetate, washed with water, and the water layer was back extracted twice with ethyl acetate. Combined organic layers were washed once with saturated aqueous $NaHCO_3$ solution, once with water, once with brine, dried on anhydrous $Na_2SO_4$, filtrated and concentrated. The residue was purified on ISCO using a 40 g Innoflash® column (Hex/EtOAc) to give the title material (79 mg, 31%) as a colorless oil. LC (Method A): 1.966 min. MS (APCI) calcd for $C_{14}H_{20}NO_3$ $[M+H]^+$ m/z 250.14, found 250.2. $^1$H NMR (400 MHz, acetone-$d_6$) δ ppm 7.86-7.77 (m, 2H), 6.70-6.62 (m, 2H), 4.25 (q, J=7.0 Hz, 2H), 3.94-3.85 (m, 2H), 3.71-3.62 (m, 1H), 3.54-3.39 (m, 2H), 3.21 (dt, J=6.7, 9.4 Hz, 1H), 2.22-2.09 (m, 2H), 2.03-1.94 (m, 2H), 1.31 (t, J=7.0 Hz, 3H).

General Method 2: (R)-(1-(benzo[d][1,3]dioxol-5-yl)pyrrolidin-2-yl)methanol

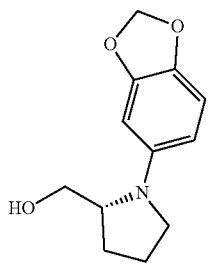 [SMILES: OC[C@H]1CCCN1c1ccc2c(c1)OCO2]

A 20 ml vial charged with 1-iodo-3,4-methylenedioxybenzene (0.13 ml, 1.001 mmol), (R)-pyrrolidin-2-ylmethanol (0.11 ml, 1.115 mmol), copper (I) iodide (0.153 g, 0.803 mmol) and 2-propanol (3.5 ml) was evacuated and backfilled with nitrogen four times and cooled at 0° C. in an ice-water bath. Powdered sodium hydroxide (0.081 g, 2.025 mmol) was then added and the mixture was stirred for 10 minutes at 0° C. (solution became purple) and 16 hours at 90° C. (solution became orange). The reaction mixture was cooled down to room temperature, diluted with ethyl acetate, washed with water, and the water layer was back extracted twice with ethyl acetate. Combined organic layers were washed once with saturated aqueous $NaHCO_3$ solution, once with water, once with brine, dried on anhydrous $Na_2SO_4$, filtrated and concentrated. The residue was purified on ISCO using a 25 g Innoflash® column (Hex/EtOAc) to give title material (0.166 g, 75%) as yellowish oil. LC (Method A): 0.886 min. MS (APCI) calcd for $C_{12}H_{16}NO_3$ $[M+H]^+$ m/z 222.11, found 222.2. $^1$H NMR (400 MHz, acetone-$d_6$) δ ppm 6.67 (d, J=8.2 Hz, 1H), 6.31 (d, J=2.3 Hz, 1H), 6.04 (dd, J=2.5, 8.4 Hz, 1H), 5.83 (d, J=1.2 Hz, 1H), 5.82 (d, J=0.8 Hz, 1H), 3.74 (t, J=5.7 Hz, 1H), 3.69-3.58 (m, 2H), 3.41-3.29 (m, 2H), 3.02 (dt, J=5.9, 9.0 Hz, 1H), 2.12-1.87 (m, 4H).

General Method 3: (S)-4-(2-(hydroxymethyl)pyrrolidin-1-yl)benzonitrile

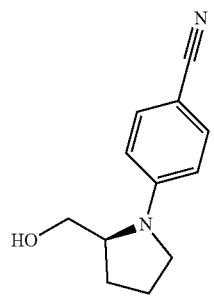 [SMILES: N#Cc1ccc(N2CCC[C@H]2CO)cc1]

A 20 ml vial charged with 4-bromobenzonitrile (0.183 g, 1.005 mmol), cesium carbonate (0.521 g, 1.599 mmol), BINAP (0.032 g, 0.051 mmol), palladium(II) acetate (0.023 g, 0.102 mmol) and (S)-pyrrolidin-2-ylmethanol (0.13 ml, 1.317 mmol) and 1,4-dioxane (4.5 ml) was evacuated and backfilled with nitrogen four times and the mixture was heated 18 hours at 80° C. The reaction mixture was cooled down to room temperature, diluted with ethyl acetate, washed with water, and the water layer was back extracted twice with ethyl acetate. Combined organic layers were washed twice with saturated aqueous $NaHCO_3$ solution, twice with water, once with brine, dried on anhydrous $Na_2SO_4$, filtrated and concentrated. The residue was purified on ISCO using a 25 g Innoflash® column (Hex/EtOAc) to give the title material (0.159 g, 78%) as a white solid. LC (Method A): 1.743 min. MS (APCI) calcd for $C_{12}H_{15}N_2O$ $[M+H]^+$ m/z 203.12, found 203.2. $^1$H NMR (400 MHz, acetone-$d_6$) δ ppm 7.50-7.42 (m, 2H), 6.77-6.67 (m, 2H), 3.96-3.85 (m, 2H), 3.69-3.60 (m, 1H), 3.54-3.40 (m, 2H), 3.27-3.16 (m, 1H), 2.20-2.10 (m, 2H), 2.04-1.95 (m, 2H).

General Method 4: (S)-(1-(p-tolyl)pyrrolidin-2-yl)methanol

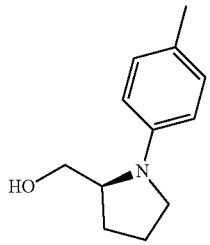

(S)-2-(((tert-butyldiphenylsilyl)oxy)methyl)pyrrolidine

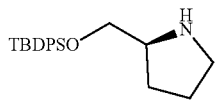

In a 100 ml round-bottomed flask under nitrogen at 0° C., TBDPS-Cl (4.1 ml, 15.96 mmol) was added to a solution of (S)-pyrrolidin-2-ylmethanol (0.75 ml, 7.60 mmol) and imidazole (1.295 g, 19.02 mmol) in dichloromethane (20 ml). The reaction mixture was stirred for 2 days at room temperature. A saturated aqueous NH$_4$Cl solution was added and the product was extracted three times with ethyl acetate. The combined organic layers were washed once with cold 1N aqueous NaOH solution, once with brine, dried over anhydrous Na$_2$SO$_4$, filtrated and concentrated. The residue was purified on ISCO using a 40 g Silicycle® column (CH$_2$Cl$_2$/MeOH) to give the title material (2.19 g, 85%) as beige creamy compound. LC (Method A): 2.151 min. MS (APCI) calcd for C$_{21}$H$_{30}$NOSi [M+H]$^+$ m/z 340.21, found 340.2. $^1$H NMR (400 MHz, CDCl$_3$) δ ppm 7.72-7.64 (m, 4H), 7.47-7.35 (m, 6H), 4.00 (br. s., 1H), 3.71 (dd, J=4.7, 10.2 Hz, 1H), 3.64 (dd, J=5.9, 10.2 Hz, 1H), 3.40-3.29 (m, 1H), 3.10-3.01 (m, 1H), 3.01-2.91 (m, 1H), 1.90-1.72 (m, 3H), 1.61-1.49 (m, 1H), 1.07 (s, 9H).

(S)-2-(((tert-butyldiphenylsilyl)oxy)methyl)-1-(p-tolyl)pyrrolidine

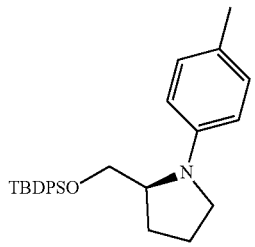

In a 10-20 ml microwaves vial, 4-bromotoluene (0.026 ml, 0.211 mmol), RuPhos (11 mg, 0.024 mmol) and RuPhos Palladacycle (19 mg, 0.023 mmol) were added to a solution of (S)-2-(((tert-butyldiphenylsilyl)oxy)methyl)pyrrolidine (79 mg, 0.233 mmol) in 1,4-dioxane (3 ml). The vial was evacuated and backfilled with nitrogen three times before addition of sodium tert-butoxide (33 mg, 0.343 mmol) and the mixture was heated 30 minutes at 140° C. in microwaves. Water was added to the reaction mixture and the product was extracted three times with ethyl acetate. Combined organic layers were washed once with saturated aqueous NaHCO$_3$ solution, once with brine, dried on anhydrous Na$_2$SO$_4$, filtrated and concentrated. The residue was purified on ISCO using a 12 g Innoflash® column (Hex/EtOAc) to give 70% pure title material (53 mg, 41%) as a yellowish oil that was repurified after TBDPS deprotection. LC (Method A): 2.649 min. MS (APCI) calcd for C$_{28}$H$_{36}$NOSi [M+H]$^+$ m/z 430.26, found 430.2.

(S)-(1-(p-tolyl)pyrrolidin-2-yl)methanol

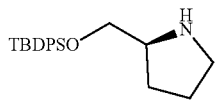

TBAF, 75% in water (0.09 ml, 0.246 mmol), was added dropwise to a 0° C. solution of (S)-2-(((tert-butyldiphenylsilyl)oxy)methyl)-1-(p-tolyl)pyrrolidine (0.037 g, 0.086 mmol) in THF (2 ml) in a 10 ml round-bottomed flask. The mixture was stirred 1 hour at room temperature. Water was added to the mixture and the compound was extracted three times with ethyl acetate. Combined organic layers were washed with brine, dried on anhydrous Na$_2$SO$_4$, filtrated and concentrated. The residue was purified on ISCO using a 12 g Innoflash® column (Hex/EtOAc) to give the title material (14 mg, 85%) as white solid. LC (Method A): 1.094 min. MS (APCI) calcd for C$_{12}$H$_{18}$NO [M+H]+ m/z 192.14, found 192.2. $^1$H NMR (400 MHz, acetone-d$_6$) δ ppm 6.99-6.93 (m, 2H), 6.57-6.50 (m, 2H), 3.76-3.60 (m, 3H), 3.43-3.30 (m, 2H), 3.08-2.98 (m, 1H), 2.18 (s, 3H), 2.13-2.06 (m, 1H), 2.02-1.87 (m, 3H).

General method 5: (R)-1-(4-fluorophenyl)-5-(hydroxymethyl)pyrrolidin-2-one

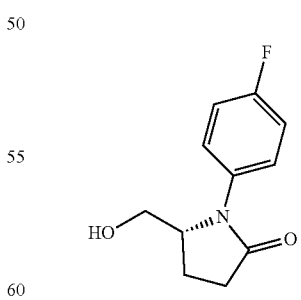

In a 20 ml vial, a mixture of (R)-5-(hydroxymethyl)pyrrolidin-2-one (70 mg, 0.608 mmol), 1-fluoro-4-iodobenzene (0.060 ml, 0.520 mmol) and potassium carbonate (144 mg, 1.042 mmol) in degassed acetonitrile (4 ml) was evacuated and backfilled with nitrogen three times. Copper (I) iodide (21 mg, 0.110 mmol) and N,N-dimethylethylenediamine (0.022 ml, 0.204 mmol) were added and the mixture was stirred 2 days at 85° C. The mixture was diluted in ethyl acetate, filtered on Celite® and concentrated. The residue was triturated once with hexanes and was purified on ISCO using a 12 g Innoflash® column (CH$_2$C$_{12}$/EtOAc) to give the title material (26 mg, 24%) as a beige solid. LC (Method A): 1.135 min. MS (APCI) calcd for C$_{11}$H$_{13}$FNO$_2$ [M+H]+ m/z 210.09, found 210.2. $^1$H NMR (400 MHz, methanol-d$_4$) δ ppm 7.46-7.38 (m, 2H), 7.19-7.11 (m, 2H), 4.30-4.21 (m, 1H), 3.61-3.48 (m, 2H), 2.68 (ddd, J=7.6, 9.9, 17.3 Hz, 1H), 2.49 (ddd, J=4.7, 10.5, 16.9 Hz, 1H), 2.41-2.27 (m, 1H), 2.22-2.09 (m, 1H).

General Method 6: 2-(3-(hydroxymethyl)piperidin-1-yl)isonicotinonitrile

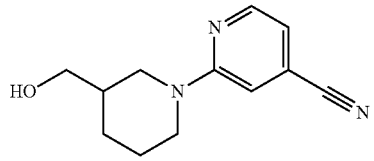 [SMILES: N#Cc1ccnc(N2CCCC(CO)C2)c1]

To an oven dried 15 ml Schlenck tube, under N$_2$, was added piperidin-3-ylmethanol (232 mg, 2.014 mmol), 2-chloroisonicotinonitrile (169 mg, 1.220 mmol), potassium carbonate (173 mg, 1.252 mmol) and DMSO (2 ml). The tube was capped with a rubber septum and was evacuated and backfilled with nitrogen four times. The mixture was heated at 80° C. (bath temp.) for 2 hours; the reaction progression being monitored by HPLC. The reaction mixture was diluted with ethyl acetate (60 ml), washed with water (30 ml), brine (30 ml) and dried (MgSO4). The residue was purified on ISCO using a 24 g Innoflash® column (hexanes/EtOAc) to give the title material (222 mg, 84%). LC (Method C): 1.381 min. MS (APCI) calcd for C$_{12}$H$_{16}$N$_3$O [M+H]+ m/z 218.1288 found 218.1300. $^1$H NMR (400 MHz, CDCl$_3$) δ ppm 8.26 (dd, J=5.1, 0.8 Hz, 1H), 7.01-7.18 (m, 1H), 6.78 (dd, J=5.1, 1.2 Hz, 1H), 4.39 (ddt, J=13.3, 3.7, 1.7 Hz, 1H), 4.21-4.32 (m, 1H), 3.62-3.72 (m, 1H), 3.39-3.57 (m, 2H), 3.01 (ddd, J=13.3, 11.3, 3.1 Hz, 1H), 2.73-2.87 (m, 2H), 1.80-1.94 (m, 1H), 1.66-1.80 (m, 2H), 1.44-1.61 (m, 1H), 1.26-1.41 (m, 1H)

General Method 7: tert-butyl 3-(hydroxymethyl)piperidine-1-carboxylate

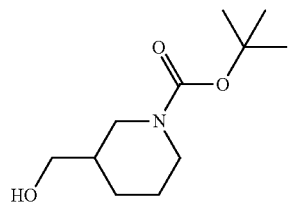

To a solution of piperidin-3-ylmethanol (350 mg, 3.04 mmol) and triethylamine (0.44 ml, 3.16 mmol) in dichloromethane (4 ml) was added dropwise a solution of di-tert-butyl dicarbonate (700 mg, 3.21 mmol) in dichloromethane (4 ml). The mixture was stirred at room temperature for 2 days. The solvent was evaporated and the residue was taken up in ethyl acetate (75 ml), washed with 1N aqueous HCl (30 ml), water (2×30 ml), brine (30 ml) and dried (MgSO4). Evaporation of the solvent gave the title material as an oil that crystallized when exposed to high vacuum; (623 mg, 2.89 mmol, 95%). MS (APCI) calcd for C$_{11}$H$_{22}$NO$_3$ [M+H]+ m/z 216.15 found 116.2. $^1$H NMR (400 MHz, acetone-d$_6$) δ ppm 4.05 (d, J=11.7 Hz, 1H), 3.88 (d, J=12.1 Hz, 1H), 3.54-3.62 (m, 1H), 3.30-3.50 (m, 2H), 2.58 (br. s., 1H), 1.71-1.83 (m, 1H), 1.52-1.69 (m, 2H), 1.30-1.47 (m, 10H), 1.11-1.29 ppm (m, 1H)

Preparation of Alcohols

The following alcohols were prepared according to the general methods described above, using the appropriate amines and aryl bromides or iodides. These alcohols were subsequently employed in preparing Example compounds as indicated.

| Structure | General Method | Formula [M + H]+ | Calc. [M + H]+ m/z | LCMS [M + H]+ m/z | HPLC RT (Min)/Method | NMR |
|---|---|---|---|---|---|---|
| (4-chlorophenyl pyrrolidinyl methanol) | 1 | C$_{11}$H$_{15}$ClNO | 212.08 | 212.2 | 1.849/A | $^1$H NMR (400 MHz, CDCl$_3$) δ ppm 7.22-7.12 (m, 2 H), 6.66-6.57 (m, 2 H), 3.88-3.77 (m, 1 H), 3.69-3.60 (m, 2 H), 3.53-3.44 (m, 1 H), 3.19-3.06 (m, 1 H), 2.14-1.95 (m, 4 H), 1.49 (t, J = 6.1 Hz, 1 H) |

| Structure | General Method | Formula [M + H]+ | Calc. [M + H]+ m/z | LCMS [M + H]+ m/z | HPLC RT (Min)/ Method | NMR |
|---|---|---|---|---|---|---|
| | 2 | C₁₂H₁₈NO₂ | 208.13 | 208.2 | 0.945/A | ¹H NMR (400 MHz, acetone-d₆) δ ppm 6.82-6.75 (m, 2 H), 6.63-6.55 (m, 2 H), 3.73-3.59 (m, 3 H), 3.69 (s, 3 H), 3.44-3.29 (m, 2 H), 3.07-2.95 (m, 1 H), 2.12-1.87 (m, 4 H) |
| | 2 | C₁₁H₁₅FNO | 196.11 | 196.2 | 1.011/A | ¹H NMR (400 MHz, acetone-d₆) δ ppm 6.97-6.87 (m, 2 H), 6.66-6.55 (m, 2 H), 3.77 (t, J = 5.8 Hz, 1 H), 3.70 (dt, J = 3.5, 7.2 Hz, 1 H), 3.63 (ddd, J = 3.5, 5.7, 10.8 Hz, 1 H), 3.46-3.32 (m, 2 H), 3.10-3.01 (m, 1 H), 2.14-1.90 (m, 4 H) |
| | 2 | C₁₂H₁₅N₂O | 203.12 | 203.2 | 1.731/A | ¹H NMR (400 MHz, acetone-d₆) δ ppm 7.50-7.42 (m, 2 H), 6.76-6.68 (m, 2 H), 3.95-3.87 (m, 2 H), 3.64 (ddd, J = 3.9, 5.5, 11.0 Hz, 1 H), 3.53-3.41 (m, 2 H), 3.26-3.16 (m, 1 H), 2.22-1.97 (m, 4 H) |
| 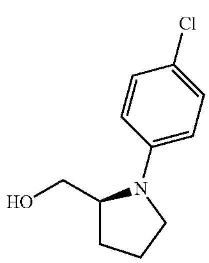 [SMILES: OC[C@@H]1CCCN1c1ccc(Cl)cc1] | 1 | C₁₁H₁₅ClNO | 212.08 | 212.2 | 1.852/A | ¹H NMR (400 MHz, CDCl₃) δ ppm 7.21-7.12 (m, 2 H), 6.68-6.56 (m, 2 H), 3.87-3.79 (m, 1 H), 3.70-3.61 (m, 2 H), 3.53-3.44 (m, 1 H), 3.18-3.07 (m, 1 H), 2.14-1.96 (m, 4 H), 1.49 (t, J = 6.1 Hz, 1 H) |
| | 2 | C₁₂H₁₈NO₂ | 208.13 | 208.2 | 0.956/A | ¹H NMR (400 MHz, acetone-d₆) δ ppm 6.82-6.75 (m, 2 H), 6.64-6.56 (m, 2 H), 3.72-3.60 (m, 3 H), 3.69 (s, 3 H), 3.43-3.31 (m, 2 H), 3.01 (dt, J = 6.3, 9.0 Hz, 1 H), 2.11-2.06 (m, 1 H), 2.03-1.99 (m, 1 H), 1.98-1.91 (m, 2 H) |

-continued

| Structure | General Method | Formula [M + H]+ | Calc. [M + H]+ m/z | LCMS [M + H]+ m/z | HPLC RT (Min)/ Method | NMR |
|---|---|---|---|---|---|---|
| (4-fluorophenyl pyrrolidinyl methanol) | 2 | C₁₁H₁₅FNO | 196.11 | 196.2 | 1.002/A | ¹H NMR (400 MHz, acetone-d₆) δ ppm 6.98-6.88 (m, 2 H), 6.65-6.56 (m, 2 H), 3.80-3.74 (m, 1 H), 3.70 (dt, J = 3.3, 7.3 Hz, 1 H), 3.67-3.58 (m, 1 H), 3.45-3.32 (m, 2 H), 3.10-3.00 (m, 1 H), 2.12-2.07 (m, 2 1-1), 2.03-1.90 (m, 2 H) |
| (3-methoxyphenyl pyrrolidinyl methanol) | 2 | C₁₂H₁₈NO₂ | 208.13 | 208.2 | 1.289/A | ¹H NMR (400 MHz, acetone-d₆) δ ppm 7.04 (t, J = 8.0 Hz, 1 H), 6.26-6.22 (m, 1 H), 6.22-6.18 (m, 1 H), 6.18-6.16 (m, 1 H), 3.80-3.70 (m, 2 H), 3.73 (s, 3 H), 3.69-3.62 (m, 1 H), 3.44-3.31 (m, 2 H), 3.08 (dt, J = 6.5, 9.3 Hz, 1 H), 2.15-2.06 (m, 2 H), 2.03-1.88 (m, 2 H) |
| (5-methoxypyridin-2-yl pyrrolidinyl methanol) | 3 | C₁₁H₁₇N₂O₂ | 209.13 | 209.2 | 0.974/A | ¹H NMR (400 MHz, acetone-d₆) δ ppm 7.79 (d, J = 3.1 Hz, 1 H), 7.23 (dd, J = 3.1, 9.0 Hz, 1 H), 6.49 (d, J = 9.0 Hz, 1 H), 4.10-3.99 (m, 1 H), 3.76 (s, 3 H), 3.59 (dd, J = 6.7, 10.6 Hz, 1 H), 3.54-3.42 (m, 2 H), 3.28-3.16 (m, 1 H), 2.03-1.84 (m, 4 H) |
| (benzo[d][1,3]dioxol-5-yl pyrrolidinyl methanol) | 2 | C₁₂H₁₆NO₃ | 222.11 | 222.2 | 0.895/A | ¹H NMR (400 MHz, acetone-d₆) δ ppm 6.67 (dd, J = 1.0, 8.4 Hz, 1 H), 6.31 (d, J = 1.2 Hz, 1 H), 6.05 (dd, J = 1.4, 8.4 Hz, 1 H), 5.86-5.79 (m, 2 H), 3.74 (t, J = 5.7 Hz, 1 H), 3.70-3.57 (m, 2 H), 3.43-3.28 (m, 2 H), 3.02 (dt, J = 5.9, 9.0 Hz, 1 H), 2.13-1.85 (m, 4H) |
| (4-trifluoromethylphenyl pyrrolidinyl methanol) | 2 | C₁₂H₁₅F₃NO | 246.11 | 246.2 | 2.086/A | ¹H NMR (400 MHz, acetone-d₆) δ ppm 7.48-7.41 (m, J = 9.0 Hz, 2 H), 6.77-6.71 (m, J = 9.0 Hz, 2 H), 3.92-3.84 (m, 2 H), 3.70-3.61 (m, 1 H), 3.52-3.39 (m, 2 H), 3.19 (dt, J = 6.7, 9.2 Hz, 1 H), 2.23-2.08 (m, 2 H), 2.03-1.92 (m, 2 H) |
| (4-trifluoromethoxyphenyl pyrrolidinyl methanol) | 2 | C₁₂H₁₅F₃NO₂ | 262.10 | 262.2 | 2.089/A | ¹H NMR (400 MHz, acetone-d₆) δ ppm 7.18-7.04 (m, 2 H), 6.71-6.61 (m, 2 H), 3.82 (t, J = 5.7 Hz, 1 H), 3.81-3.74 (m, 1 H), 3.68-3.58 (m, 1 H), 3.47-3.35 (m, 2 H), 3.11 (dt, J = 6.3, 9.2 Hz, 1 H), 2.16-2.07 (m, 2 H), 2.03-1.94 (m, 2 H) |

-continued

| Structure | General Method | Formula [M + H]+ | Calc. [M + H]+ m/z | LCMS [M + H]+ m/z | HPLC RT (Min)/ Method | NMR |
|---|---|---|---|---|---|---|
| HO—⟨pyrrolidine⟩—N—⟨C6H4⟩—Cl | 1 | C11H15ClNO | 212.08 | 212.2 | 1.926/A | 1H NMR (400 MHz, acetone-d6) δ ppm 7.17-7.10 (m, 2 H), 6.56-6.48 (m, 2 H), 3.79 (t, J = 5.3 Hz, 1 H), 3.65-3.51 (m, 2 H), 3.40-3.20 (m, 3 H), 3.09 (dd, J = 6.3, 9.4 Hz, 1 H), 2.53 (spt, J = 7.0 Hz, 1 H), 2.16-2.07 (m, 1 H), 1.92-1.76 (m, 1 H) |
| HO—⟨pyrrolidine⟩—N—⟨C6H4⟩—OMe | 1 | C12H18NO2 | 208.13 | 208.2 | 0.980/A | 1H NMR (400 MHz, acetone-d6) δ ppm 6.83-6.75 (m, 2 H), 6.55-6.46 (m, 2 H), 3.75-3.72 (m, 1 H), 3.69 (s, 3 H), 3.64-3.48 (m, 2 H), 3.36-3.13 (m, 3 H), 3.04 (dd, J = 6.3, 9.4 Hz, 1 H), 2.58-2.43 (m, 1 H), 2.13-2.07 (m, 1 H), 1.79 (qi, J = 7.3, 12.4 Hz, 1 H) |
| HO—⟨azetidine⟩—N—⟨C6H4⟩—F | 1 | C10H13FNO | 182.10 | 182.2 | 0.895/A | 1H NMR (400 MHz, acetone-d6) δ ppm 6.98-6.86 (m, 2 H), 6.45-6.34 (m, 2 H), 3.88-3.78 (m, 3 H), 3.78-3.70 (m, 2 H), 3.66-3.54 (m, 2 H), 2.90-2.73 (m, 1 H) |
| HO—⟨piperidine⟩—N—⟨C6H4⟩—CN | 1 | C13H17N2O | 217.13 | 217.2 | 1.925/C | 1H NMR (400 MHz, acetone-d6) δ ppm 7.50 (d, J = 9.0 Hz, 2 H), 7.01 (d, J = 9.0 Hz, 2 H), 3.94-4.04 (m, 1 H), 3.86 (dt, J = 12.9, 3.7 Hz, 1 H), 3.70 (t, J = 5.3 Hz, 1 H), 3.49-3.57 (m, 1 H), 3.40-3.49 (m, 1 H), 2.94 (ddd, J = 12.9, 11.5, 2.9 Hz, 1 H), 2.71-2.76 (m, 1 H), 1.71-1.87 (m, 3 H), 1.52-1.66 (m, 1 H), 1.21-1.37 (m, 1 H) |
| HO—⟨piperidine⟩—N—⟨C6H4⟩—CO2Et | 1 | C15H22NO3 | 264.15 | 264.2 | 1.940/C | 1H NMR (400 MHz, acetone-d6) δ ppm 7.80-7.87 (m, 2 H), 6.91-7.00 (m, 2 H), 4.26 (q, J = 7.3 Hz, 2 H), 3.99 (dt, J = 12.8, 1.8 Hz, 1 H), 3.84 (dt, J = 12.9, 3.7 Hz, 1 H), 3.65-3.71 (m, 1 H), 3.49-3.58 (m, 1 H), 3.40-3.49 (m, 1 H), 2.89 (ddd, J = 12.9, 11.5, 2.9 Hz, 1 H), 2.70 (dd, J = 12.7, 10.0 Hz, 1 H), 1.72-1.87 (m, 3 H), 1.53-1.67 (m, 1 H), 1.29-1.36 (m, 3 H), 1.19-1.29 (m, 1 H) |
| HO—⟨piperidine⟩—N—⟨C6H4⟩—CN | 1 | C13H17N2O | 217.13 | 217.2 | 1.892/C | 1H NMR (400 MHz, acetone-d6) δ ppm 7.50 (d, J = 9.4 Hz, 2 H), 7.01 (d, J = 9.0 Hz, 2 H), 3.99 (dt, J = 12.9, 2.0 Hz, 1 H), 3.86 (dt, J = 12.7, 3.8 Hz, 1 H), 3.67-3.72 (m, 1 H), 3.49-3.57 (m, 1 H), 3.41-3.49 (m, 1 H), 2.94 (ddd, J = 13.0, 11.4, 2.9 Hz, 1 H), 2.71-2.76 (m, 1 H), 1.72-1.87 (m, 3 H), 1.52-1.66 (m, 1 H), 1.22-1.36 (m, 1 H) |
| HO—⟨piperidine⟩—N—⟨C6H4⟩—CO2Et | 1 | C15H22NO3 | 264.15 | 264.2 | 1.970/C | 1H NMR (400 MHz, acetone-d6) δ ppm 7.84 (d, J = 9.0 Hz, 2 H), 6.95 (d, J = 9.0 Hz, 2 H), 4.26 (q, J = 7.3 Hz, 2 H), 3.94-4.02 (m, 1 H), 3.84 (dt, J = 12.8, 3.8 Hz, 1 H), 3.64-3.71 (m, 1 H), 3.49-3.58 (m, 1 H), 3.40-3.49 (m, 1 H), 2.89 (ddd, J = 12.6, 11.4, 2.9 Hz, 1 H), 2.70 (dd, J = 12.7, 10.0 Hz, 1 H), 1.71-1.87 (m, 3 H), 1.53-1.68 (m, 1 H), 1.32 (t, J = 7.2 Hz, 3 H), 1.22-1.28 (m, 1 H) |
| HO—⟨piperidine⟩—N—⟨pyridine⟩—OMe | 3 | C12H19N2O2 | 223.14 | | | 1H NMR (400 MHz, CDCl3) δ ppm 7.88 (d, J = 3.1 Hz, 1 H), 7.14 (dd, J = 9.0, 3.1 Hz, 1 H), 6.67 (d, J = 9.4 Hz, 1 H), 3.79 (s, 3 H), 3.65-3.78 (m, 2 H), 3.49-3.60 (m, 2 H), 3.29 (dd, J = 12.9, 7.0 Hz, 1 H), 3.17 (ddd, J = 12.5, 8.6, 3.5 Hz, 1 H), 1.79-1.97 (m, 2 H), 1.67-1.78 (m, 1 H), 1.57 (dtd, J = 13.0, 8.7, 4.1 Hz, 2 H), 1.30-1.41 (m, 1 H) |

-continued

| Structure | General Method | Formula [M + H]+ | Calc. [M + H]+ m/z | LCMS [M + H]+ m/z | HPLC RT (Min)/ Method | NMR |
|---|---|---|---|---|---|---|
| 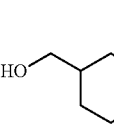 | 1 | C₁₂H₁₇ClNO | 226.09 | 226.2 | 1.314/C | ¹H NMR (400 MHz, CDCl₃) δ ppm 7.16-7.22 (m, 2 H), 6.84-6.91 (m, 2 H), 3.54-3.72 (m, 3 H), 3.50 (d, J = 12.1 Hz, 1 H), 2.69-2.81(m, 1 H), 2.58 (dd, J = 11.7, 9.8 Hz, 1 H), 1.87-2.00 (m, 1 H), 1.82 (dd, J = 11.2, 2.9 Hz, 2 H), 1.62-1.76 (m, 1 H), 1.39 (br. s., 1 H), 1.12-1.31 (m, 1 H) |
| 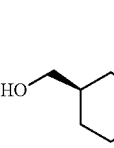 | 1 | C₁₂H₁₇ClNO | 226.09 | 226.2 | 1.296/C | ¹H NMR (400 MHz, CDCl₃) δ ppm 7.15-7.22 (m, 2 H), 6.83-6.91 (m, 2 H), 3.61-3.69 (m, 2 H), 3.53-3.61 (m, 1 H), 3.50 (d, J = 11.7 Hz, 1 H), 2.69-2.81 (m, 1 H), 2.53-2.64 (m, 1 H), 1.86-2.02 (m, 1 H), 1.77-1.86 (m, 2 H), 1.63-1.77 (m, 1 H), 1.39 (t, J = 4.9 Hz, 1 H), 1.11-1.26 (m, 1 H) |
| 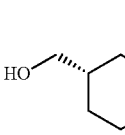 | 1 | C₁₂H₁₇ClNO | 226.09 | 226.2 | 1.323/C | |
| 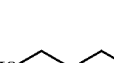 | 1 | C₁₃H₂₀NO₂ | 222.1489 | 222.1515 | 1.271/C | ¹H NMR (400 MHz, CDCl₃) δ ppm 6.91-6.98 (m, 2 H), 6.80-6.87 (m, 2 H), 3.78 (s, 3 H), 3.56-3.72 (m, 2 H), 3.51 (dd, J = 11.5, 3.7 Hz, 1 H), 3.31-3.40 (m, 1 H), 2.65-2.76 (m, 1 H), 2.54 (dd, J = 11.3, 9.4 Hz, 1 H), 1.95 (ddd, J = 9.9, 6.4, 3.3 Hz, 1 H), 1.67-1.90 (m, 3 H), 1.11-1.24 (m, 1 H) |
| 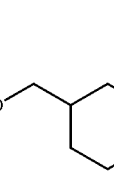 | 3 | C₁₁H₁₅F₂N₂O | 229.1147 | 229.1180 | 1.842/C | ¹H NMR (400 MHz, CDCl₃) δ ppm 7.91 (d, J = 2.3 Hz, 1 H), 7.10 (ddd, J = 11.8, 7.7, 2.7 Hz, 1 H), 3.56-3.75 (m, 4 H), 3.00-3.18 (m, 2H), 2.01-2.10 (m, 1 H), 1.95 (dt, J = 7.1, 3.3 Hz, 1 H), 1.71-1.91 (m, 2 H), 1.60-1.71 (m, 1 H), 1.25-1.40 (m, 1 H) |
| 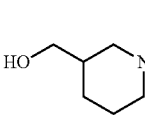 | 1 | C₁₃H₁₈NO₃ | 236.12 | 236.2 | 1.218/C | ¹H NMR (400 MHz, DMSO-d₆) δ ppm 6.74 (d, J = 8.6 Hz, 1 H), 6.61 (d, J = 2.3 Hz, 1 H), 6.32 (dd, J = 8.6, 2.3 Hz, 1 H), 5.89 (s, 2 H), 4.49 (t, J = 5.3 Hz, 1 H), 3.42-3.50 (m, 1 H), 3.33-3.42 (m, 1 H), 3.24-3.30 (m, 2 H), 2.52-2.58 (m, 1 H), 2.30 (dd, J = 11.7, 9.8 Hz, 1 H), 1.62-1.76 (m, 3 H), 1.45-1.61 (m, 1 H), 0.94-1.08 (m, 1 H) |
| 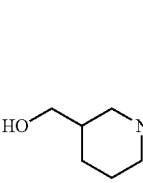 | 1 | C₁₃H₁₇F₃NO | 260.12 | 260.2 | 1.842/C | ¹H NMR (400 MHz, DMSO-d₆) δ ppm 7.40-7.52 (m, J = 9.0 Hz, 2 H), 6.95-7.07 (m, J = 9.0 Hz, 2 H), 4.56 (br. s., 1 H), 3.70-3.91 (m, 2 H), 3.20-3.45 (m, 4 H), 2.75-2.87 (m, 1 H), 2.59 (dd, J = 12.5, 10.2 Hz, 1 H), 1.60-1.79 (m, 2 H), 1.42-1.57 (m, 1 H), 1.08-1.22 (m, 1 H) |
| 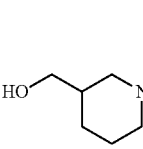 | 1 | C₁₃H₁₇N₂O | 217.13 | 217.2 | 1.920/C | ¹H NMR (400 MHz, DMSO-d₆) δ ppm 7.50-7.58 (m, 2 H), 6.93-7.01 (m, 2 H), 4.57 (t, J = 5.3 Hz, 1 H), 3.77-3.93 (m, 2 H), 3.32-3.38 (m, 1 H), 3.24-3.28 (m, 1 H), 2.87 (ddd, J = 12.9, 11.5, 2.9 Hz, 1 H), 2.67 (dd, J = 13.1, 10.4 Hz, 1 H), 1.57-1.78 (m, 3 H), 1.38-1.53 (m, 1 H), 1.12-1.26 (m, 1 H) |
| 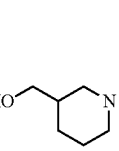 | 1 | C₁₅H₂₂NO₃ | 264.15 | 264.2 | 1.952/C | ¹H NMR (400 MHz, DMSO-d₆) δ ppm 7.71-7.80 (m, 2 H), 6.89-6.98 (m, 2 H), 4.57 (t, J = 5.3 Hz, 1 H), 4.23 (q, J = 7.0 Hz, 2 H), 3.75-3.94 (m, 2 H), 3.33-3.39 (m, 1 H), 3.23-3.28 (m, 1 H), 2.78-2.88 (m, 1 H), 2.62 (dd, J = 12.7, 10.4 Hz, 1 H), 1.59-1.78 (m, 3 H), 1.42-1.56 (m, 1 H), 1.28 (t, J = 7.0 Hz, 3 H), 1.10-1.23 (m, 1 H) |

-continued

| Structure | General Method | Formula [M + H]+ | Calc. [M + H]+ m/z | LCMS [M + H]+ m/z | HPLC RT (Min)/ Method | NMR |
|---|---|---|---|---|---|---|
| | 1 | $C_{14}H_{22}NO_3$ | 252.15 | 252.2 | 1.401/C | $^1$H NMR (400 MHz, DMSO-$d_6$) δ ppm 6.80 (d, J = 8.6 Hz, 1 H), 6.50 (d, J = 2.7 Hz, 1 H), 6.41 (dd, J = 8.6, 2.7 Hz, 1 H), 4.41 (t, J = 5.3 Hz, 1 H), 3.75 (s, 3 H), 3.69 (s, 3 H), 3.33-3.37 (m, 1 H), 3.27 (d, J = 6.3 Hz, 1 H), 3.19 (d, J = 8.2 Hz, 1 H), 3.11 (d, J = 11.0 Hz, 1 H), 2.36-2.45 (m, 1 H), 2.22 (t, J = 10.4 Hz, 1 H), 1.62-1.81 (m, 3 H), 1.49-1.62 (m, 1 H), 0.92-1.07 (m, 1 H) |
| 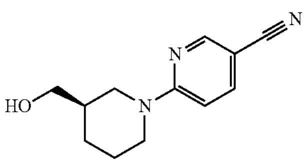 [SMILES: N#Cc1ccc(N2CCC[C@@H](CO)C2)nc1] | 3 | $C_{12}H_{16}N_3O$ | 218.12 | 218.2 | 1.729/C | $^1$H NMR (400 MHz, acetone-$d_6$) δ ppm 8.39 (dd, J = 2.3, 0.8 Hz, 1 H), 7.67-7.76 (m, 1 H), 6.82-6.90 (m, 1 H), 4.46 (d, J = 11.0 Hz, 1 H), 4.34 (d, J = 13.7 Hz, 1 H), 3.70 (t, J = 5.5 Hz, 1 H), 3.48-3.57 (m, 1 H), 3.40-3.48 (m, 1 H), 3.08 (ddd, J = 13.3, 11.3, 3.1 Hz, 1 H), 2.89 (dd, J = 13.1, 10.4 Hz, 1 H), 1.81-1.92 (m, 1 H), 1.67-1.81 (m, 2 H), 1.45-1.59 (m, 1 H), 1.30-1.43 (m, 1 H) |
| | 1 | $C_{15}H_{22}NO_3$ | 264.1594 | 264.1648 | 1.582/C | $^1$H NMR (400 MHz, acetone-$d_6$) δ ppm 7.73-7.90 (m, 2 H), 6.83-7.04 (m, 2 H), 4.25 (q, J = 7.3 Hz, 2 H), 4.05-4.19 (m, 1 H), 3.55-3.82 (m, 4 H), 3.05 (td, J = 12.5, 3.1 Hz, 1 H), 2.01 (dd, J = 4.3, 2.7 Hz, 1 H), 1.51-1.80 (m, 5 H), 1.31 (t, J = 7.0 Hz, 3 H) |
| | 1 | $C_{13}H_{17}N_2O$ | 217.1335 | 217.1342 | 1.566/C | $^1$H NMR (400 MHz, acetone-$d_6$) δ ppm 7.42-7.51 (m, 2 H), 6.94-7.04 (m, 2 H), 4.09-4.19 (m, 1 H), 3.63-3.83 (m, 4 H), 3.07 (td, J = 12.7, 3.1 Hz, 1 H), 1.95-2.03 (m, 1 H), 1.51-1.81 (m, 5 H) |
| | 1 | $C_{15}H_{22}NO_3$ | 264.15 | 264.2 | 1.890/C | $^1$H NMR (400 MHz, acetone-$d_6$) δ ppm 7.79-7.88 (m, 2 H), 6.90-7.02 (m, 2 H), 4.26 (q, J = 7.2 Hz, 2 H), 3.97 (dt, J = 12.9, 2.3 Hz, 2 H), 3.55-3.61 (m, 1 H), 3.44 (t, J = 5.9 Hz, 2 H), 2.86 (td, J = 12.5, 2.7 Hz, 2 H), 1.79-1.88 (m, 2 H), 1.64-1.77 (m, 1 H), 1.24-1.38 (m, 5 H) |
| | 1 | $C_{13}H_{17}N_2O$ | 217.13 | 217.2 | 1.892/C | $^1$H NMR (400 MHz, acetone-$d_6$) δ ppm 7.46-7.54 (m, 2 H), 6.99-7.05 (m, 2 H), 3.99 (dt, J = 13.0, 2.5 Hz, 2 H), 3.55-3.62 (m, 1 H), 3.44 (t, J = 5.9 Hz, 2 H), 2.90 (td, J = 12.7, 2.7 Hz, 2 H), 1.79-1.88 (m, 2 H), 1.65-1.79 (m, 1 H), 1.23-1.37 (m, 2 H) |

| Structure | General Method | Formula [M + H]+ | Calc. [M + H]+ m/z | LCMS [M + H]+ m/z | HPLC RT (Min)/ Method | NMR |
|---|---|---|---|---|---|---|
| 4-Cl-phenyl-piperidin-4-yl-methanol | 1 | $C_{12}H_{17}ClNO$ | 226.09 | 226.2 | 1.548/C | $^1$H NMR (400 MHz, acetone-$d_6$) δ ppm 7.15-7.21 (m, 2 H), 6.91-6.98 (m, 2 H), 3.67-3.76 (m, 2 H), 3.52-3.58 (m, 1 H), 3.44 (t, J = 5.9 Hz, 2 H), 2.69 (td, J = 12.2, 2.5 Hz, 2 H), 1.83 (d, J = 13.3 Hz, 2 H), 1.54-1.67 (m, 1 H), 1.32 (qd, J = 12.4, 3.9 Hz, 2 H) |
| 4-F-phenyl-piperidin-4-yl-methanol | 1 | $C_{12}H_{17}FNO$ | 210.1289 | 210.1299 | 1.535/C | $^1$H NMR (400 MHz, acetone-$d_6$) δ ppm 6.92-7.02 (m, 4 H), 3.57-3.68 (m, 2 H), 3.51-3.57 (m, 1 H), 3.44 (t, J = 5.9 Hz, 2 H), 2.63 (td, J = 12.0, 2.5 Hz, 2 H), 1.83 (d, J = 12.5 Hz, 2 H), 1.50-1.64 (m, 1 H), 1.27-1.42 (m, 2 H) |
| phenyl-piperidin-4-yl-methanol | 1 | $C_{12}H_{18}NO$ | 192.13 | 192.2 | 1.106/C | $^1$H NMR (400 MHz, acetone-$d_6$) δ ppm 7.19 (dd, J = 8.8, 7.2 Hz, 2 H), 6.94 (d, J = 8.2 Hz, 2 H), 6.74 (t, J = 7.2 Hz, 1 H), 3.72 (dt, J = 12.1, 2.5 Hz, 2 H), 3.51-3.58 (m, 1 H), 3.44 (t, J = 5.9 Hz, 2 H), 2.66 (td, J = 12.2, 2.5 Hz, 2 H), 1.78-1.87 (m, 2 H), 1.52-1.66 (m, 1 H), 1.26-1.41 (m, 2 H) |
| (3S)-4-F-phenyl-piperidin-3-yl-methanol | 1 | $C_{12}H_{17}FNO$ | 210.1289 | 210.1312 | 0.982/C | $^1$H NMR (400 MHz, acetone-$d_6$) δ ppm 6.91-7.02 (m, 3 H), 3.58-3.69 (m, 2 H), 3.40-3.56 (m, 3 H), 2.65 (td, J = 11.5, 2.7 Hz, 1 H), 2.45 (dd, J = 11.9, 10.0 Hz, 1 H), 1.72-1.89 (m, 3 H), 1.56-1.71 (m, 1 H), 1.05-1.19 (m, 1 H) |
| (3S)-phenyl-piperidin-3-yl-methanol | 1 | $C_{12}H_{18}NO$ | 192.13 |  | 1.0/C | $^1$H NMR (400 MHz, acetone-$d_6$) δ ppm 7.19 (dd, J = 8.6, 7.4 Hz, 2 H), 6.94 (d, J = 8.2 Hz, 2 H), 6.73 (t, J = 7.2 Hz, 1 H), 3.75 (dt, J = 11.8, 1.7 Hz, 1 H), 3.41-3.65 (m, 4 H), 2.69 (td, J = 11.6, 2.9 Hz, 1 H), 2.49 (dd, J = 11.9, 10.0 Hz, 1 H), 1.71-1.88 (m, 3 H), 1.56-1.70 (m, 1 H), 1.08-1.22 (m, 1 H) |
| (3R)-phenyl-piperidin-3-yl-methanol | 1 | $C_{12}H_{18}NO$ | 192.13 | 192.2 |  | $^1$H NMR (400 MHz, acetone-$d_6$) δ ppm 7.14-7.24 (m, 2 H), 6.94 (d, J = 8.2 Hz, 2 H), 6.73 (t, J = 7.2 Hz, 1 H), 3.76 (dt, J = 11.8, 1.9 Hz, 1 H), 3.41-3.64 (m, 4 H), 2.69 (td, J = 11.6, 2.9 Hz, 1 H), 2.49 (dd, J = 11.9, 10.0 Hz, 1 H), 1.71-1.91 (m, 3 H), 1.56-1.71 (m, 1 H), 1.08-1.22 (m, 1 H) |
| 4-Cl-phenyl-piperidin-2-yl-methanol | 1 | $C_{12}H_{17}ClNO$ | 226.09 | 226.2 | 1.240/C | $^1$H NMR (400 MHz, acetone-$d_6$) δ ppm 7.15 (d, J = 9.0 Hz, 2 H), 6.92 (d, J = 9.0 Hz, 2 H), 3.83-3.93 (m, 1 H), 3.63-3.72 (m, 1 H), 3.51-3.62 (m, 2 H), 3.40 (dt, J = 12.8, 3.6 Hz, 1 H), 2.93-3.03 (m, 1 H), 1.93-2.00 (m, 1 H), 1.51-1.76 (m, 5 H) |

-continued

| Structure | General Method | Formula [M + H]+ | Calc. [M + H]+ m/z | LCMS [M + H]+ m/z | HPLC RT (Min)/ Method | NMR |
|---|---|---|---|---|---|---|
| | 6 | C8H14N3OS | 200.08 | 200.2 | 1.280/C | 1H NMR (400 MHz, acetone-d6) δ ppm 8.59 (s, 1 H), 3.99 (dd, J = 12.5, 3.9 Hz, 1 H), 3.85-3.94 (m, 1 H), 3.74 (t, J = 5.5 Hz, 1 H), 3.50-3.59 (m, 1 H), 3.39-3.49 (m, 1 H), 3.09-3.20 (m, 1 H), 2.98 (dd, J = 12.5, 10.2 Hz, 1 H), 1.74-1.88 (m, 3 H), 1.57-1.72 (m, 1 H), 1.23-1.37 (m, 1 H) |
| | 6 | C12H19N2O3S | 271.10 | 271.2 | 1.976/C | 1H NMR (400 MHz, acetone-d6) δ ppm 7.77 (s, 1 H), 4.23 (q, J = 7.0 Hz, 2 H), 4.10 (dd, J = 13.3, 3.5 Hz, 1 H), 3.99 (d, J = 13.3 Hz, 1 H), 3.76 (t, J = 5.5 Hz, 1 H), 3.51-3.60 (m, 1 H), 3.45 (dt, J = 10.7, 6.6 Hz, 1 H), 3.15 (td, J = 12.2, 2.9 Hz, 1 H), 2.98 (dd, J = 12.7, 10.4 Hz, 1 H), 1.75-1.93 (m, 3 H), 1.53-1.69 (m, 1 H), 1.31-1.41 (m, 1 H), 1.29 (t, J = 7.0 Hz, 3 H) |
| | 6 | C9H14BrN2OS | 276.99 278.99 | 277.0 279.0 | 1.712/C | 1H NMR (400 MHz, acetone-d6) δ ppm 7.06 (s, 1 H), 3.90-3.99 (m, 1 H), 3.77-3.86 (m, 1 H), 3.72 (dd, J = 5.9, 5.1 Hz, 1 H), 3.49-3.58 (m, 1 H), 3.38-3.48 (m, 1 H), 3.02 (ddd, J = 12.9, 11.3, 3.1 Hz, 1 H), 2.84 (dd, J = 12.5, 10.2 Hz, 1 H), 1.71-1.87 (m, 3 H), 1.52-1.66 (m, 1 H), 1.22-1.35 (m, 1 H) |
| | 6 | C11H16ClN2O | 227.09 | 227.2 | 1.312/C | 1H NMR (400 MHz, acetone-d6) δ ppm 8.04 (d, J = 2.7 Hz, 1 H), 7.47 (dd, J = 9.4, 2.7 Hz, 1 H), 6.79 (d, J = 9.0 Hz, 1 H), 4.25-4.33 (m, 1 H), 4.18 (dt, J = 12.9, 3.9 Hz, 1 H), 3.61-3.69 (m, 1 H), 3.38-3.55 (m, 2 H), 2.85-2.96 (m, 1 H), 2.72 (dd, J = 12.9, 10.2 Hz, 1 H), 1.78-1.87 (m, 1 H), 1.65-1.78 (m, 2 H), 1.43-1.59 (m, 1 H), 1.21-1.34 (m, 1 H) |
| | 6 | C10H15BrN3O | 272.03 274.03 | 272.0 274.0 | 1.951/C | 1H NMR (400 MHz, acetone-d6) δ ppm 8.33 (s, 2 H), 4.70 (ddt, J = 13.1, 3.9, 1.7 Hz, 1 H), 4.47-4.57 (m, 1 H), 3.63-3.69 (m, 1 H), 3.38-3.55 (m, 2 H), 2.96 (ddd, J = 13.1, 11.5, 3.1 Hz, 1 H), 2.77 (dd, J = 13.1, 10.4 Hz, 1 H), 1.78-1.90 (m, 1 H), 1.61-1.78 (m, 2 H), 1.40-1.54 (m, 1 H), 1.24-1.37 (m, 1 H) |
| 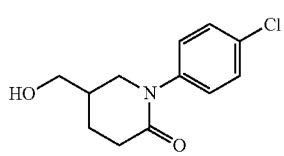 [SMILES: O=C1CCC(CO)CN1c1ccc(Cl)cc1] | 5 | C12H15ClNO2 | 240.07 | 240.2 | 1.622/C | |
| | 1 | C17H27N2O3 | 307.19 | 307.2 | 1.599/C | 1H NMR (400 MHz, acetone-d6) δ ppm 8.07 (br. s., 1 H), 7.29-7.47 (m, J = 8.6 Hz, 2 H), 6.81-6.97 (m, 2 H), 3.62-3.69 (m, 1 H), 3.56-3.62 (m, 1 H), 3.40-3.56 (m, 3 H), 2.62 (td, J = 11.5, 2.7 Hz, 1 H), 2.42 (dd, J = 11.7, 9.8 Hz, 1 H), 1.72-1.89 (m, 3 H), 1.56-1.71 (m, 1 H), 1.46 (s, 8 H), 1.05-1.17 (m, 1 H) |
| | 1 | C16H26N3O3 | 308.19 | 308.2 | 1.769/C | 1H NMR (400 MHz, CDCl3) δ ppm 7.93 (d, J = 3.1 Hz, 1 H), 7.78 (d, J = 9.0 Hz, 1 H), 7.30 (dd, J = 9.0, 3.1 Hz, 1 H), 7.05 (br. s., 1 H), 3.63-3.71 (m, 1 H), 3.54-3.63 (m, 2 H), 3.43 (dt, J = 11.5, 3.8 Hz, 1 H), 2.73 (td, J = 11.3, 3.1 Hz, 1 H), 2.56 (dd, J = 11.7, 9.8 Hz, 1 H), 1.89-2.01 (m, 1 H), 1.78-1.89 (m, 2 H), 1.65-1.78 (m, 1 H), 1.52 (s, 8 H), 1.40-1.47 (m, 1 H), 1.12-1.24 (m, 1 H) |

| Structure | General Method | Formula [M + H]+ | Calc. [M + H]+ m/z | LCMS [M + H]+ m/z | HPLC RT (Min)/ Method | NMR |
|---|---|---|---|---|---|---|
| | 1 | C20H26NO3 | 328.18 | 328.2 | 1.800/C | 1H NMR (400 MHz, CDCl3) δ ppm 7.32-7.39 (m, 2 H), 6.85-6.98 (m, 5 H), 4.94 (s, 2 H), 3.82 (s, 3 H), 3.56-3.71 (m, 2 H), 3.52 (dd, J = 11.5, 3.7 Hz, 1 H), 3.36 (dt, J = 11.6, 4.0 Hz, 1 H), 2.65-2.75 (m, 1 H), 2.54 (dd, J = 11.7, 9.4 Hz, 1 H), 1.89-2.01 (m, 1 H), 1.66-1.89 (m, 3 H), 1.12-1.25 (m, 1 H) |
| | 1 | C12H17FNO | 210.12 | 210.2 | 1.18/C | 1H NMR (400 MHz, acetone-d6) δ ppm 6.91-7.02 (m, 3 H), 3.58-3.69 (m, 2 H), 3.41-3.56 (m, 3 H), 2.65 (td, J = 11.5, 2.7 Hz, 1 H), 2.45 (dd, J = 11.7, 9.8 Hz, 1 H), 1.72-1.88 (m, 3 H), 1.57-1.72 (m, 1 H), 1.06-1.23 (m, 1 H) |

Example 1. (R)-4-(2-(((6-methoxy-2-(2-methoxy-imidazo[2,1-b][1,3,4]thiadiazol-6-yl)benzofuran-4-yl)oxy)methyl)pyrrolidin-1-yl)benzonitrile

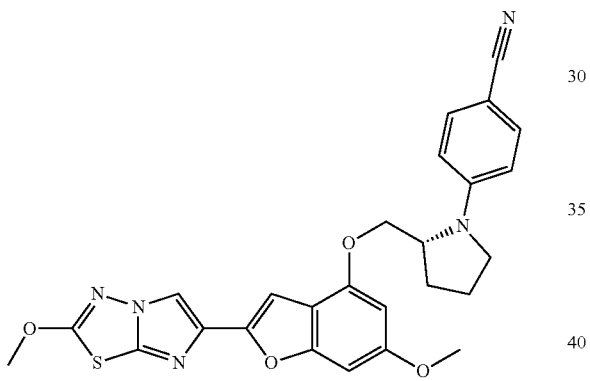

In a 10 ml round-bottomed flask, a mixture of Intermediate 1,6-methoxy-2-(2-methoxyimidazo[2,1-b][1,3,4]thiadiazol-6-yl)benzofuran-4-ol (42 mg, 0.132 mmol), (R)-4-(2-(hydroxymethyl)pyrrolidin-1-yl)benzonitrile (62 mg, 0.307 mmol) and tri-n-butylphosphine (0.12 ml, 0.486 mmol) was put on high vacuum for 1 hour before addition of nitrogen and THF (2.5 ml). A solution of 1,1'-(azodicarbonyl)dipiperidine (85 mg, 0.337 mmol) in THF (2.5 mL) was added dropwise over 10 minutes and the mixture was stirred for 2 hours at room temperature. The mixture was diluted in dichloromethane, washed once with saturated aqueous NaHCO3 solution, once with brine, dried on anhydrous Na2SO4, filtrated and concentrated. The residue was purified on ISCO using a 25 g Innoflash® column (CH2Cl2/EtOAc) to give the title material (54 mg, 81%) as white solid after lyophilization in acetonitrile and water. LC (Method A): 2.452 min. MS (ESI) calcd for C26H24N5O4S [M+H]+ m/z 502.1544, found 502.1563. 1H NMR (400 MHz, DMSO-d6) δ ppm 8.37 (s, 1H), 7.56 (d, J=8.6 Hz, 2H), 6.86-6.77 (m, 4H), 6.41 (s, 1H), 4.40-4.31 (m, 1H), 4.21 (s, 3H), 4.19-4.06 (m, 2H), 3.77 (s, 3H), 3.54 (t, J=9.0 Hz, 1H), 3.29-3.19 (m, 1H), 2.23 (td, J=8.9, 17.9 Hz, 1H), 2.16-2.01 (m, 3H).

Example 2: (R)-2-methoxy-6-(6-methoxy-4-((1-(tetrahydro-2H-pyran-4-yl)pyrrolidin-2-yl)methoxy)benzofuran-2-yl)imidazo[2,1-b][1,3,4]thiadiazole

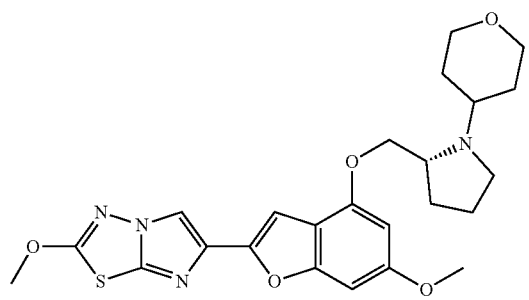 [SMILES: COc1cc(OC[C@H]2CCCN2C2CCOCC2)c2cc(-c3cn4nc(OC)sc4n3)oc2c1]

Example 2a: (R)-tert-butyl 2-(((6-methoxy-2-(2-methoxyimidazo[2,1-b][1,3,4]thiadiazol-6-yl)benzofuran-4-yl)oxy)methyl)pyrrolidine-1-carboxylate

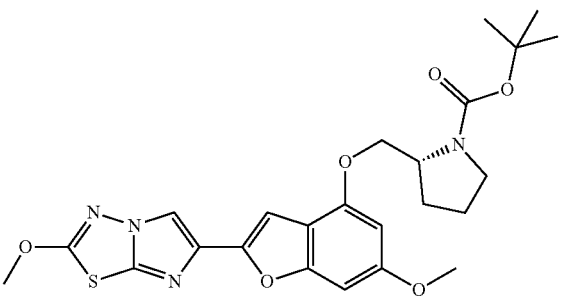 [SMILES: COc1cc(OC[C@H]2CCCN2C(=O)OC(C)(C)C)c2cc(-c3cn4nc(OC)sc4n3)oc2c1]

Using the Mitsunobu reaction conditions described in Example 1, Intermediate 1,6-methoxy-2-(2-methoxyimidazo[2,1-b][1,3,4]thiadiazol-6-yl)benzofuran-4-ol, and (R)-tert-butyl 2-(hydroxymethyl)pyrrolidine-1-carboxylate were converted to the title material (61 mg, 26%), which was obtained as a white solid. LC (Method A): 2.456 min. MS (ESI) calcd for C24H29N4O6S [M+H]+ m/z 501.1802, found 501.1818. 1H NMR (400 MHz, DMSO-d6) δ ppm 8.38 (s, 1H), 6.89 (s, 1H), 6.81 (br. s., 1H), 6.59-6.39 (m, 1H), 4.21 (s, 3H), 4.19-4.00 (m, 3H), 3.80 (s, 3H), 3.35-3.24 (m, 2H), 2.10-1.90 (m, 3H), 1.90-1.77 (m, 1H), 1.40 (br. s., 9H).

Example 2: (R)-2-methoxy-6-(6-methoxy-4-((1-(tetrahydro-2H-pyran-4-yl)pyrrolidin-2-yl)methoxy)benzofuran-2-yl)imidazo[2,1-b][1,3,4]thiadiazole

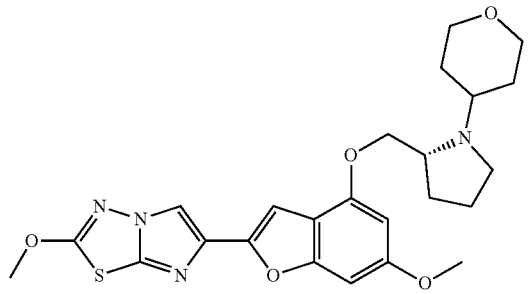 [SMILES: COc1cc(OC[C@H]2CCCN2C2CCOCC2)c2cc(-c3cn4nc(OC)sc4n3)oc2c1]

In a 25 mL round-bottomed flask, (R)-tert-butyl 2-(((6-methoxy-2-(2-methoxyimidazo[2,1-b][1,3,4]thiadiazol-6-yl)benzofuran-4-yl)oxy)methyl)pyrrolidine-1-carboxylate (61 mg, 0.122 mmol) was stirred 30 minutes in a (1:1) mixture of TFA (2 ml) and dichloromethane (2 ml) at room temperature. 2-3 mL of toluene was added and the mixture was concentrated to obtain a white solid. The crude TFA pyrrolidine salt obtained was suspended in 1,2-dichloroethane (7 ml). Triethylamine (0.035 ml, 0.251 mmol) was added and the mixture was stirred 2 minutes and became clear. Then, acetic acid (0.044 ml, 0.769 mmol), dihydro-2H-pyran-4(3H)-one (0.041 ml, 0.442 mmol) and sodium triacetoxyborohydride (159 mg, 0.750 mmol) were added and the mixture was stirred 18 hours at room temperature. The mixture was diluted in dichloromethane and quenched with saturated aqueous NaHCO$_3$ solution. The organic layer was washed once with water, once with saturated aqueous NaHCO$_3$ solution, once with brine, dried on anhydrous Na$_2$SO$_4$, filtered and concentrated. The residue was purified on ISCO using a 12 g Isco® column (CH$_2$Cl$_{12}$/MeOH) to give the title material (40 mg, 68%) as off-white solid after lyophilization in acetonitrile and water. LC (Method A): 1.903 min. MS (ESI) calcd for C$_{24}$H$_{28}$N$_4$O$_5$S [M+H]+ m/z 485.1853, found 485.1881. $^1$H NMR (400 MHz, DMSO-d6) δ ppm 8.08 (s, 1H), 6.97 (s, 1H), 6.76-6.69 (m, 1H), 6.39 (d, J=1.6 Hz, 1H), 4.25 (s, 3H), 4.07-3.88 (m, 4H), 3.84 (s, 3H), 3.51-3.36 (m, 3H), 3.09-3.00 (m, 1H), 2.98-2.86 (m, 1H), 2.76-2.65 (m, 1H), 2.07-1.96 (m, 1H), 1.95-1.77 (m, 5H), 1.74-1.54 (m, 2H).

Example 3: tert-butyl 3-(((6-methoxy-2-(6-methyl-imidazo[1,2-b]pyridazin-2-yl)benzofuran-4-yl)oxy)methyl)-4-(4-methoxyphenyl)piperazine-1-carboxylate

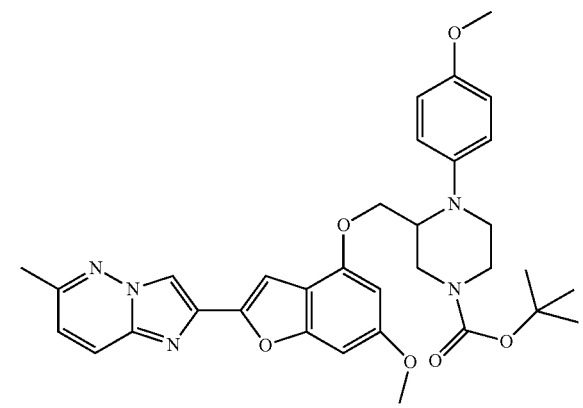 [SMILES: COc1ccc(N2CCN(C(=O)OC(C)(C)C)CC2COc2cc(OC)cc3oc(-c4cn5nc(C)ccc5n4)cc23)cc1]

Example 3a: tert-butyl 3-(hydroxymethyl)-4-(4-methoxyphenyl)piperazine-1-carboxylate

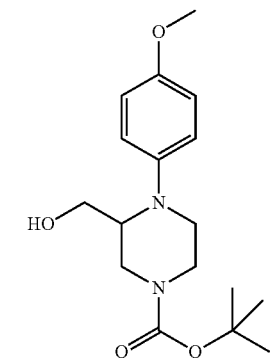 [SMILES: COc1ccc(N2CCN(C(=O)OC(C)(C)C)CC2CO)cc1]

Using the Ullmann reaction condition described in General Method 2, tert-butyl 3-(hydroxymethyl)piperazine-1-carboxylate and 1-iodo-4-methoxybenzene were cross coupled to give the title material (40 mg, 18%) as a yellowish oil. LC (Method B): 1.523 min. MS (APCI) calcd for C$_{17}$H$_{28}$N$_2$O$_4$ [M+H]$^+$ m/z 323.20, found 323.2. $^1$H NMR (400 MHz, CDCl$_3$) δ ppm 6.99-6.89 (m, 2H), 6.89-6.81 (m, 2H), 3.78 (s, 3H), 4.07-3.31 (m, 8H), 3.08 (t, J=3.7 Hz, 2H), 1.50 (s, 9H)

Example 3: tert-butyl 3-(((6-methoxy-2-(6-methyl-imidazo[1,2-b]pyridazin-2-yl)benzofuran-4-yl)oxy)methyl)-4-(4-methoxyphenyl)piperazine-1-carboxylate

Example 4: 2-(6-methoxy-4-((1-(4-methoxyphenyl)piperazin-2-yl)methoxy)benzofuran-2-yl)-6-methyl-imidazo[1,2-b]pyridazine

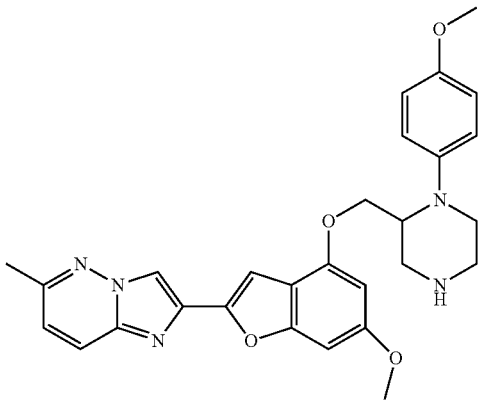

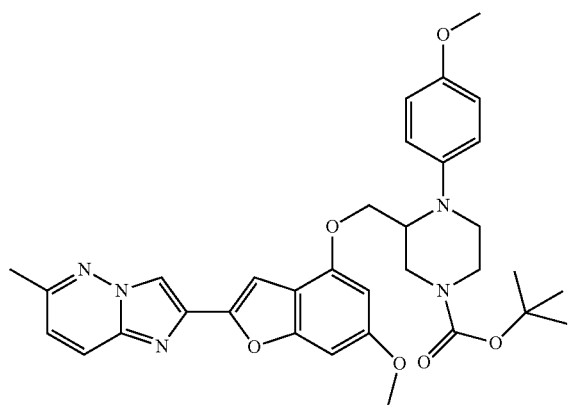 [SMILES: COc1ccc(N2CCN(C(=O)OC(C)(C)C)CC2COc2cc(OC)cc3oc(-c4cn5nc(C)ccc5n4)cc23)cc1]

In a 20 mL vial, tert-butyl 3-(((6-methoxy-2-(6-methyl-imidazo[1,2-b]pyridazin-2-yl)benzofuran-4-yl)oxy)methyl)-4-(4-methoxyphenyl)piperazine-1-carboxylate (51 mg, 0.085 mmol) was stirred in a 1:1 mixture of TFA (1.5 ml) and dichloromethane (1.5 ml) for 2 h at room temperature. 2-3 ml of toluene were added and the mixture was concentrated to give the TFA salt of the title material (62 mg, 100%) as a yellow solid after lyophilization in acetonitrile and water. LC (Method B): 1.866 min. MS (ESI) calcd for $C_{28}H_{30}N_5O_4$ [M+H]+ m/z 500.2292, found 500.2296. $^1$H NMR (400 MHz, DMSO-d6) δ ppm 8.92 (br. s., 1H), 8.67 (br. s., 1H), 8.49 (s, 1H), 7.99 (d, J=9.4 Hz, 1H), 7.20 (d, J=9.4 Hz, 1H), 7.09-7.01 (m, 3H), 6.90-6.82 (m, 3H), 6.27 (s, 1H), 4.24-4.05 (m, 3H), 3.76 (s, 3H), 3.69 (s, 3H), 3.51-3.45 (m, 2H), 3.38-3.16 (m, 4H), 2.53 (s, 3H).

In a 10 ml round-bottomed flask, a mixture of Intermediate 2,6-methoxy-2-(6-methylimidazo[1,2-b]pyridazin-2-yl)benzofuran-4-ol (54 mg, 0.183 mmol), tert-butyl 3-(hydroxymethyl)-4-(4-methoxyphenyl)piperazine-1-carboxylate (84 mg, 0.261 mmol) and tri-n-butylphosphine (0.165 ml, 0.669 mmol) was put on high vacuum for 1 hour before addition of nitrogen and THF (3.5 ml). A solution of 1,1'-(azodicarbonyl)dipiperidine (138 mg, 0.547 mmol) in THF (2.0 mL) was added dropwise over 20 minutes and the mixture was stirred for 5 hours at room temperature. The mixture was diluted in dichloromethane, washed once with saturated aqueous NaHCO$_3$ solution, once with brine, dried on anhydrous Na$_2$SO$_4$, filtrated and concentrated. The residue was purified on ISCO using a 25 g Innoflash® column (Hex/EtOAc) to give the title material (54 mg, 49%) as a light yellow solid after lyophilization in acetonitrile and water. LC (Method B): 2.172 min. MS (ESI) calcd for $C_{33}H_{38}N_5O_6$ [M+H]+ m/z 600.2817, found 600.2829. $^1$H NMR (400 MHz, DMSO-d$_6$) δ ppm 8.51 (s, 1H), 8.01 (d, J=9.4 Hz, 1H), 7.19 (d, J=9.0 Hz, 1H), 7.05 (br. s., 1H), 6.98 (d, J=9.0 Hz, 2H), 6.88-6.80 (m, 3H), 6.34 (br. s., 1H), 4.26-3.81 (m, 5H), 3.77 (s, 3H), 3.70 (s, 3H), 3.38 (dd, J=2.5, 13.1 Hz, 1H), 3.25-2.97 (m, 3H), 2.54 (s, 3H), 1.46-1.08 (m, 9H).

Example 5: (3-(((6-methoxy-2-(6-methylimidazo[1,2-b]pyridazin-2-yl)benzofuran-4-yl)oxy)methyl)-4-(4-methoxyphenyl)piperazin-1-yl)(phenyl)methanone

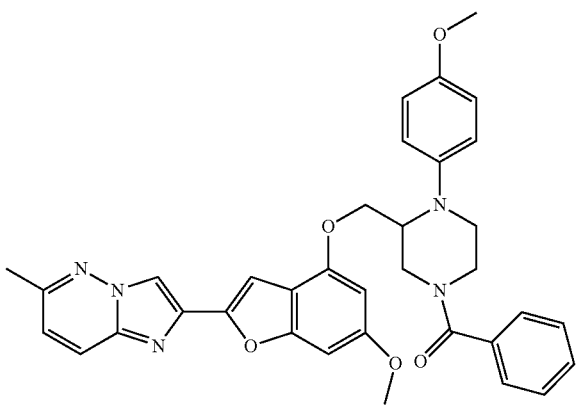 [SMILES: COc1ccc(N2CCN(C(=O)c3ccccc3)CC2COc2cc(OC)cc3oc(-c4cn5nc(C)ccc5n4)cc23)cc1]

To a stirred solution of 2-(6-methoxy-4-((1-(4-methoxyphenyl)piperazin-2-yl)methoxy)benzofuran-2-yl)-6-methyl-imidazo[1,2-b]pyridazine TFA salt (18 mg, 0.029 mmol) and benzoic acid (12 mg, 0.098 mmol) in DMF (1 ml) under nitrogen, Hunig's Base (0.05 ml, 0.286 mmol) was added and the solution was stirred 5 minutes at room temperature. HATU (30 mg, 0.079 mmol) was then added and the reaction was stirred 45 minutes at room temperature. Water was added and the product was extracted three times with CH$_2$Cl$_2$. Combined organic layers were washed once with water, once with brine, dried on anhydrous Na$_2$SO$_4$, filtrated and concentrated. The residue was purified on ISCO using a 4 g Innoflash® column (Hex/EtOAc) to give the title material (13 mg, 73%) as light yellow solid after lyophilization in acetonitrile and water. LC (Method B): 2.105 min. MS (ESI) calcd for C$_{35}$H$_{34}$N$_5$O$_5$ [M+H]+ m/z 604.2554, found 604.2564. $^1$H NMR (400 MHz, DMSO-d$_6$) δ ppm 8.50 (s, 1H), 8.03 (d, J=9.4 Hz, 1H), 7.20 (d, J=9.4 Hz, 1H), 7.01 (d, J=9.0 Hz, 2H), 6.90-6.80 (m, 3H), 7.54-6.68 (m, 6H), 6.32 (br. s., 1H), 3.79 (s, 3H), 3.70 (s, 3H), 4.54-3.15 (m, 9H), 2.55 (s, 3H).

Example 6: cyclopropyl(3-(((6-methoxy-2-(6-methylimidazo[1,2-b]pyridazin-2-yl)benzofuran-4-yl)oxy)methyl)-4-(4-methoxyphenyl)piperazin-1-yl)methanone

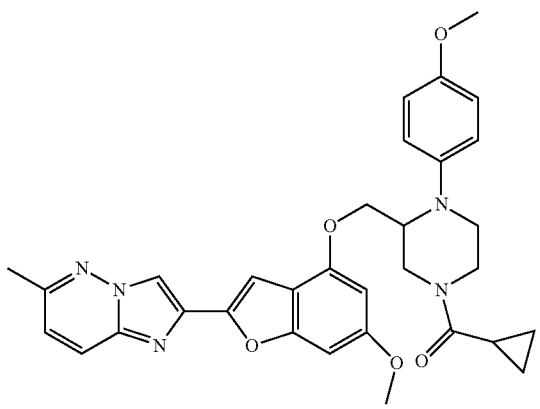 [SMILES: COc1ccc(N2CCN(C(=O)C3CC3)CC2COc2cc(OC)cc3oc(-c4cn5nc(C)ccc5n4)cc23)cc1]

To a stirred solution of 2-(6-methoxy-4-((1-(4-methoxyphenyl)piperazin-2-yl)methoxy)benzofuran-2-yl)-6-methylimidazo[1,2-b]pyridazine TFA salt (18 mg, 0.029 mmol) and cyclopropanecarboxylic acid (0.015 ml, 0.190 mmol) in DMF (1 ml) under nitrogen, Hunig's Base (0.05 ml, 0.286 mmol) was added and the solution was stirred for 5 minutes at room temperature. HATU (31 mg, 0.082 mmol) was then added and the reaction was stirred 45 minutes at room temperature. Water was added and the product was extracted three times with CH$_2$Cl$_2$. Combined organic layers were washed once with water, once with brine, dried on anhydrous Na$_2$SO$_4$, filtrated and concentrated. The residue was purified on ISCO using a 4 g Innoflash® column (Hex/EtOAc to CH$_2$C$_{12}$/MeOH) to give the title material (11 mg, 66%) as white solid after lyophilization in acetonitrile and water. LC (Method B): 2.082 min. MS (ESI) calcd for C$_{32}$H$_{34}$N$_5$O$_5$ [M+H]+ m/z 568.2554, found 568.2564. $^1$H NMR (400 MHz, DMSO-d$_6$) δ ppm 8.50 (s, 1H), 8.01 (d, J=9.4 Hz, 1H), 7.19 (d, J=9.4 Hz, 1H), 7.00 (d, J=9.4 Hz, 2H), 7.12-6.94 (m, 1H), 6.86 (d, J=9.0 Hz, 2H), 6.82 (s, 1H), 6.41-6.21 (m, 1H), 3.77 (s, 3H), 3.70 (s, 3H), 4.59-2.97 (m, 9H), 2.54 (s, 3H), 2.07-1.88 (m, 1H), 0.81-0.15 (m, 4H).

Example 7: 2-(4-((4-(cyclopropylmethyl)-1-(4-methoxyphenyl)piperazin-2-yl)methoxy)-6-methoxybenzofuran-2-yl)-6-methylimidazo[1,2-b]pyridazine

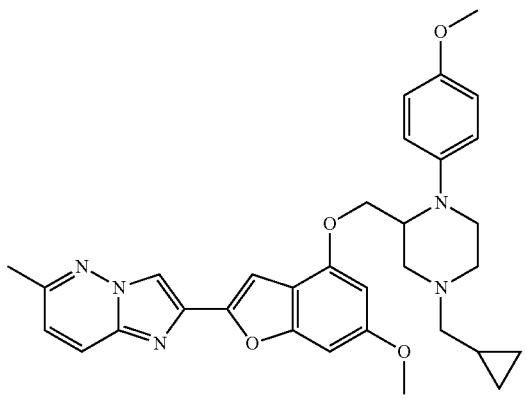 [SMILES: COc1ccc(N2CCN(CC3CC3)CC2COc2cc(OC)cc3oc(-c4cn5nc(C)ccc5n4)cc23)cc1]

In a 25 ml round-bottomed flask under nitrogen, Hunig's Base (0.02 ml, 0.115 mmol), cyclopropanecarbaldehyde (0.014 ml, 0.187 mmol) and sodium triacetoxyborohydride (14 mg, 0.066 mmol) were successively added to a solution of 2-(6-methoxy-4-((1-(4-methoxyphenyl)piperazin-2-yl)methoxy)benzofuran-2-yl)-6-methylimidazo[1,2-b]pyridazine TFA salt (20 mg, 0.033 mmol) in 1,2-dichloroethane (2.5 ml) and the mixture was stirred 2 hours at room temperature. The reaction was quenched with saturated aqueous NaHCO$_3$ solution. The product was extracted from the aqueous layer three times with ethyl acetate. Combined organic layers were washed once with brine, dried on anhydrous Na$_2$SO$_4$, filtrated and concentrated. The residue was purified on ISCO using a 12 g Innoflash® column (CH$_2$Cl$_2$/20% IPA in CH$_2$Cl$_2$) to give the title material (12 mg, 67%) as an off-white solid after lyophilization in acetonitrile and water. LC (Method B): 1.985 min. MS (ESI) calcd for C$_{32}$H$_{36}$N$_5$O$_4$ [M+H]+ m/z 554.2762, found 554.2758. $^1$H NMR (400 MHz, DMSO-d$_6$) δ ppm 8.50 (s, 1H), 8.01 (d, J=9.4 Hz, 1H), 7.19 (d, J=9.4 Hz, 1H), 6.99-6.93 (m, 3H), 6.87-6.79 (m, 3H), 6.31 (d, J=1.6 Hz, 1H), 4.40-4.31 (m, 1H), 4.12 (dd, J=3.7, 7.2 Hz, 1H), 4.01 (dd, J=4.7, 9.0 Hz, 1H), 3.78 (s, 3H), 3.70 (s, 3H), 3.25-3.06 (m, 3H), 2.95 (d, J=11.3 Hz, 1H), 2.54 (s, 3H), 2.45 (dd, J=2.7, 11.0 Hz, 1H), 2.31-2.21 (m, 3H), 0.83 (td, J=7.0, 14.1 Hz, 1H), 0.48-0.37 (m, 2H), 0.13-0.03 (m, 2H).

Example 8: 2-methoxy-6-(6-methoxy-4-((1-tosylpiperidin-3-yl)methoxy)benzofuran-2-yl)imidazo[2,1-b][1,3,4]thiadiazole

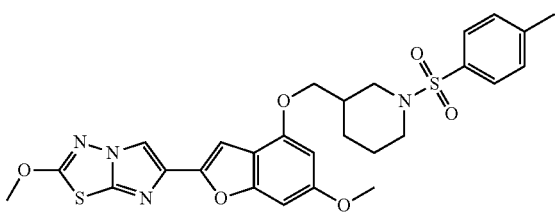

Example 8a: tert-butyl 3-(((6-methoxy-2-(2-methoxyimidazo[2,1-b][1,3,4]thiadiazol-6-yl)benzofuran-4-yl)oxy)methyl)piperidine-1-carboxylate

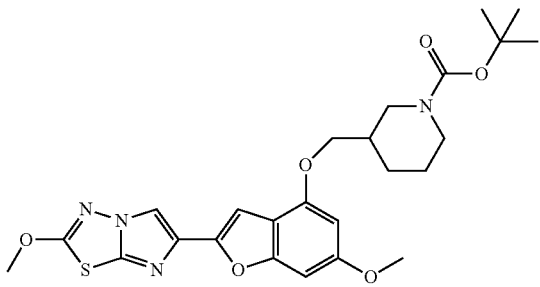 [SMILES: COc1cc(OCC2CCCN(C(=O)OC(C)(C)C)C2)c2cc(-c3cn4nc(OC)sc4n3)oc2c1]

Using the Mitsunobu reaction conditions described in Example 1,6-methoxy-2-(2-methoxyimidazo[2,1-b][1,3,4]thiadiazol-6-yl)benzofuran-4-ol and tert-butyl 3-(hydroxymethyl)piperidine-1-carboxylate were converted to the title material (41 mg, 56.2%) was obtained as white solid. LC (Method C): 2.595 min. MS (ESI) calcd for $C_{25}H_{31}N_4O_6S$ [M+H]$^+$ m/z 515.1959, found 515.1982. $^1$H NMR (400 MHz, DMSO-$d_6$) δ ppm 8.38 (s, 1H), 6.92 (s, 1H), 6.81 (s, 1H), 6.43 (d, J=1.6 Hz, 1H), 4.21 (s, 3H), 3.89-4.06 (m, 3H), 3.80 (s, 4H), 3.60 (t, J=6.3 Hz, 1H), 2.89 (br. s., 1H), 1.93 (d, J=13.3 Hz, 1H), 1.86 (br. s., 1H), 1.76 (dt, J=6.8, 3.2 Hz, 1H), 1.64 (br. s., 1H), 1.28-1.46 (m, 11H).

Example 8: 2-methoxy-6-(6-methoxy-4-((1-tosylpiperidin-3-yl)methoxy)benzofuran-2-yl)imidazo[2,1-b][1,3,4]thiadiazole

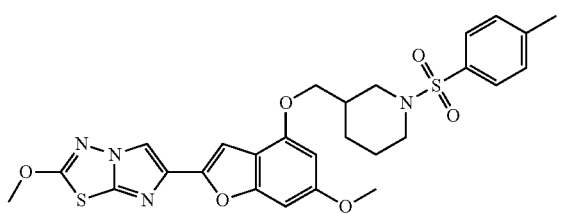

In a 25 mL round-bottomed flask, tert-butyl 3-(((6-methoxy-2-(2-methoxyimidazo[2,1-b][1,3,4]thiadiazol-6-yl)benzofuran-4-yl)oxy)methyl)piperidine-1-carboxylate (20 mg, 0.039 mmol) in dichloromethane (5 ml) was stirred for a 30 minute period with a 4 M solution of HCl in dioxane (0.5 ml) at room temperature; the reaction being monitored by HPLC. At the end of the reaction, toluene (10 ml) was added and the mixture was concentrated to give a white solid. The crude HCl salt was suspended in dichloromethane (4 ml) and diisopropyl ethylamine (0.042 ml, 0.241 mmol) was added. A clear solution was obtained and pyridine (0.012 ml, 0.145 mmol) was added to the solution followed by 4-methylbenzene-1-sulfonyl chloride (18.40 mg, 0.097 mmol) in dichloromethane (1 ml). The reaction progression was followed by HPLC and after 3 hours, the mixture was diluted with dichloromethane (40 ml), washed with water (20 ml), saturated aqueous NaHCO$_3$ (20 ml), brine (20 ml) and dried (MgSO4). The residue after evaporation of the solvent was purified by preparative HPLC (Column Zorbax SB-C18 PrepHT 5 um; 21.2×100 mm) and the pertinent fractions were combined and lyophilized to give title material (6 mg, 21.9%) as an off-white solid. LC (Method C): 2.629 min. MS (ESI) calcd for $C_{27}H_{29}N_4O_6S_2$[M+H]$^+$ m/z 569.1523, found 569.1547. $^1$H NMR (400 MHz, DMSO-$d_6$) δ ppm 8.39 (s, 1H), 7.57-7.67 (m, J=8.6 Hz, 2H), 7.39-7.48 (m, J=8.2 Hz, 2H), 6.87-6.93 (m, 1H), 6.82 (s, 1H), 6.41 (d, J=2.0 Hz, 1H), 4.21 (s, 3H), 3.90-4.06 (m, 2H), 3.80 (s, 3H), 3.68 (dd, J=10.6, 3.5 Hz, 1H), 2.28 (d, J=11.0 Hz, 1H), 2.02-2.16 (m, 1H), 1.69-1.83 (m, 2H), 1.54 (d, J=10.2 Hz, 1H), 1.36 (br. s., 1H), 1.23 (s, 1H), 1.14 (d, J=8.6 Hz, 2H)

Examples 9 to 71

The following additional Examples have been prepared, isolated and characterized using the methods disclosed in Example 1 employing the appropriate alcohols.

Example 72

The following additional Example has been prepared, isolated and characterized using the methods disclosed in Example 3 employing the appropriate amine.

Examples 73 and 74

The following additional Examples have been prepared, isolated and characterized using the methods disclosed in Example 2 employing the appropriate t-butylcarbamate.

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 9 | 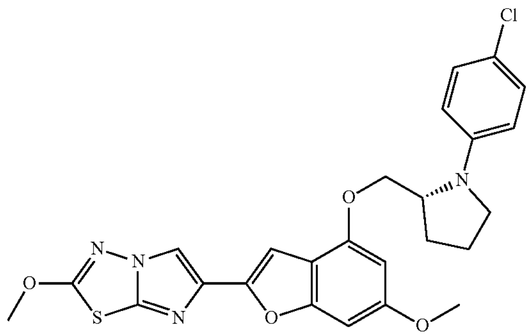 [SMILES: COc1cc(OC[C@H]2CCCN2c2ccc(Cl)cc2)c2cc(-c3cn4nc(OC)sc4n3)oc2c1] | C25H24ClN4O4S | 511.1201 | 2.630/A | 511.1214 | 1H NMR (400 MHz, DMSO-d6) δ ppm 8.38 (s, 1 H) 7.15-7.23 (m, 2 H) 6.87 (s, 1 H) 6.76-6.81 (m, 1 H) 6.67-6.76 (m, 2 H) 6.41 (d, J = 2.0 Hz, 1 H) 4.21 (s, 3 H) 4.13-4.19 (m, 1 H) 4.05-4.12 (m, 2 H) 3.77 (s, 3 H) 3.47 (t, J = 8.2 Hz, 1 H) 3.13 (td, J = 9.0, 6.3 Hz, 1 H) 1.99-2.25 (m, 4 H) |
| 10 | 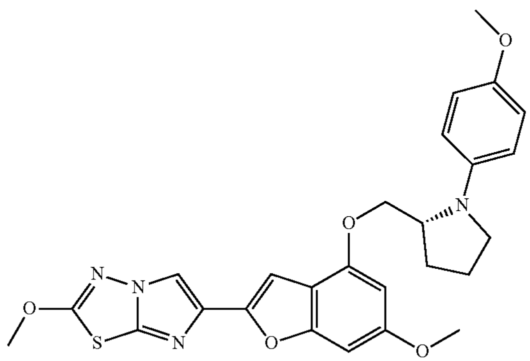 [SMILES: COc1ccc(N2CCC[C@@H]2COc2cc(OC)cc3oc(-c4cn5nc(OC)sc5n4)cc23)cc1] | C26H27N4O5S | 507.1697 | 2.175/A | 507.1724 | 1H NMR (400 MHz, DMSO-d6) δ ppm 8.38 (s, 1H), 6.89 (s, 1H), 6.80-6.84 (m, 2H), 6.78-6.80 (m, 1H), 6.63-6.71 (m, 2H), 6.41 (d, J = 1.6 Hz, 1H), 4.21 (s, 3H), 4.02-4.13 (m, 3H), 3.77 (s, 3H), 3.66 (s, 3H), 3.41-3.49 (m, 1H), 3.07 (td, J = 8.9, 6.5 Hz, 1H), 1.94-2.22 (m, 4H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 11 | 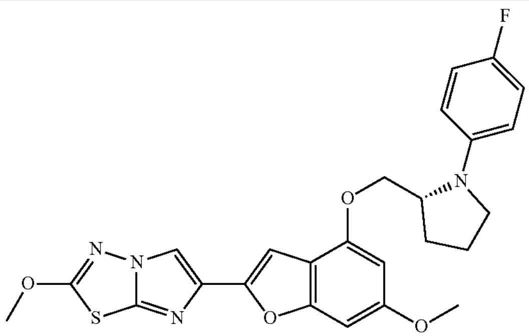 [SMILES: COc1cc(OC[C@H]2CCCN2c2ccc(F)cc2)c2cc(-c3cn4nc(OC)sc4n3)oc2c1] | $C_{25}H_{24}FN_4O_4S$ | 495.1497 | 2.491/A | 495.1514 | $^1$H NMR (400 MHz, DMSO-$d_6$) δ ppm 8.38 (s, 1H), 7.02 (t, J = 9.0 Hz, 2H), 6.88 (s, 1H), 6.77-6.82 (m, 1H), 6.69 (dd, J = 9.2, 4.5 Hz, 2H), 6.38-6.44 (m, 1H), 4.21 (s, 3H), 4.06-4.17 (m, 3H), 3.77 (s, 3H), 3.47 (t, J = 8.2 Hz, 1H), 3.04-3.17 (m, 1H), 1.97-2.26 (m, 4H) |
| 12 | 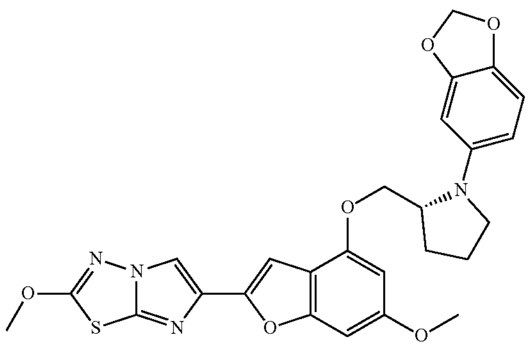 [SMILES: COc1cc(OC[C@H]2CCCN2c2ccc3c(c2)OCO3)c2cc(-c3cn4nc(OC)sc4n3)oc2c1] | $C_{26}H_{25}N_4O_6S$ | 521.1489 | 2.277/A | 521.1513 | $^1$H NMR (400 MHz, DMSO-$d_6$) δ ppm 8.37 (s, 1H), 6.88 (s, 1H), 6.79 (s, 1H), 6.75 (d, J = 8.6 Hz, 1H), 6.44-6.50 (m, 1H), 6.41 (s, 1H), 6.10 (dd, J = 8.4, 1.4 Hz, 1H), 5.87 (s, 2H), 4.21 (s, 3H), 4.04-4.15 (m, 3H), 3.78 (s, 3H), 3.43 (t, J = 8.2 Hz, 1H), 3.01-3.15 (m, 1H), 1.96-2.23 (m, 4H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 13 | 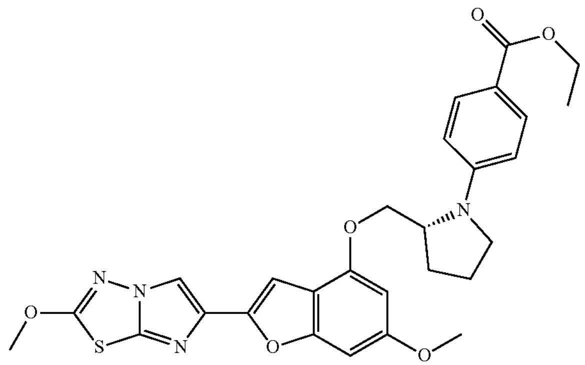 [SMILES: CCOC(=O)c1ccc(N2CCC[C@@H]2COc2cc(OC)cc3oc(-c4cn5nc(OC)sc5n4)cc23)cc1] | C28H29N4O6S | 549.1802 | 2.565/A | 549.1818 | 1H NMR (400 MHz, DMSO-d6) δ ppm 8.36 (s, 1 H), 7.83-7.72 (m, 2 H), 6.85 (s, 1 H), 6.82-6.74 (m, 3 H), 6.41 (d, J = 2.0 Hz, 1 H), 4.40-4.29 (m, 1 H), 4.21 (s, 3 H), 4.22 (q, J = 7.0 Hz, 2 H), 4.18-4.10 (m, 2 H), 3.77 (s, 3 H), 3.54 (t, J = 8.6 Hz, 1 H), 3.29-3.21 (m, 1 H), 2.23 (td, J = 9.0, 18.0 Hz, 1 H), 2.16-2.01 (m, 3 H), 1.28 (t, J = 7.0 Hz, 3 H) |
| 14 | 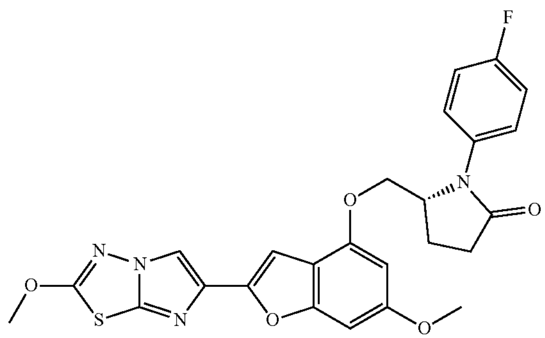 [SMILES: COc1cc(OC[C@H]2CCC(=O)N2c2ccc(F)cc2)c2cc(-c3cn4nc(OC)sc4n3)oc2c1] | C25H22FN4O5S | 509.1289 | 2.259/A | 509.1312 | 1H NMR (400 MHz, DMSO-d6) δ ppm 8.36 (s, 1 H), 7.52-7.43 (m, 2 H), 7.24-7.14 (m, 2 H), 6.81-6.76 (m, 1 H), 6.73 (s, 1 H), 6.31 (d, J = 1.6 Hz, 1 H), 4.77-4.66 (m, 1 H), 4.21 (s, 3 H), 4.18-4.04 (m, 2 H), 3.75 (s, 3 H), 2.79-2.65 (m, 1 H), 2.47-2.30 (m, 2 H), 2.16-2.05 (m, 1 H) |

-continued

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 15 | 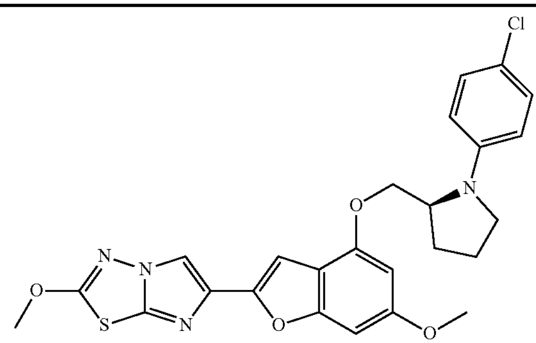 | C25H24ClN4O4S | 511.1220 | 2.632/A | 511.1201 | 1H NMR (400 MHz, DMSO-d6) δ ppm 8.37 (s, 1 H) 7.14-7.23 (m, 2 H) 6.87 (s, 1 H) 6.79 (s, 1 H) 6.67-6.75 (m, 2 H) 6.38-6.44 (m, 1 H) 4.20 (s, 3 H) 4.13-4.19 (m, 1 H) 4.07-4.12 (m, 2 H) 3.77 (s, 3 H) 3.46 (t, J = 8.4 Hz, 1 H) 3.07-3.17 (m, 1 H) 1.99-2.25 (m, 4 H) |
| 16 | 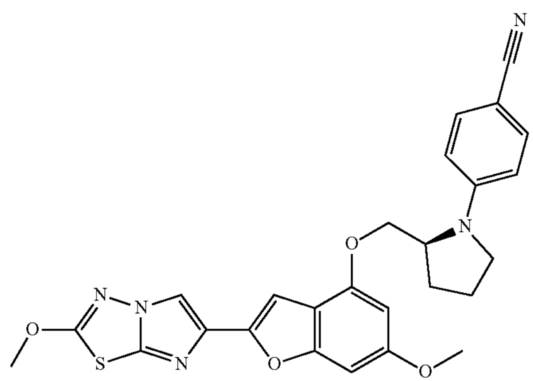 [SMILES: COc1cc(OC[C@@H]2CCCN2c2ccc(C#N)cc2)c2cc(-c3cn4nc(OC)sc4n3)oc2c1] | C26H24N5O4S | 502.1544 | 2.472/A | 502.1570 | 1H NMR (400 MHz, DMSO-d6) δ ppm 8.37 (s, 1 H), 7.52-7.58 (m, 2 H), 6.76-6.85 (m, 4 H), 6.41 (d, J = 2.0 Hz, 1 H), 4.35 (quin, J = 4.5 Hz, 1 H), 4.20 (s, 3 H), 4.13 (qd, J = 9.9, 5.1 Hz, 2 H), 3.77 (s, 3 H), 3.49-3.59 (m, 1 H), 3.19-3.28 (m, 1 H), 2.16-2.29 (m, 1 H), 2.01-2.16 (m, 3 H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 17 | 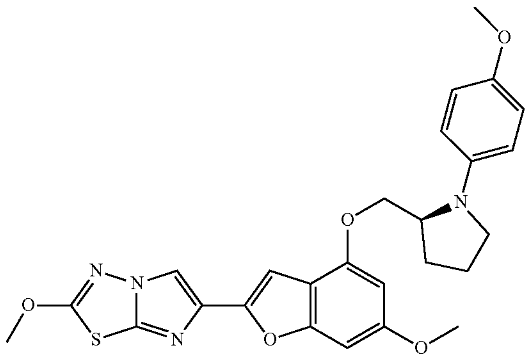 [SMILES: COc1ccc(N2CCC[C@H]2COc2cc(OC)cc3oc(-c4cn5nc(OC)sc5n4)cc23)cc1] | $C_{26}H_{27}N_4O_5S$ | 507.1697 | 2.177/A | 507.1715 | $^1$H NMR (400 MHz, DMSO-d$_6$) δ ppm (s, 1 H), 6.89 (s, 1 H), 6.76-6.86 (m, 3 H), 6.63-6.71 (m, 2 H), 6.41 (d, J = 1.6 Hz, 1 H), 4.20 (s, 3 H), 4.02-4.14 (m, 3 H), 3.77 (s, 3 H), 3.66 (s, 3 H), 3.45 (t, J = 7.8 Hz, 1 H), 3.07 (td, J = 8.9, 6.1 Hz, 1 H), 1.95-2.22 (m, 4 H) |
| 18 | 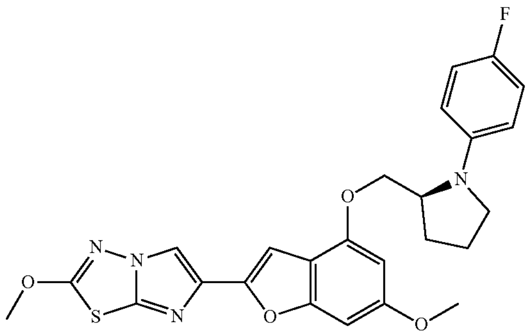 | $C_{25}H_{24}FN_4O_4S$ | 495.1497 | 2.512/A | 495.1518 | $^1$H NMR (400 MHz, DMSO-d$_6$) δ ppm 8.38 (s, 1 H), 6.97-7.07 (m, 2 H), 6.85-6.90 (m, 1 H), 6.79 (dd, J = 2.0, 0.8 Hz, 1 H), 6.66-6.74 (m, 2 H), 6.41 (d, J = 1.6 Hz, 1 H), 4.21 (s, 3 H), 4.05-4.17 (m, 3 H), 3.77 (s, 3 H), 3.40-3.47 (m, 1 H), 3.10 (td, J = 9.3, 6.5 Hz, 1 H), 1.98-2.24 (m, 4 H) |
| 19 | 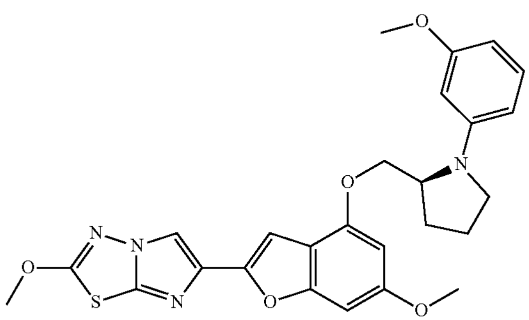 [SMILES: COc1cccc(N2CCC[C@H]2COc2cc(OC)cc3oc(-c4cn5nc(OC)sc5n4)cc23)c1] | $C_{26}H_{27}N_4O_5S$ | 507.1697 | 2.518/A | 507.1711 | $^1$H NMR (400 MHz, DMSO-d$_6$) δ ppm 8.37 (s, 1 H), 7.03-7.11 (m, 1 H), 6.88-6.94 (m, 1 H), 6.79 (dd, J = 2.0, 0.8 Hz, 1 H), 6.42 (d, J = 2.0 Hz, 1 H), 6.31 (dd, J = 8.2, 1.6 Hz, 1 H), 6.18-6.27 (m, 2 H), 4.21 (s, 3 H), 4.05-4.19 (m, 3 H), 3.77 (s, 3 H), 3.70 (s, 3 H), 3.42-3.52 (m, 1 H), 3.06-3.21 (m, 1 H), 2.12-2.25 (m, 1 H), 1.95-2.12 (m, 3 H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 20 | 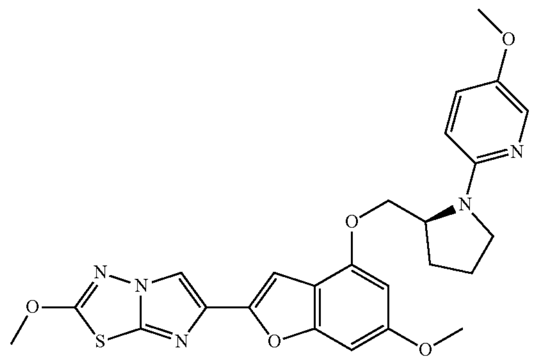 [SMILES: COc1ccc(N2CCC[C@H]2COc2cc(OC)cc3oc(-c4cn5nc(OC)sc5n4)cc23)nc1] | C$_{25}$H$_{26}$N$_5$O$_5$S | 508.1649 | 2.078/A | 508.1672 | $^1$H NMR (400 MHz, acetone-d$_6$) δ ppm 8.09 (s, 1 H), 7.99 (d, J = 3.1 Hz, 1 H), 7.60 (dd, J = 9.4, 2.7 Hz, 1 H), 7.08 (d, J = 9.0 Hz, 1 H), 6.71-6.75 (m, 1 H), 6.48-6.53 (m, 1 H), 4.74 (quin, J = 4.8 Hz, 1 H), 4.24-4.40 (m, 2 H), 4.27 (s, 3 H), 3.75-3.87 (m, 8 H), 3.47-3.60 (m, 1 H), 2.32-2.48 (m, 1 H), 2.14-2.31 (m, 3 H) |
| 21 | 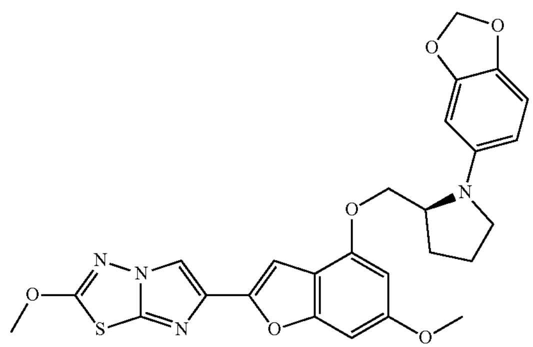 [SMILES: COc1cc(OC[C@@H]2CCCN2c2ccc3c(c2)OCO3)c2cc(-c3cn4nc(OC)sc4n3)oc2c1] | C$_{26}$H$_{25}$N$_4$O$_6$S | 521.1489 | 2.308/A | 521.1518 | $^1$H NMR (400 MHz, DMSO-d$_6$) δ ppm 8.37 (s, 1 H), 6.87-6.90 (m, 1 H), 6.79 (dd, J = 1.8, 1.0 Hz, 1 H), 6.75 (d, J = 8.6 Hz, 1 H), 6.46 (d, J = 2.3 Hz, 1 H), 6.41 (d, J = 2.0 Hz, 1 H), 6.09 (dd, J = 8.6, 2.3 Hz, 1 H), 5.87 (s, 2 H), 4.21 (s, 3 H), 4.08 (br. s, 3 H), 3.78 (s, 3 H), 3.39-3.46 (m, 1 H), 3.08 (td, J = 9.1, 6.5 Hz, 1 H), 2.09-2.21 (m, 1 H), 1.94-2.09 (m, 3 H) |

| Ex. | Structure | Formula [M + H]⁺ | Calc. [M + H]⁺ m/z | HPLC RT (Min)/Method | LCMS [M + H]⁺ m/z | NMR |
|---|---|---|---|---|---|---|
| 22 | 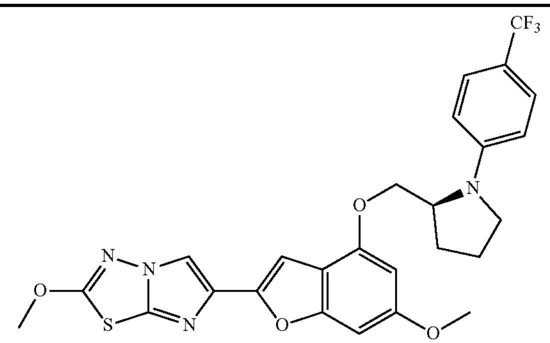 | $C_{26}H_{24}F_3N_4O_4S$ | 525.1403 [M − F]⁺ | 2.580/A | 525.1416 [M − F]⁺ | ¹H NMR (400 MHz, DMSO-d₆) δ ppm 8.37 (s, 1 H), 7.47 (d, J = 8.2 Hz, 2 H), 6.77–6.89 (m, 4 H), 6.39–6.43 (m, 1 H), 4.26–4.34 (m, 1 H), 4.21 (s, 3 H), 4.10–4.16 (m, 2 H), 3.77 (s, 3 H), 3.47–3.57 (m, 1 H), 3.18–3.27 (m, 1 H), 2.16–2.28 (m, 1 H), 2.00–2.16 (m, 3 H) |
| 23 | 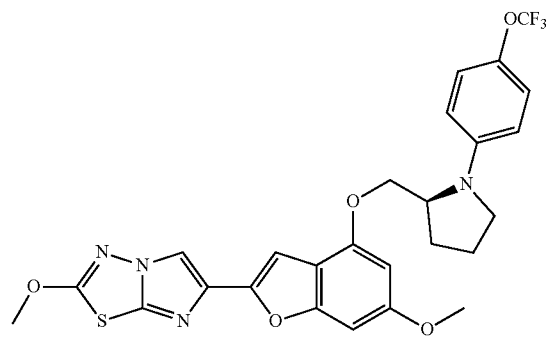 [SMILES: COc1cc(OC[C@@H]2CCCN2c2ccc(OC(F)(F)F)cc2)c2cc(-c3cn4nc(OC)sc4n3)oc2c1] | $C_{26}H_{24}F_3N_4O_5S$ | 561.1414 | 2.622/A | 561.1439 | ¹H NMR (400 MHz, DMSO-d₆) δ ppm 8.37 (s, 1H), 7.16 (d, J = 8.2 Hz, 2H), 6.88 (s, 1H), 6.70–6.81 (m, 3H), 6.39–6.44 (m, 1H), 4.16–4.23 (m, 1H), 4.20 (s, 3H), 4.06–4.16 (m, 2H), 3.77 (s, 3H), 3.43–3.53 (m, 1H), 3.09–3.20 (m, 1H), 2.13–2.26 (m, 1H), 1.97–2.13 (m, 3H) |
| 24 | 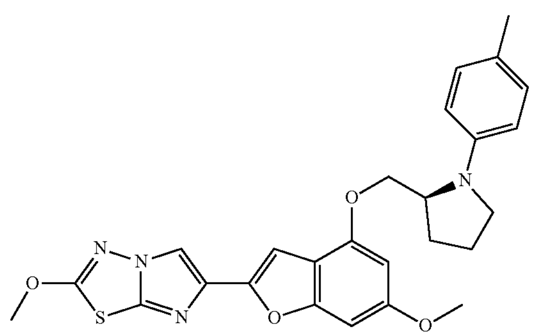 [SMILES: COc1cc(OC[C@@H]2CCCN2c2ccc(C)cc2)c2cc(-c3cn4nc(OC)sc4n3)oc2c1] | $C_{26}H_{27}N_4O_4S$ | 491.1748 | 2.413/A | 491.1757 | ¹H NMR (400 MHz, DMSO-d₆) δ ppm 8.38 (s, 1H), 6.95–7.03 (m, 2H), 6.87–6.91 (m, 1H), 6.79 (dd, J = 1.8, 1.0 Hz, 1H), 6.57–6.65 (m, 2H), 6.41 (d, J = 2.0 Hz, 1H), 4.21 (s, 3H), 4.00–4.14 (m, 3H), 3.77 (s, 3H), 3.45 (t, J = 7.8 Hz, 1H), 3.04–3.14 (m, 1H), 2.14–2.21 (m, 1H), 2.18 (s, 3H), 1.96–2.11 (m, 3H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 25 | 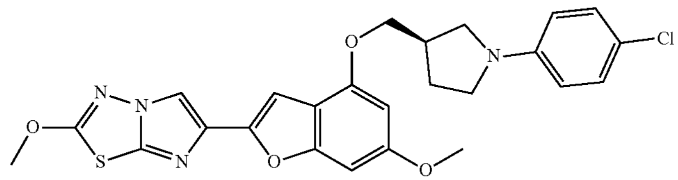 [SMILES: COc1cc(OC[C@@H]2CCN(c3ccc(Cl)cc3)C2)c2cc(-c3cn4nc(OC)sc4n3)oc2c1] | C25H24ClN4O4S | 511.1201 | 2.597/A | 511.1223 | 1H NMR (400 MHz, DMSO-d6) δ ppm 8.37 (s, 1 H) 7.13-7.21 (m, 2 H) 6.91-6.97 (m, 1 H) 6.81 (dd, J = 1.8, 1.0 Hz, 1 H) 6.52-6.60 (m, 2 H) 6.47 (d, J = 2.0 Hz, 1 H) 4.21 (s, 3 H) 4.08-4.20 (m, 2 H) 3.80 (s, 3 H) 3.49 (dd, J = 9.6, 7.6 Hz, 1 H) 3.34-3.41 (m, 1 H) 3.24-3.28 (m, 1 H) 3.17 (dd, J = 9.6, 6.5 Hz, 1 H) 2.86 (spt, J = 6.8 Hz, 1 H) 2.15-2.27 (m, 1 H) 1.3 (dq, J = 12.4, 7.6 Hz, 1 H) |
| 26 | 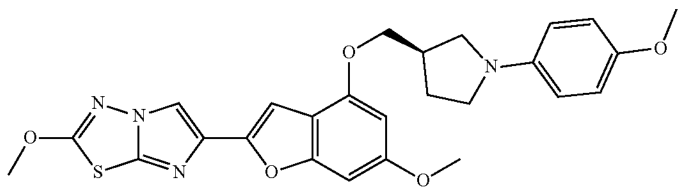 | C26H27N4O5S | 507.1697 | 2.242/A | 507.1702 | 1H NMR (400 MHz, DMSO-d6) δ ppm 8.37 (s, 1 H), 6.94 (s, 1 H), 6.78-6.86 (m, 3 H), 6.56-6.65 (m, 2 H), 6.47 (s, 1 H), 4.20 (s, 3 H), 4.08-4.19 (m, 2 H), 3.80 (s, 3 H), 3.66 (s, 3 H), 3.47 (t, J = 8.6 Hz, 1 H), 3.23-3.38 (m, 2 H), 3.16 (t, J = 7.8 Hz, 1 H), 2.79-2.93 (m, 1 H), 2.14-2.26 (m, 1 H), 1.83-1.97 (m, 1 H) |
| 27 | 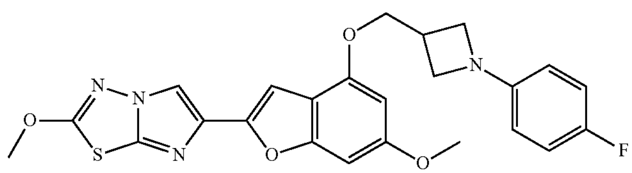 [SMILES: COc1cc(OCC2CN(c3ccc(F)cc3)C2)c2cc(-c3cn4nc(OC)sc4n3)oc2c1] | C24H22FN4O4S | 481.1340 | 2.406/A | 481.1369 | 1H NMR (400 MHz, DMSO-d6) δ ppm 7.84 (s, 1 H), 6.98-6.91 (m, 3 H), 6.72-6.68 (m, 1 H), 6.46-6.38 (m, 2 H), 6.35 (d, J = 2.0 Hz, 1 H), 4.31 (d, J = 7.0 Hz, 2 H), 4.22 (s, 3 H), 4.02 (t, J = 7.4 Hz, 2 H), 3.85 (s, 3 H), 3.76 (dd, J = 5.5, 7.0 Hz, 2 H), 3.30-3.14 (m, 1 H) |
| 28 | 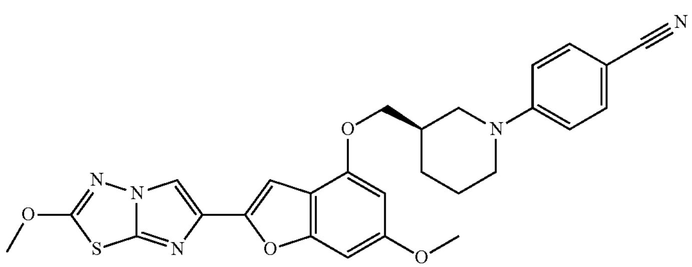 [SMILES: COc1cc(OC[C@@H]2CCCN(c3ccc(C#N)cc3)C2)c2cc(-c3cn4nc(OC)sc4n3)oc2c1] | C27H26N5O4S | 516.1700 | 2.455/A | 516.1718 | 1H NMR (400 MHz, DMSO-d6) δ ppm 8.38 (s, 1 H), 7.58-7.50 (m, 2 H), 7.06-6.98 (m, 3 H), 6.84-6.78 (m, 1 H), 6.44 (d, J = 2.0 Hz, 1 H), 4.21 (s, 3 H), 4.06 (d, J = 6.3 Hz, 2 H), 4.02-3.94 (m, 1 H), 3.88-3.77 (m, 1 H), 3.80 (s, 3 H), 3.07-2.92 (m, 2 H), 2.16-2.02 (m, 1 H), 1.97-1.87 (m, 1 H), 1.76 (td, J = 3.7, 12.9 Hz, 1 H), 1.63-1.38 (m, 2 H) |

| Ex. | Structure | Formula [M + H]+ | Calc. [M + H]+ m/z | HPLC RT (Min)/Method | LCMS [M + H]+ m/z | NMR |
|---|---|---|---|---|---|---|
| 29 | 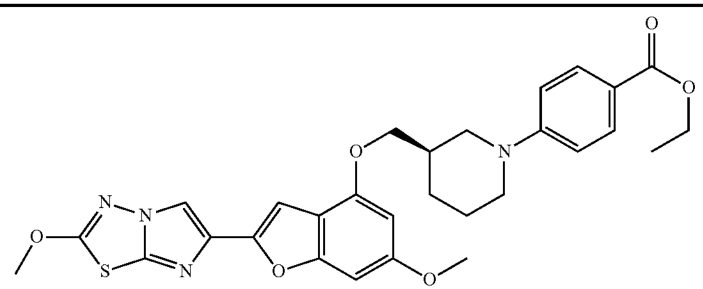 | C29H31N4O6S | 563.1959 | 2.581/A | 563.1980 | 1H NMR (400 MHz, DMSO-d6) δ ppm 8.38 (s, 1 H), 7.80-7.70 (m, 2 H), 7.02 (s, 1 H), 7.00-6.95 (m, 2 H), 6.84-6.80 (m, 1 H), 6.47-6.43 (m, 1 H), 4.21 (s, 3 H), 4.22 (q, J = 7.2 Hz, 2 H), 4.07 (d, J = 6.3 Hz, 2 H), 4.01-3.93 (m, 1 H), 3.86-3.76 (m, 1 H), 3.80 (s, 3 H), 3.03-2.89 (m, 2 H), 2.17-2.08 (m, 1 H), 1.97-1.86 (m, 1 H), 1.81-1.71 (m, 1 H), 1.64-1.52 (m, 1 H), 1.52-1.38 (m, 1 H), 1.27 (t, J = 7.2 Hz, 3 H) |
| 30 | 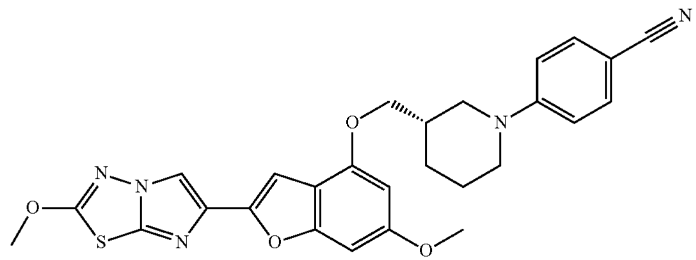 [SMILES: COc1cc(OC[C@H]2CCCN(c3ccc(C#N)cc3)C2)c2cc(-c3cn4nc(OC)sc4n3)oc2c1] | C27H26N5O4S | 516.1700 | 2.461/A | 516.1719 | 1H NMR (400 MHz, DMSO-d6) δ ppm 8.38 (s, 1 H), 7.58-7.49 (m, 2 H), 7.07-6.95 (m, 3 H), 6.84-6.78 (m, 1 H), 6.44 (d, J = 2.0 Hz, 1 H), 4.21 (s, 3 H), 4.06 (d, J = 6.3 Hz, 2 H), 4.02-3.94 (m, 1 H), 3.89-3.77 (m, 1 H), 3.80 (s, 3 H), 3.07-2.89 (m, 2 H), 2.16-2.02 (m, 1 H), 1.98-1.86 (m, 1 H), 1.76 (td, J = 3.5, 12.9 Hz, 1 H), 1.63-1.40 (m, 2 H) |
| 31 | 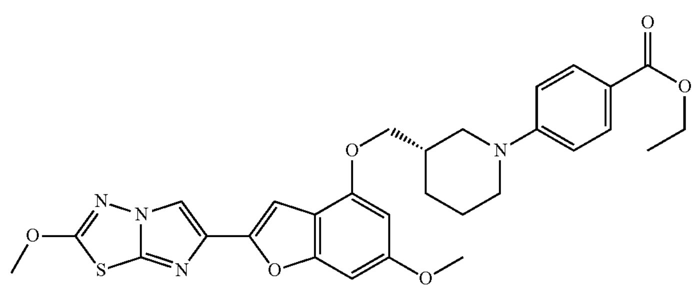 [SMILES: CCOC(=O)c1ccc(N2CCC[C@H](COc3cc(OC)cc4oc(-c5cn6nc(OC)sc6n5)cc34)C2)cc1] | C29H31N4O6S | 563.1959 | 2.575/A | 563.1981 | 1H NMR (400 MHz, DMSO-d6) δ ppm 8.39 (s, 1 H), 7.80-7.71 (m, 2 H), 7.02 (s, 1 H), 7.00-6.95 (m, 2 H), 6.83-6.80 (m, 1 H), 6.45 (d, J = 2.0 Hz, 1 H), 4.21 (s, 3 H), 4.22 (q, J = 7.0 Hz, 2 H), 4.07 (d, J = 6.3 Hz, 2 H), 4.01-3.93 (m, 1 H), 3.86-3.78 (m, 1 H), 3.80 (s, 3 H), 3.02-2.89 (m, 2 H), 2.17-2.08 (m, 1 H), 1.98-1.87 (m, 1 H), 1.77 (td, J = 3.5, 13.0 Hz, 1 H), 1.65-1.51 (m, 1 H), 1.51-1.39 (m, 1 H), 1.27 (t, J = 7.0 Hz, 3 H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 32 | 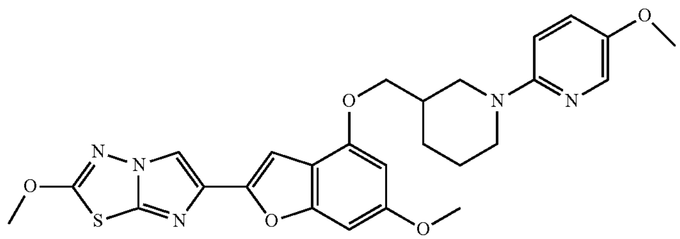 | C26H28N5O5S | 522.1806 | 2.378/C | 522.1857 | 1H NMR (400 MHz, DMSO-d6) δ ppm 8.39 (s, 1 H), 7.79 (br. s., 1 H), 7.41 (br. s., 1 H), 6.95-7.10 (m, 2 H), 6.78-6.86 (m, 1 H), 6.45 (d, J = 2.0 Hz, 1 H), 4.14-4.27 (m, 4 H), 3.94-4.11 (m, 3 H), 3.81 (s, 3 H), 3.75 (s, 3 H), 2.94 (br. s., 2 H), 2.10 (d, J = 9.8 Hz, 1 H), 1.93 (d, J = 9.0 Hz, 1 H), 1.79 (d, J = 12.9 Hz, 1 H), 1.58 (d, J = 12.1 Hz, 1 H), 1.44 ppm (d, J = 11.3 Hz, 1 H) |
| 33 | 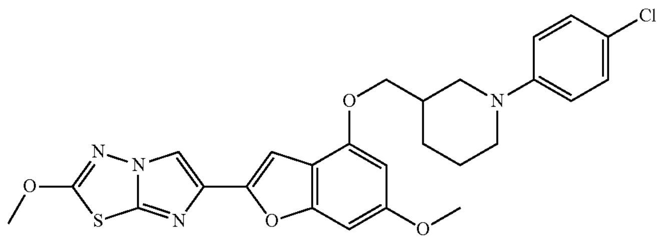 [SMILES: COc1cc(OCC2CCCN(c3ccc(Cl)cc3)C2)c2cc(-c3cn4nc(OC)sc4n3)oc2c1] | C26H26ClN4O4S | 525.1358 | 2.482/C | 525.1390 | 1H NMR (400 MHz, DMSO-d6) δ ppm 8.38 (s, 1 H), 7.17-7.26 (m, 2 H), 6.92-7.02 (m, 3 H), 6.78-6.84 (m, 1 H), 6.45 (d, J = 1.6 Hz, 1 H), 4.21 (s, 3 H), 4.07 (d, J = 6.3 Hz, 2 H), 3.80 (s, 3 H), 3.75 (d, J = 9.0 Hz, 1 H), 3.58 (d, J = 12.1 Hz, 1 H), 2.64-2.84 (m, 2 H), 2.14 (d, J = 3.5 Hz, 1 H), 1.84-1.96 (m, 1 H), 1.72-1.83 (m, 1 H), 1.61 (d, J = 12.9 Hz, 1 H), 1.36 ppm (dd, J = 11.9, 3.3 Hz, 1 H) |
| 34 | 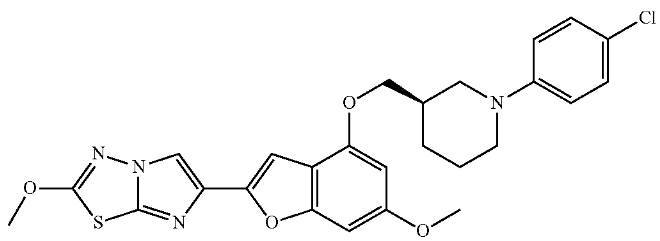 [SMILES: COc1cc(OC[C@@H]2CCCN(c3ccc(Cl)cc3)C2)c2cc(-c3cn4nc(OC)sc4n3)oc2c1] | C26H26ClN4O4S | 525.1358 | 2.530/C | 525.1380 | 1H NMR (400 MHz, DMSO-d6) δ ppm 8.38 (s, 1 H), 7.16-7.25 (m, 2 H), 6.91-7.02 (m, 3 H), 6.81 (dd, J = 2.0, 0.8 Hz, 1 H), 6.45 (d, J = 2.0 Hz, 1 H), 4.21 (s, 3 H), 4.07 (d, J = 6.3 Hz, 2 H), 3.80 (s, 3 H), 3.70-3.78 (m, 1 H), 3.58 (d, J = 12.5 Hz, 1 H), 2.64-2.84 (m, 2 H), 2.15 (br. s., 1 H), 1.90 (dd, J = 12.9, 3.5 Hz, 1 H), 1.70-1.83 (m, 1 H), 1.53-1.69 (m, 1 H), 1.36 ppm (qd, J = 11.7, 3.9 Hz, 1 H) |
| 35 | 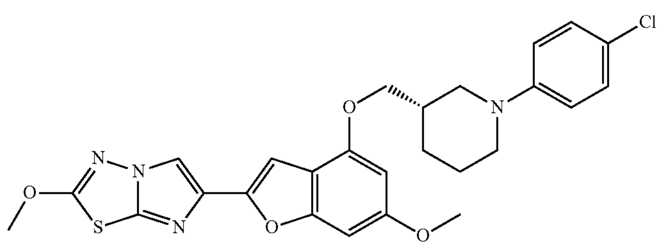 [SMILES: COc1cc(OC[C@H]2CCCN(c3ccc(Cl)cc3)C2)c2cc(-c3cn4nc(OC)sc4n3)oc2c1] | C26H26ClN4O4S | 525.1358 | 2.548/C | 525.1382 | 1H NMR (400 MHz, DMSO-d6) δ ppm 8.38 (s, 1 H), 7.17-7.26 (m, 2 H), 6.91-7.02 (m, 3 H), 6.78-6.85 (m, 1 H), 6.45 (d, J = 2.0 Hz, 1 H), 4.21 (s, 3 H), 4.06 (d, J = 6.7 Hz, 2 H), 3.80 (s, 3 H), 3.74 (dd, J = 12.1, 3.1 Hz, 1 H), 3.58 (d, J = 12.1 Hz, 1 H), 2.64-2.84 (m, 2 H), 2.09-2.22 (m, 1 H), 1.90 (dd, J = 12.9, 3.5 Hz, 1 H), 1.72-1.83 (m, 1 H), 1.61 (d, J = 12.9 Hz, 1 H), 1.36 ppm (dd, J = 11.9, 2.9 Hz, 1 H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 36 | 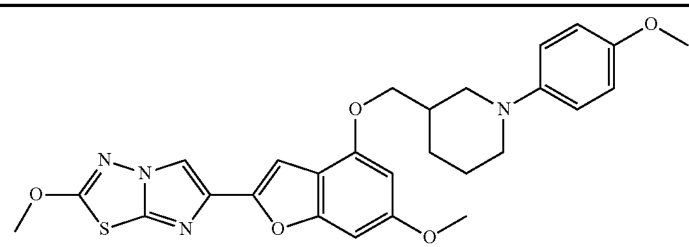 | C24H29N4O5S | 521.1853 | 2.314/C | 521.1884 | 1H NMR (400 MHz, DMSO-d6) δ ppm 8.38 (s, 1 H), 6.96 (s, 1 H), 6.87-6.94 (m, 2 H), 6.77-6.84 (m, 3 H), 6.45 (d, J = 2.0 Hz, 1 H), 4.21 (s, 3 H), 4.07 (d, J = 6.7 Hz, 2 H), 3.80 (s, 3 H), 3.67 (s, 3 H), 3.57 (d, J = 10.6 Hz, 1 H), 3.38 (d, J = 11.0 Hz, 1 H), 2.55-2.65 (m, 2 H), 2.18 (br. s., 1 H), 1.87 (d, J = 11.7 Hz, 1 H), 1.77 (br. s., 1 H), 1.65 (d, J = 11.0 Hz, 1 H), 1.30 (d, J = 11.7 Hz, 1 H) |
| 37 | 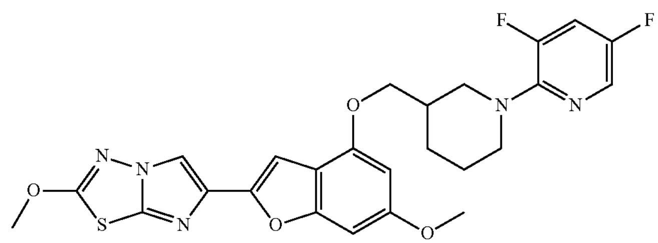 [SMILES: COc1cc(OCC2CCCN(c3ncc(F)cc3F)C2)c2cc(-c3cn4nc(OC)sc4n3)oc2c1] | C25H24F2N5O4S | 528.1512 | 2.655/C | 528.1551 | 1H NMR (400 MHz, DMSO-d6) δ ppm 8.38 (s, 1 H), 8.09 (d, J = 2.3 Hz, 1 H), 7.77 (ddd, J = 12.6, 8.3, 2.5 Hz, 1 H), 6.92 (s, 1 H), 6.77-6.83 (m, 1 H), 6.44 (d, J = 1.6 Hz, 1 H), 4.21 (s, 3 H), 3.99-4.12 (m, 2 H), 3.87-3.97 (m, 1 H), 3.80 (s, 3 H), 3.71 (d, J = 12.5 Hz, 1 H), 2.82-2.97 (m, 2 H), 2.19 (br. s., 1 H), 1.86-1.98 (m, 1 H), 1.74-1.85 (m, 1 H), 1.65 (d, J = 13.3 Hz, 1 H), 1.40 (d, J = 9.0 Hz, 1 H) |
| 38 | 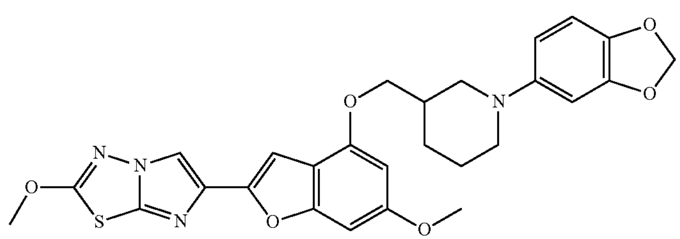 [SMILES: COc1cc(OCC2CCCN(c3ccc4c(c3)OCO4)C2)c2cc(-c3cn4nc(OC)sc4n3)oc2c1] | C27H27N4O6S | 535.1646 | 2.307/C | 535.1701 | 1H NMR (400 MHz, DMSO-d6) δ ppm 8.38 (s, 1 H), 6.97 (d, J = 0.8 Hz, 1 H), 6.79-6.84 (m, 1 H), 6.75 (d, J = 8.6 Hz, 1 H), 6.67 (d, J = 2.3 Hz, 1 H), 645 (d, J = 2.0 Hz, 1 H), 6.37 (dd, J = 8.4, 2.5 Hz, 1 H), 5.90 (s, 2 H), 4.21 (s, 3 H), 4.00-4.12 (m, 2 H), 3.80 (s, 3 H), 3.55 (d, J = 8.6 Hz, 1 H), 3.38 (d, J = 12.1 Hz, 1 H), 2.55-2.73 (m, 2 H), 2.09-2.25 (m, 1 H), 1.83-1.94 (m, 1 H), 1.70-1.83 (m, 1 H), 1.63 (d, J = 12.9 Hz, 1 H), 1.3 (d, J = 8.6 Hz, 1 H) |
| 39 | 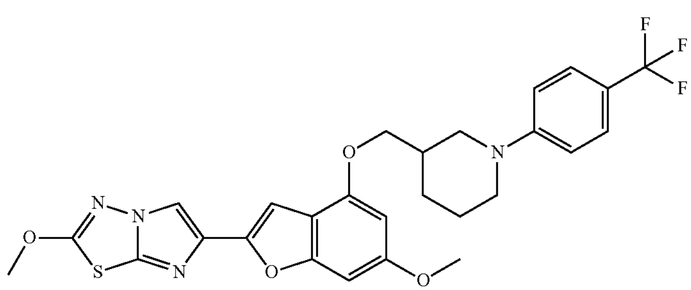 [SMILES: COc1cc(OCC2CCCN(c3ccc(C(F)(F)F)cc3)C2)c2cc(-c3cn4nc(OC)sc4n3)oc2c1] | C27H26F3N4O4S | 559.1621 | 2.645/C | 559.1641 | 1H NMR (400 MHz, DMSO-d6) δ ppm 8.38 (s, 1 H), 7.43-7.54 (m, J = 8.6 Hz, 2 H), 7.03-7.12 (m, J = 9.0 Hz, 2 H), 6.98-7.03 (m, 1 H), 6.78-6.84 (m, 1 H), 6.45 (d, J = 2.0 Hz, 1 H), 4.21 (s, 3 H), 4.07 (d, J = 6.3 Hz, 2 H), 3.94 (d, J = 9.8 Hz, 1 H), 3.72-3.85 (m, 4 H), 2.83-3.00 (m, 2 H), 2.07-2.20 (m, 1 H), 1.86-1.97 (m, 1 H), 1.77 (dt, J = 13.3, 3.5 Hz, 1 H), 1.59 (d, J = 13.3 Hz, 1 H), 1.44 (dd, J = 11.9, 2.9 Hz, 1 H) |

-continued

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 40 | 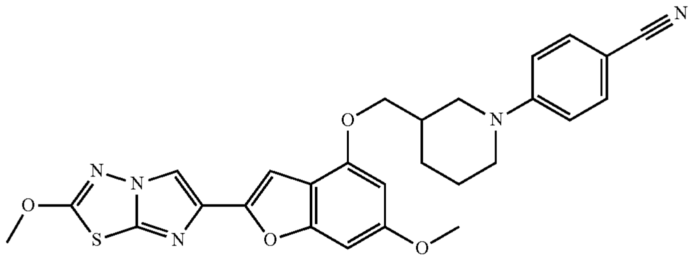 | $C_{27}H_{26}N_5O_4S$ | 516.1700 | 2.699/C | 516.1721 | 1H NMR (400 MHz, DMSO-d6) δ ppm 8.38 (s, 1 H), 7.54 (d, J = 9.4 Hz, 2 H), 6.98-7.07 (m, 3 H), 6.81 (dd, J = 2.0, 0.8 Hz, 1 H), 6.44 (d, J = 2.0 Hz, 1 H), 4.21 (s, 3 H), 4.06 (d, J = 6.3 Hz, 2 H), 3.91-4.03 (m, 1 H), 3.84 (d, J = 13.3 Hz, 1 H), 3.80 (s, 3 H), 2.91-3.07 (m, 2 H), 2.10 (br. s., 1 H), 1.86-1.98 (m, 1 H), 1.76 (dt, J = 13.1, 3.2 Hz, 1 H), 1.39-1.64 (m, 2 H) |
| 41 | 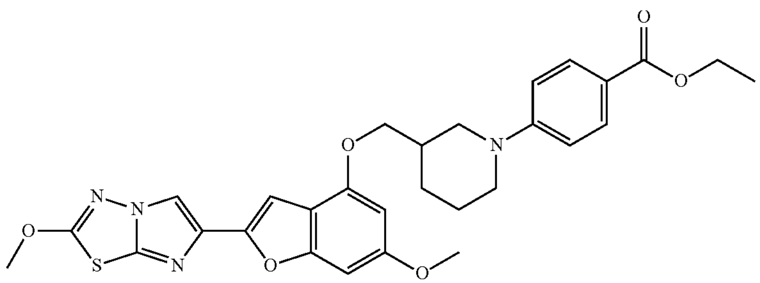 [SMILES: CCOC(=O)c1ccc(N2CCCC(COc3cc(OC)cc4oc(-c5cn6nc(OC)sc6n5)cc34)C2)cc1] | $C_{29}H_{31}N_4O_6S$ | 563.1959 | 2.748/C | 563.1996 | 1H NMR (400 MHz, DMSO-d6) δ ppm 8.39 (s, 1 H), 7.75 (d, J = 9.0 Hz, 2 H), 7.01 (s, 1 H), 6.98 (d, J = 9.4 Hz, 2 H), 6.81 (s, 1 H), 6.45 (d, J = 1.6 Hz, 1 H), 4.17-4.27 (m, 5 H), 4.07 (d, J = 5.9 Hz, 2 H), 3.97 (dd, J = 13.7, 2.7 Hz, 1 H), 3.75-3.87 (m, 4 H), 2.89-3.03 (m, 2 H), 2.12 (br. s., 1 H), 1.87-1.98 (m, 1 H), 1.70-1.82 (m, 1 H), 1.38-1.64 (m, 2 H), 1.27 (t, J = 7.2 Hz, 3 H) |
| 42 | 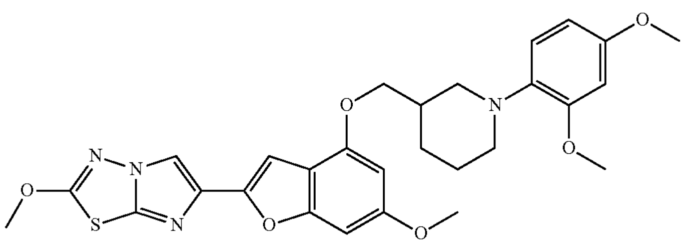 | $C_{28}H_{31}N_4O_6S$ | 551.1959 | 2.370/C | 551.1993 | 1H NMR (400 MHz, DMSO-d6) δ ppm 8.37 (s, 1 H), 6.91 (s, 1 H), 6.83 (d, J = 8.6 Hz, 1 H), 6.80 (d, J = 0.8 Hz, 1 H), 6.49 (d, J = 2.7 Hz, 1 H), 6.37-6.46 (m, 2 H), 4.20 (s, 3 H), 4.07 (d, J = 6.3 Hz, 2 H), 3.80 (s, 3 H), 3.69 (s, 3 H), 3.69 (s, 3 H), 3.25 (br. s., 1 H), 3.11 (d, J = 11.0 Hz, 1 H), 2.53-2.60 (m, 2 H), 2.12-2.28 (m, 1 H), 1.84 (dd, J = 12.9, 4.3 Hz, 1 H), 1.70-1.79 (m, 1 H), 1.58-1.70 (m, 1 H), 1.20-1.38 (m, 1 H) |

-continued

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 43 | 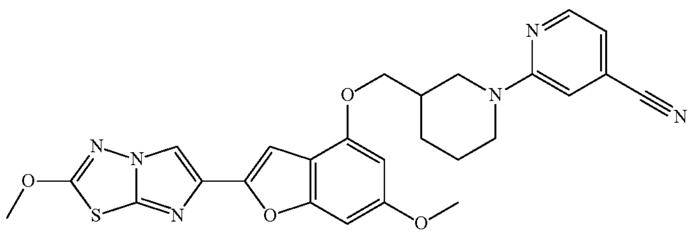 [SMILES: COc1cc(OCC2CCCN(c3cc(C#N)ccn3)C2)c2cc(-c3cn4nc(OC)sc4n3)oc2c1] | $C_{26}H_{25}N_6O_4S$ | 517.1653 | 2.592/C | 517.1679 | $^1$H NMR (400 MHz, DMSO-$d_6$) δ ppm 8.38 (s, 1 H), 8.27 (d, J = 5.1 Hz, 1 H), 7.31 (s, 1 H), 6.96-7.03 (m, 1 H), 6.88 (dd, J = 5.1, 1.2 Hz, 1 H), 6.81 (d, J = 0.8 Hz, 1 H), 6.44 (d, J = 2.0 Hz, 1 H), 4.40 (d, J = 11.0 Hz, 1 H), 4.14-4.25 (m, 4 H), 3.99-4.12 (m, 2 H), 3.80 (s, 3 H), 2.93-3.12 (m, 2 H), 2.04 (br. s., 1 H), 1.94 (d, J = 3.5 Hz, 1 H), 1.76 (d, J = 5.9 Hz, 1 H), 1.42-1.58 (m, 2 H) |
| 44 | 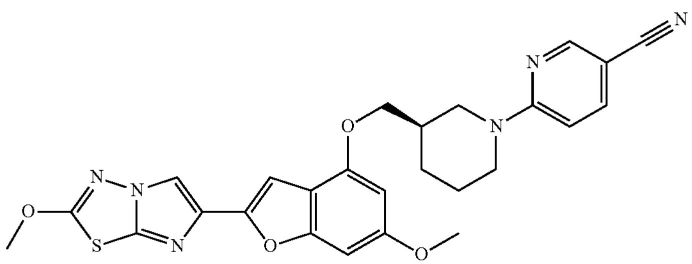 [SMILES: COc1cc(OC[C@@H]2CCCN(c3ccc(C#N)cn3)C2)c2cc(-c3cn4nc(OC)sc4n3)oc2c1] | $C_{26}H_{25}N_6O_4S$ | 517.1653 | 2.659/C | 517.1687 | $^1$H NMR (400 MHz, DMSO-$d_6$) δ ppm 8.47 (d, J = 2.3 Hz, 1 H), 8.38 (s, 1 H), 7.80 (dd, J = 9.0, 2.3 Hz, 1 H), 7.00 (s, 1 H), 6.95 (d, J = 9.4 Hz, 1 H), 6.78-6.85 (m, 1 H), 6.44 (d, J = 1.6 Hz, 1 H), 4.49 (d, J = 11.0 Hz, 1 H), 4.26 (d, J = 12.9 Hz, 1 H), 4.21 (s, 3 H), 4.05 (d, J = 6.3 Hz, 2 H), 3.80 (s, 3 H), 3.02-3.20 (m, 2 H), 1.99-2.10 (m, 1 H), 1.88-1.99 (m, 1 H), 1.72-1.83 (m, 1 H), 1.42-1.60 (m, 2 H) |
| 45 | 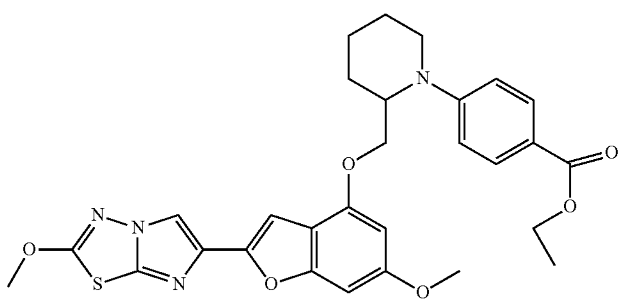 [SMILES: CCOC(=O)c1ccc(N2CCCCC2COc2cc(OC)cc3oc(-c4cn5nc(OC)sc5n4)cc23)cc1] | $C_{29}H_{31}N_4O_6S$ | 563.1959 | 2.612/C | 563.1983 | $^1$H NMR (400 MHz, DMSO-$d_6$) δ ppm 8.25 (s, 1 H), 7.72-7.81 (m, J = 9.0 Hz, 2 H), 6.96-7.05 (m, J = 9.0 Hz, 2 H), 6.76 (d, J = 0.8 Hz, 1 H), 6.42 (d, J = 2.0 Hz, 1 H), 6.39 (s, 1 H), 4.57-4.69 (m, 1 H), 4.27-4.37 (m, 1 H), 4.15-4.27 (m, 6 H), 3.77 (s, 3 H), 3.69 (d, J = 11.3 Hz, 1 H), 3.06-3.17 (m, 2 H), 1.91-2.03 (m, 1 H), 1.61-1.85 (m, 4 H), 1.49-1.61 (m, 1 H), 1.27 (t, J = 7.2 Hz, 3 H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 46 | 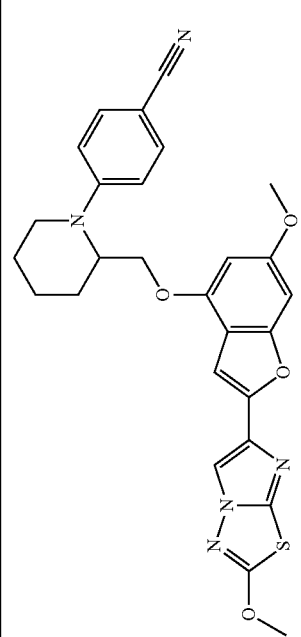 | C27H26N5O4S | 516.1700 | 2.638/C | 516.1716 | 1H NMR (400 MHz, DMSO-d6) δ ppm 8.29 (s, 1 H), 7.47-7.63 (m, J = 9.0 Hz, 2 H), 6.98-7.14 (m, J = 9.4 Hz, 2 H), 6.76 (dd, J = 2.0, 0.8 Hz, 1 H), 6.43 (d, J = 1.6 Hz, 1 H), 6.33 (s, 1 H), 4.66 (d, J = 5.5 Hz, 1 H), 4.29-4.44 (m, 1 H), 4.13-4.29 (m, 4 H), 3.78 (s, 3 H), 3.68 (d, J = 12.5 Hz, 1 H), 3.01-3.18 (m, 1 H), 1.87-2.04 (m, 1 H), 1.60-1.86 (m, 4 H), 1.54 (dd, J = 11.9, 4.1 Hz, 1 H) |
| 47 | 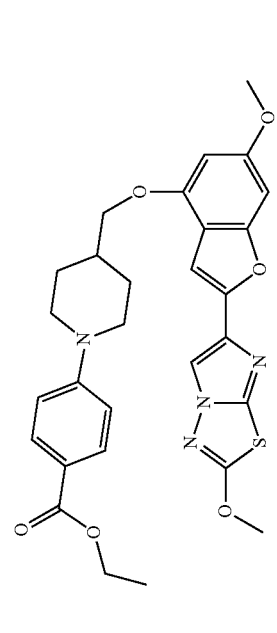 | C29H31N4O6S | 563.1959 | 2.696/C | 263.1976 | 1H NMR (400 MHz, DMSO-d6) δ ppm 8.38 (s, 1 H), 7.72-7.83 (m, J = 9.0 Hz, 2 H), 6.95-7.04 (m, J = 9.0 Hz, 2 H), 6.93 (s, 1 H), 6.77-6.84 (m, 1 H), 6.44 (d, J = 2.0 Hz, 1 H), 4.16-4.28 (m, 5 H), 3.93-4.04 (m, 4 H), 3.79 (s, 3 H), 2.83-2.98 (m, 2 H), 2.02-2.17 (m, 1 H), 1.91 (d, J = 11.0 Hz, 2 H), 1.41 (qd, J = 12.3, 3.9 Hz, 2 H), 1.28 (t, J = 7.2 Hz, 3 H) |
| 48 | 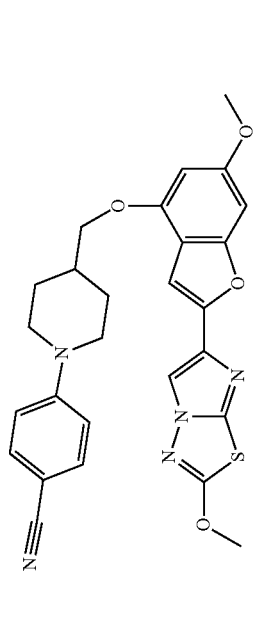 | C27H26N5O4S | 516.1700 | 2.670/C | 516.1715 | 1H NMR (400 MHz, DMSO-d6) δ ppm 8.38 (s, 1 H), 7.51-7.61 (m, 2 H), 6.99-7.08 (m, J = 9.4 Hz, 2 H), 6.91 (s, 1 H), 6.80 (d, J = 0.8 Hz, 1 H), 6.43 (d, J = 2.0 Hz, 1 H), 4.21 (s, 3 H), 3.94-4.05 (m, 4 H), 3.79 (s, 3 H), 2.86-3.01 (m, 2 H), 2.04-2.18 (m, 1 H), 1.89 (d, J = 10.2 Hz, 2 H), 1.39 (qd, J = 12.4, 3.9 Hz, 2 H) |

| Ex. | Structure | Formula [M + H]⁺ | Calc. [M + H]⁺ m/z | HPLC RT (Min)/ Method | LCMS [M + H]⁺ m/z | NMR |
|---|---|---|---|---|---|---|
| 49 | 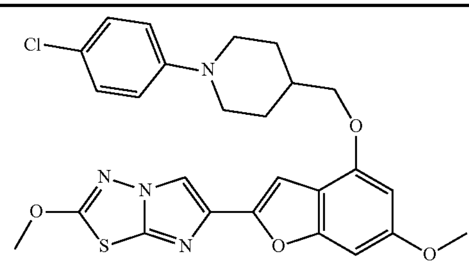 | C₂₆H₂₆ClN₄O₄S | 525.1358 | 2.429/C | 525.1366 | ¹H NMR (400 MHz, DMSO-d₆) δ ppm 8.38 (s, 1 H), 7.21 (d, J = 9.0 Hz, 2 H), 6.92-7.00 (m, 3 H), 6.80 (s, 1 H), 6.44 (d, J = 2.0 Hz, 1 H), 4.21 (s, 3 H), 4.01 (d, J = 7.0 Hz, 2 H), 3.69-3.83 (m, 5 H), 2.72 (s, 2 H), 1.95-2.07 (m, 1 H), 1.91 (d, J = 13.3 Hz, 2 H), 1.36-1.53 (m, 2 H) |
| 50 | 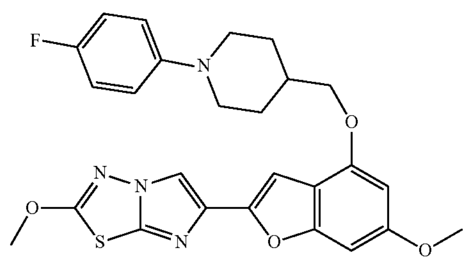 | C₂₆H₂₆FN₄O₄S | 509.1653 | 2.289/C | 509.1683 | ¹H NMR (400 MHz, DMSO-d₆) δ ppm 8.39 (s, 1 H), 6.92-7.10 (m, 5 H), 6.77-6.84 (m, 1 H), 6.45 (d, J = 2.0 Hz, 1 H), 4.21 (s, 3 H), 4.02 (d, J = 5.9 Hz, 2 H), 3.80 (s, 3 H), 3.64 (d, J = 12.1 Hz, 2 H), 2.60-2.74 (m, 2 H), 1.85-2.04 (m, 3 H), 1.48 (qd, J = 11.9, 3.1 Hz, 2 H) |
| 51 | 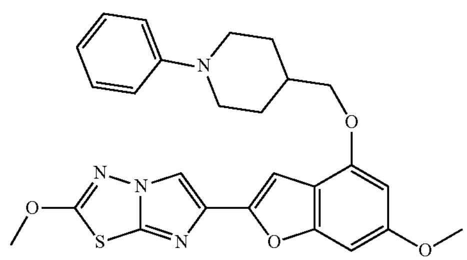 | C₂₆H₂₇N₄O₄S | 491.1748 | 2.286/C | 491.1766 | ¹H NMR (400 MHz, DMSO-d₆) δ ppm 8.39 (s, 1 H), 7.20 (t, J = 7.8 Hz, 2 H), 6.92-6.99 (m, 3 H), 6.80 (s, 1 H), 6.75 (t, J = 7.2 Hz, 1 H), 6.45 (d, J = 2.0 Hz, 1 H), 4.21 (s, 3 H), 4.02 (d, J = 5.9 Hz, 2 H), 3.80 (s, 3 H), 3.74 (d, J = 12.1 Hz, 2 H), 2.64-2.77 (m, 2 H), 1.86-2.06 (m, 3 H), 1.46 (qd, J = 12.1, 3.9 Hz, 2 H) |
| 52 | 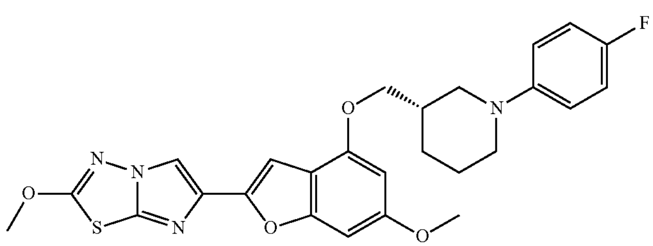 [SMILES: COc1cc(OC[C@H]2CCCN(c3ccc(F)cc3)C2)c2cc(-c3cn4nc(OC)sc4n3)oc2c1] | C₂₆H₂₆FN₄O₄S | 509.1653 | 2.337/C | 509.1702 | ¹H NMR (400 MHz, DMSO-d₆) δ ppm 8.38 (s, 1 H), 6.99-7.09 (m, 2 H), 6.91-6.99 (m, 3 H), 6.81 (s, 1 H), 6.45 (d, J = 2.0 Hz, 1 H), 4.20 (s, 3 H), 4.07 (d, J = 6.3 Hz, 2 H), 3.80 (s, 3 H), 3.59-3.71 (m, 1 H), 3.48 (d, J = 12.1 Hz, 1 H), 2.61-2.78 (m, 2 H), 2.10-2.25 (m, 1 H), 1.84-1.96 (m, 1 H), 1.79 (dt, J = 12.7, 3.4 Hz, 1 H), 1.55-1.72 (m, 1 H), 1.26-1.41 (m, 1 H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 53 | 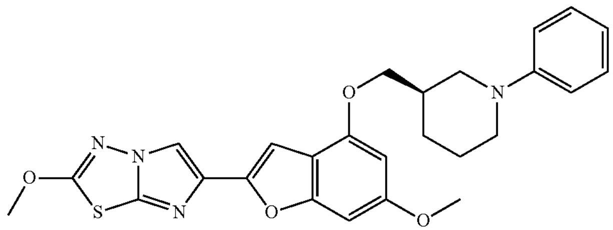 [SMILES: COc1cc(OC[C@@H]2CCCN(c3ccccc3)C2)c2cc(-c3cn4nc(OC)sc4n3)oc2c1] | C26H27N4O4S | 491.1748 | 2.287/C | 491.1776 | 1H NMR (400 MHz, DMSO-d6) δ ppm 8.38 (s, 1 H), 7.14-7.25 (m, 2 H), 6.98 (s, 1 H), 6.95 (d, J = 8.2 Hz, 2 H), 6.81 (s, 1 H), 6.74 (t, J = 7.2 Hz, 1 H), 6.46 (d, J = 1.6 Hz, 1 H), 4.21 (s, 3 H), 4.08 (d, J = 6.3 Hz, 2 H), 3.80 (s, 3 H), 3.75 (dd, J = 11.9, 2.9 Hz, 1 H), 3.58 (d, J = 12.5 Hz, 1 H), 2.68-2.83 (m, 2 H), 2.10-2.24 (m, 1 H), 1.90 (dd, J = 12.3, 3.7 Hz, 1 H), 1.78 (dt, J = 12.9, 3.7 Hz, 1 H), 1.62 (q, J = 11.9 Hz, 1 H), 1.29-1.43 (m, 1 H) |
| 54 | 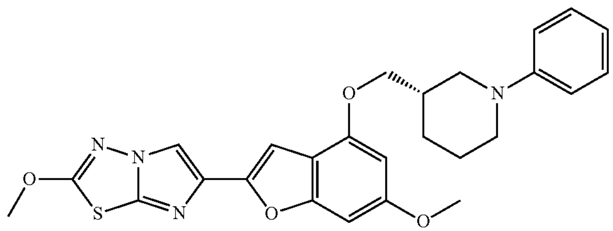 [SMILES: COc1cc(OC[C@H]2CCCN(c3ccccc3)C2)c2cc(-c3cn4nc(OC)sc4n3)oc2c1] | C26H27N4O4S | 491.1748 | 2.295/C | 491.1777 | 1H NMR (400 MHz, DMSO-d6) δ ppm 8.38 (s, 1 H), 7.14-7.25 (m, 2 H), 6.98 (s, 1 H), 6.95 (d, J = 8.2 Hz, 2 H), 6.81 (s, 1 H), 6.74 (t, J = 7.2 Hz, 1 H), 6.46 (d, J = 2.0 Hz, 1 H), 4.21 (s, 3 H), 4.08 (dd, J = 6.7 Hz, 2 H), 3.80 (s, 3 H), 3.75 (d, J = 11.0 Hz, 1 H), 3.58 (d, J = 11.7 Hz, 1 H), 2.68-2.82 (m, 2 H), 2.17 (t, J = 9.4 Hz, 1 H), 1.90 (dd, J = 12.5, 3.1 Hz, 1 H), 1.71-1.83 (m, 1 H), 1.63 (q, J = 11.1 Hz, 1 H), 1.28-1.44 (m, 1 H) |
| 55 | racemate | C26H26ClN4O4S | 525.1358 | 2.367/C | 525.1387 | 1H NMR (400 MHz, DMSO-d6) δ ppm 8.33 (s, 1 H), 7.15-7.26 (m, 2 H), 6.92-7.01 (m, J = 9.0 Hz, 2 H), 6.74-6.80 (m, 1 H), 6.64 (s, 1 H), 6.38 (d, J = 2.0 Hz, 1 H), 4.36 (d, J = 3.1 Hz, 1 H), 4.10-4.27 (m, 5 H), 3.77 (s, 3 H), 3.43 (d, J = 13.3 Hz, 1 H), 3.00-3.13 (m, 1 H), 1.90-2.00 (m, 1 H), 1.53-1.83 (m, 5 H) |

| Ex. | Structure | Formula [M + H]⁺ | Calc. [M + H]⁺ m/z | HPLC RT (Min)/ Method | LCMS [M + H]⁺ m/z | NMR |
|---|---|---|---|---|---|---|
| 56 | 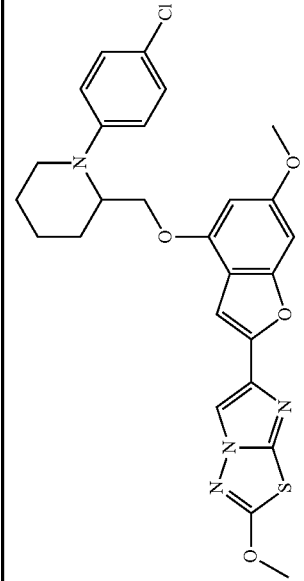 Enantiomer A from chiral separation of Example 55[1] | $C_{26}H_{26}ClN_4O_4S$ | 525.1358 | 1.982/ see footnote 1 | 525.1 | ¹H NMR (400 MHz, CDCl₃) δ ppm 7.84 (s, 1H), 7.22-7.13 (m, 2H), 6.93-6.85 (m, 2H), 6.81 (d, J = 0.7 Hz, 1H), 6.65 (d, J = 0.9 Hz, 1H), 6.19 (d, J = 2.0 Hz, 1H), 4.24 (dd, J = 4.8, 2.6 Hz, 2H), 4.16-4.04 (m, 2H), 3.42-3.32 (m, 1H), 3.11-2.99 (m, 1H), 2.11-2.00 (m, 1H), 1.97-1.86 (m, 1H), 1.81 (d, J = 4.4 Hz, 1H), 1.67 (d, J = 4.0 Hz, 4H), 1.56 (br. s., 4H) |
| 57 | 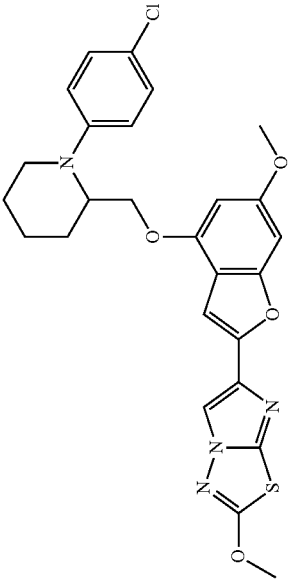 Enantiomer B from chiral separation of Example 55[2] | $C_{26}H_{26}ClN_4O_4S$ | 525.1358 | 1.982/ see footnote 2 | 525.1 | ¹H NMR (400 MHz, CDCl₃) 7.84 (s, 1H), 7.21-7.15 (m, 2H), 6.92-6.86 (m, 2H), 6.81 (d, J = 0.4 Hz, 1H), 6.65 (d, J = 1.1 Hz, 1H), 6.19 (d, J = 2.0 Hz, 1H), 4.24 (dd, J = 6.2, 3.5 Hz, 2H), 4.15-4.05 (m, 2H), 3.41-3.33 (m, 1H), 3.09-2.99 (m, 1H), 2.10-2.01 (m, 1H), 1.92 (td, J = 11.4, 6.5 Hz, 1H), 1.81 (d, J = 4.4 Hz, 1H), 1.67 (d, J = 4.2 Hz, 4H), 1.56 (br. s., 4H) |
| 58 | 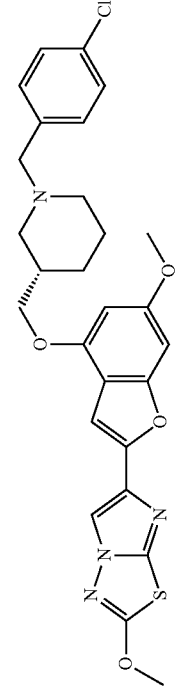 | $C_{27}H_{28}ClN_4O_4S$ | 539.14 | 2.293/C | 539.2 | ¹H NMR (400 MHz, DMSO-d6) δ ppm 8.37 (s, 1 H), 7.21-7.42 (m, 4 H), 6.86 (s, 1 H), 6.79 (s, 1 H), 6.40 (s, 1 H), 4.21 (s, 3 H), 3.91-4.06 (m, 2 H), 3.79 (s, 3 H), 3.40-3.54 (m, 2 H), 2.90 (d, J = 10.2 Hz, 1 H), 2.67 (br. s., 1 H), 1.87-2.15 (m, 3 H), 1.79 (d, J = 12.1 Hz, 1 H), 1.59-1.72 (m, 1 H), 1.43-1.59 (m, 1 H), 1.10-1.26 (m, 1 H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 59 | 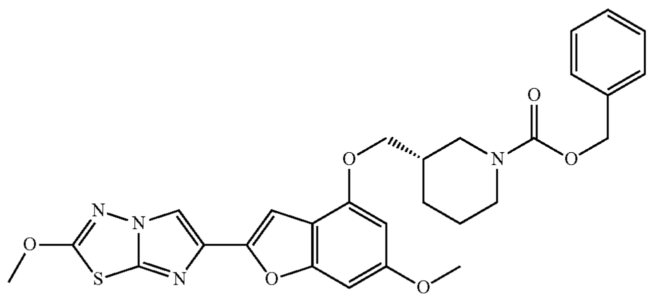 [SMILES: COc1cc(OC[C@H]2CCCN(C(=O)OCc3ccccc3)C2)c2cc(-c3cn4nc(OC)sc4n3)oc2c1] | C28H29N4O6S | 549.17 | 2.648/C | 549.2 | 1H NMR (400 MHz, DMSO-d6) δ ppm 1.30-1.50 (m, 2 H) 1.62-1.75 (m, 1 H) 1.87 (d, J = 10.56 Hz, 1 H) 1.92-2.06 (m, 1 H) 2.89-3.03 (m, 1 H) 3.80 (s, 3 H) 3.86 (br. s., 1 H) 3.92-4.06 (m, 2 H) 4.11 (br. s., 1 H) 4.21 (s, 3 H) 5.07 (br. s., 2 H) 6.43 (d, J = 1.57 Hz, 1 H) 6.77-6.85 (m, 1 H) 6.92 (s, 1 H) 7.33 (br. s., 5 H) 8.37 (s, 1 H) |
| 60 | 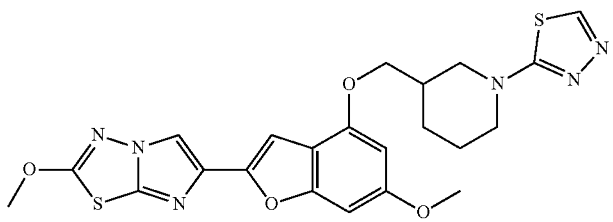 [SMILES: COc1cc(OCC2CCCN(c3nncs3)C2)c2cc(-c3cn4nc(OC)sc4n3)oc2c1] | C22H23N6O4S2 | 499.1217 | 2.558/C | 499.1216 | 1H NMR (400 MHz, DMSO-d6) δ ppm 8.78 (s, 1 H), 8.38 (s, 1 H), 6.97 (s, 1 H), 6.82 (s, 1 H), 6.46 (d, J = 1.6 Hz, 1 H), 4.21 (s, 3 H), 3.97-4.15 (m, 3 H), 3.71-3.85 (m, 4 H), 3.09-3.27 (m, 2 H), 2.11-2.27 (m, 1 H), 1.87-1.99 (m, 1 H), 1.74-1.87 (m, 1 H), 1.54-1.73 (m, 1 H), 1.36-1.54 (m, 1 H) |
| 61 | 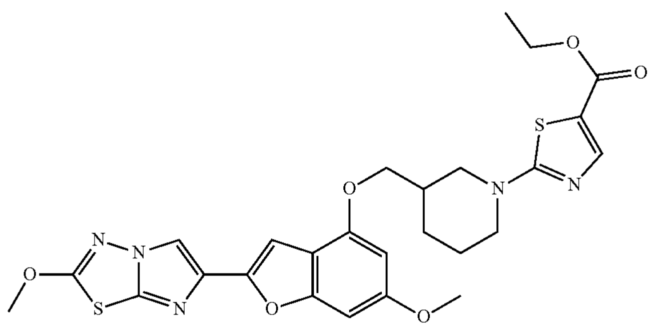 [SMILES: CCOC(=O)c1cnc(N2CCCC(COc3cc(OC)cc4oc(-c5cn6nc(OC)sc6n5)cc34)C2)s1] | C26H28N5O6S2 | 570.1476 | 2.706/C | 570.1479 | 1H NMR (400 MHz, DMSO-d6) δ ppm 8.38 (s, 1 H), 7.84 (s, 1 H), 6.97 (s, 1 H), 6.79-6.84 (m, 1 H), 6.45 (d, J = 2.0 Hz, 1 H), 4.15-4.25 (m, 5 H), 3.99-4.15 (m, 3 H), 3.88 (d, J = 13.7 Hz, 1 H), 3.80 (s, 3 H), 3.13-3.27 (m, 2 H), 2.15 (br. s., 1 H), 1.87-1.97 (m, 1 H), 1.76-1.87 (m, 1 H), 1.42-1.69 (m, 2 H), 1.23 ppm (t, J = 7.0 Hz, 3 H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 62 | (Structure with Br-thiazole) | $C_{23}H_{23}BrN_5O_4S_2$ | 576.03 578.03 | 2.664/C | 576.0 578.0 | 1H NMR (400 MHz, DMSO-d6) δ ppm 8.38 (s, 1 H), 7.19 (s, 1 H), 6.96 (s, 1 H), 6.82 (d, J = 0.8 Hz, 1 H), 6.45 (d, J = 2.0 Hz, 1 H), 4.21 (s, 3 H), 3.92-4.13 (m, 3 H), 3.80 (s, 3 H), 3.72 (d, J = 12.5 Hz, 1 H), 2.97-3.16 (m, 2 H), 2.06-2.21 (m, 1 H), 1.85-1.98 (m, 1 H), 1.78 (dt, J = 13.1, 3.6 Hz, 1 H), 1.51-1.67 (m, 1 H), 1.36-1.51 (m, 1 H) |
| 63 | (Structure with Cl-pyridine) racemate | $C_{25}H_{25}ClN_5O_4S$ | 526.1310 | 2.517/C | 526.1310 | 1H NMR (400 MHz, DMSO-d6) δ ppm 8.39 (s, 1 H), 8.09 (d, J = 2.3 Hz, 1 H), 7.55 (dd, J = 9.2, 2.5 Hz, 1 H), 6.99 (s, 1 H), 6.88 (d, J = 9.0 Hz, 1 H), 6.81 (s, 1 H), 6.41-6.48 (m, 1 H), 4.32 (dd, J = 13.1, 2.9 Hz, 1 H), 4.21 (s, 3 H), 4.10 (d, J = 13.3 Hz, 1 H), 4.04 (d, J = 6.3 Hz, 2 H), 3.80 (s, 3 H), 2.84-3.03 (m, 2 H), 1.97-2.12 (m, 1 H), 1.87-1.97 (m, 1 H), 1.69-1.82 (m, 1 H), 1.37-1.61 (m, 2 H) |
| 64 | (Structure with Cl-pyridine) Enantiomer A from chiral separation of Example 63[3] | $C_{25}H_{25}ClN_5O_4S$ | 526.1310 | 2.190/ see footnote 3 | 526.1 | 1H NMR (400 MHz, CDCl3) 8.10 (d, J = 2.6 Hz, 1H), 7.85 (s, 1H), 7.39 (dd, J = 9.1, 2.8 Hz, 1H), 7.07 (s, 1H), 6.68 (d, J = 1.1 Hz, 1H), 6.63 (d, J = 9.0 Hz, 1H), 6.31 (d, J = 1.8 Hz, 1H), 4.25 (dd, J = 12.8, 3.5 Hz, 1H), 4.12 (d, J = 13.0 Hz, 1H), 4.05-3.94 (m, 2H), 3.85 (s, 3H), 3.04-2.97 (m, 1H), 2.94 (dd, J = 13.0, 10.1 Hz, 1H), 2.24-2.14 (m, 1H), 2.02-1.92 (m, 1H), 1.81 (dt, J = 13.3, 3.7 Hz, 1H), 1.72-1.57 (m, 4H), 1.50 (td, J = 11.8, 3.7 Hz, 1H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 65 | Enantiomer B from chiral separation of Example 63[4] | C25H25ClN5O4S | 526.1310 | 2.192/ see footnote 4 | 526.1 | 1H NMR (400 MHz, CDCl3) 8.10 (d, J = 2.4 Hz, 1H), 7.85 (s, 1H), 7.39 (dd, J = 9.0, 2.4 Hz, 1H), 7.07 (s, 1H), 6.68 (s, 1H), 6.63 (d, J = 9.2 Hz, 1H), 6.31 (s, 1H), 4.25 (d, J = 13.0 Hz, 1H), 4.12 (d, J = 13.0 Hz, 1H), 4.06-3.94 (m, 2H), 3.85 (s, 3H), 3.05-2.97 (m, 1H), 2.94 (dd, J = 12.9, 10.2 Hz, 1H), 2.19 (d, J = 4.4 Hz, 1H), 1.97 (dd, J = 12.5, 3.1 Hz, 1H), 1.88-1.75 (m, 1H), 1.73-1.56 (m, 4H), 1.55-1.45 (m, 1H) |
| 66 | 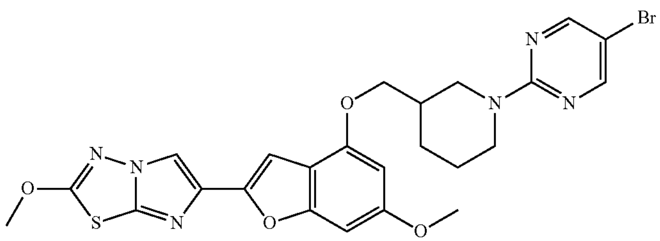 [SMILES: COc1cc(OCC2CCCN(c3ncc(Br)cn3)C2)c2cc(-c3cn4nc(OC)sc4n3)oc2c1] | C24H24BrN6O4S | 571.0758 573.0740 | 2.730/C | 571.0767 573.0752 | 1H NMR (400 MHz, DMSO-d6) δ ppm 8.44 (s, 2 H), 8.39 (s, 1 H), 6.96 (d, J = 0.8 Hz, 1 H), 6.81 (d, J = 0.8 Hz, 1 H), 6.44 (d, J = 2.0 Hz, 1 H), 4.65 (dd, J = 13.1, 3.7 Hz, 1 H), 4.43 (d, J = 12.9 Hz, 1 H), 4.21 (s, 3 H), 3.98-4.09 (m, 2 H), 3.80 (s, 3 H), 2.95-3.11 (m, 2 H), 1.97-2.07 (m, 1 H), 1.87-1.97 (m, 1 H), 1.71-1.83 (m, 1 H), 1.47 (t, J = 9.6 Hz, 2 H) |
| 67 | 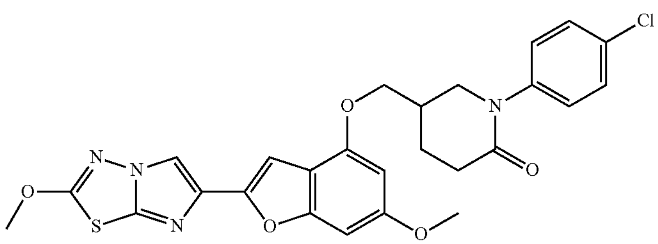 [SMILES: COc1cc(OCC2CCC(=O)N(c3ccc(Cl)cc3)C2)c2cc(-c3cn4nc(OC)sc4n3)oc2c1] | C26H24ClN4O5S | 539.1150 | 2.575/C | 539.1172 | 1H NMR (400 MHz, CDCl3) δ ppm 7.85 (s, 1 H), 7.34-7.40 (m, 2 H), 7.20-7.25 (m, 2 H), 6.98 (s, 1 H), 6.70 (s, 1 H), 6.31 (d, J = 2.0 Hz, 1 H), 4.22 (s, 3 H), 4.17 (dd, J = 9.2, 4.9 Hz, 1 H), 3.99-4.07 (m, 1 H), 3.81-3.90 (m, 4 H), 3.69 (dd, J = 11.9, 9.6 Hz, 1 H), 2.57-2.78 (m, 3 H), 2.10-2.20 (m, 1 H), 1.80-1.95 (m, 1 H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 68 | 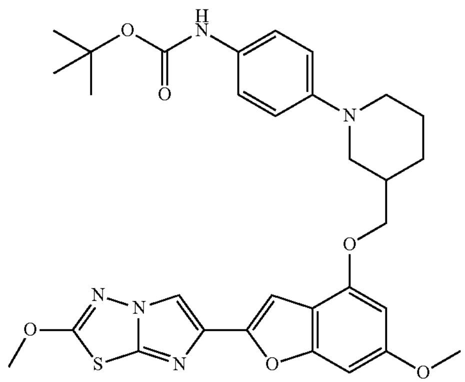 | C31H36N5O6S | 606.2381 | 2.367/C | 606.2411 | 1H NMR (400 MHz, DMSO-d6) δ ppm 9.01 (br. s., 1 H), 8.38 (s, 1 H), 7.19-7.37 (m, J = 8.2 Hz, 2 H), 6.97 (s, 1 H), 6.82-6.91 (m, J = 9.0 Hz, 2 H), 6.81 (s, 1 H), 6.45 (d, J = 2.0 Hz, 1 H), 4.20 (s, 3 H), 4.07 (d, J = 6.3 Hz, 2 H), 3.80 (s, 3 H), 3.62 (d, J = 9.0 Hz, 1 H), 3.45 (d, J = 12.1 Hz, 1 H), 2.56-2.68 (m, 2 H), 2.10-2.24 (m, 1 H), 1.82-1.94 (m, 1 H), 1.71-1.82 (m, 1 H), 1.55-1.71 (m, 1 H), 1.45 (s, 9 H), 1.20-1.39 (m, 1 H) |
| 69 | 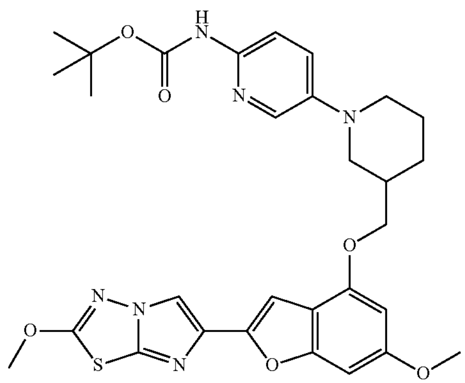 | C30H34N6O6S | 607.2333 | 2.564/A | 607.2304 | 1H NMR (400 MHz, DMSO-d6) δ ppm 9.38 (s, 1 H), 8.38 (s, 1 H), 7.95 (d, J = 3.1 Hz, 1 H), 7.60 (d, J = 9.0 Hz, 1 H), 7.35-7.43 (m, 1 H), 6.99 (s, 1 H), 6.81 (s, 1 H), 6.46 (d, J = 2.0 Hz, 1 H), 4.20 (s, 3 H), 4.07 (d, J = 6.7 Hz, 2 H), 3.80 (s, 3 H), 3.68 (dd, J = 12.7, 3.7 Hz, 1 H), 3.51 (d, J = 12.5 Hz, 2 H), 2.70-2.80 (m, 1 H), 2.11-2.25 (m, 1 H), 1.84-1.96 (m, 1 H), 1.71-1.84 (m, 1 H), 1.57-1.71 (m, 1 H), 1.45 (s, 9 H), 1.30-1.40 (m, 1 H) |

-continued

| Ex. | Structure | Formula [M + H]⁺ | Calc. [M + H]⁺ m/z | HPLC RT (Min)/ Method | LCMS [M + H]⁺ m/z | NMR |
|---|---|---|---|---|---|---|
| 70 | 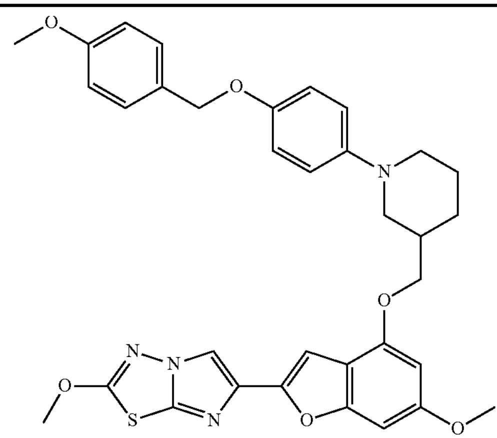 | $C_{34}H_{35}N_4O_6S$ | 627.2272 | 2.445/C | 627.2212 | ¹H NMR (400 MHz, DMSO-d6) δ ppm 8.38 (s, 1 H), 7.34 (d, J = 8.6 Hz, 2 H), 6.83-7.00 (m, 7 H), 6.81 (d, J = 0.8 Hz, 1 H), 6.45 (d, J = 2.0 Hz, 1 H), 4.92 (s, 2 H), 4.20 (s, 3 H), 4.07 (d, J = 6.7 Hz, 2 H), 3.80 (s, 3 H), 3.74 (s, 3 H), 3.57 (dd, J = 11.5, 3.3 Hz, 1 H), 3.35-3.43 (m, 1 H), 2.56-2.66 (m, 2 H), 2.18 (t, J = 10.0 Hz, 1 H), 1.83-1.93 (m, 1 H), 1.72-1.83 (m, 1 H), 1.56-1.72 (m, 1 H), 1.30 (qd, J = 12.2, 2.9 Hz, 1 H) |
| 71 | 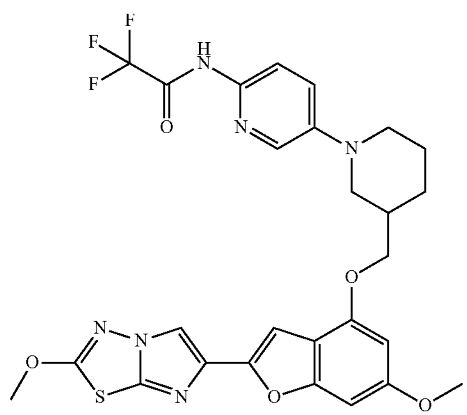 | $C_{27}H_{26}F_3N_6O_5S$ | 603.1632 | 2.464/C | 603.1638 | ¹H NMR (400 MHz, DMSO-d6) δ ppm 11.69 (br. s., 1 H), 8.38 (s, 1 H), 8.13 (br. s., 1 H), 7.75 (d, J = 8.6 Hz, 1 H), 7.48 (d, J = 8.2 Hz, 1 H), 7.00 (s, 1 H), 6.81 (s, 1 H), 6.46 (s, 1 H), 4.21 (s, 3 H), 4.08 (d, J = 6.3 Hz, 2 H), 3.74-3.87 (m, 4 H), 3.66 (d, J = 11.0 Hz, 1 H), 2.74-2.92 (m, 2 H), 2.11-2.26 (m, 1 H), 1.86-2.07 (m, 2 H), 1.80 (d, J = 13.3 Hz, 1 H), 1.55-1.73 (m, 1 H), 1.34-1.52 (m, 2 H) |

| Ex. | Structure | Formula [M + H]+ | Calc. [M + H]+ m/z | HPLC RT (Min)/ Method | LCMS [M + H]+ m/z | NMR |
|---|---|---|---|---|---|---|
| 72 | 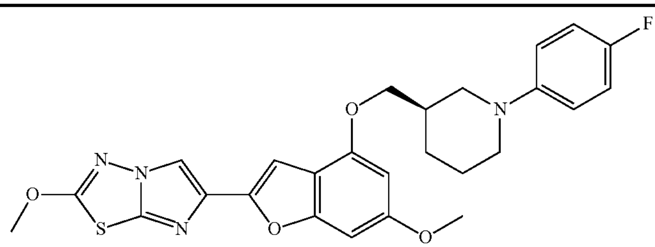 | $C_{26}H_{25}FN_4O_4S$ | 509.1653 | 2.338/C | 509.1690 | $^1$H NMR (400 MHz, DMSO-d6) δ ppm 8.38 (s, 1 H), 7.00-7.08 (m, 2 H), 6.92-7.00 (m, 3 H), 6.78-6.84 (m, 1 H), 6.45 (d, J = 1.6 Hz, 1 H), 4.20 (s, 3 H), 4.07 (d, J = 6.7 Hz, 2 H), 3.80 (s, 3 H), 3.60-3.70 (m, 1 H), 3.48 (d, J = 11.7 Hz, 1 H), 2.61-2.78 (m, 2 H), 2.11-2.25 (m, 1 H), 1.84-1.95 (m, 1 H), 1.72-1.84 (m, 1 H), 1.56-1.72 (m, 1 H), 1.26-1.41 (m, 1 H) |
| 73 | 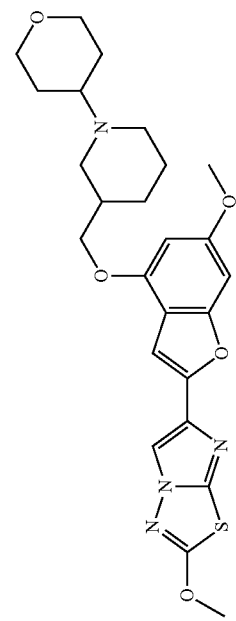 | $C_{25}H_{31}N_4O_5S$ | 499.2010 | 2.233/C | 499.2025 | $^1$H NMR (400 MHz, DMSO-d$_6$) δ ppm 9.16 (br. s., 1 H), 8.33-8.41 (m, 1 H), 6.99-7.07 (m, 1 H), 6.84 (s, 1 H), 6.45 (d, J = 2.0 Hz, 1 H), 4.21 (s, 3 H), 4.13 (dd, J = 9.8, 4.7 Hz, 1 H), 3.93-4.06 (m, 3 H), 3.80 (s, 3 H), 3.64 (d, J = 13.3 Hz, 2 H), 3.33 (t, J = 11.3 Hz, 4 H), 2.85-3.02 (m, 2 H), 1.98 (d, J = 13.3 Hz, 3 H), 1.89 (d, J = 12.1 Hz, 1 H), 1.72 (qd, J = 12.0, 3.9 Hz, 3 H), 1.34-1.49 (m, 1 H) |

-continued

| Ex. | Structure | Formula [M + H]⁺ | Calc. [M + H]⁺ m/z | HPLC RT (Min)/ Method | LCMS [M + H]⁺ m/z | NMR |
|---|---|---|---|---|---|---|
| 74 | (structure) | C₂₅H₂₇N₆O₄S | 507.1809 | 2.368/C | 507.1808 | ¹H NMR (400 MHz, DMSO-d6) δ ppm 8.31 (s, 1 H), 7.90 (dd, J = 9.8, 2.7 Hz, 1 H), 7.41 (br. s., 1 H), 7.30 (br. s., 1H), 6.94 (s, 1 H), 6.87 (d, J = 9.8 Hz, 1 H), 6.75 (d, J = 0.8 Hz, 1 H), 6.38 (d, J = 2.0 Hz, 1 H), 4.14 (s, 2 H), 3.95-4.04 (m, 2 H), 3.73 (s, 3 H), 3.48 (dd, J = 11.5, 3.3 Hz, 2 H), 3.30-3.37 (m, 2 H), 2.51-2.64 (m, 2 H), 2.05-2.18 (m, 1 H), 1.83 (dd, J = 8.8, 3.7 Hz, 1 H), 1.68-1.78 (m, 1 H), 1.51-1.66 (m, 1 H), 1.21-1.34 (m, 1 H) |

¹Example 56 was obtained via chiral separation of Example 55 under following conditions (peak 1): Column: Chiralcel OD-H, 21 × 250 mm, 5 micron; Mobile Phase: 25% (1:1) IPA:ACN/75% CO₂; Flow Conditions: 45 mL/min, 100 Bar, 40° C.; Detector Wavelength: 304 nm; Injection Details: 0.5 mL of 9 mg/mL (1:1) IPA:ACN + 5% CHCl₃. Chiral analytical data: RT 14.66 min; chiral purity: >99.5%; Instrument: Column: Chiralcel OD-H, 4.6 × 250 mm, 5 micron; Mobile Phase: 25% (1:1) IPA-MeCN/75% CO₂; Flow Conditions: 2 mL/min, 100 Bar, 35° C.; Detector Wavelength: 304 nm; Injection Details: 5 μL of 1 mg/mL in DCM-MeCN-IPA. HPLC conditions: Column: Phenomenex Luna C18 2.0 × 30 mm 3 micron; 40° C., sol. A 10% MeOH - 90% H₂O - 0.1% TFA; sol. B 90% MeOH - 10% H₂O - 0.1% TFA; wavelength 220 nm; flow rate 1 mL/min; gradient time 2 min; start % B = 0%, final % B = 100%, T = 40° C.

²Example 57 was obtained via chiral separation of Example 55 under following conditions (peak 2): Column: Chiralcel OD-H, 21 × 250 mm, 5 micron; Mobile Phase: 25% (1:1) IPA:ACN/75% CO₂; Flow Conditions: 45 mL/min, 100 Bar, 40° C.; Detector Wavelength: 304 nm; Injection Details: 0.5 mL of 9 mg/mL (1:1) IPA: ACN + 5% CHCl₃. Chiral analytical data: RT 17.85 min; chiral purity: >99.5%; Column: Chiralcel OD-H, 4.6 × 250 mm, 5 micron; Mobile Phase: 25% (1:1) IPA-MeCN/75% CO₂; Flow Conditions: 2 mL/min, 100 Bar, 35° C.; Detector Wavelength: 304 nm; Injection Details: 5 μL of 1 mg/mL in DCM-MeCN-IPA. HPLC conditions: Column: Phenomenex Luna C18 2.0 × 30 mm 3 micron; 40° C., sol. A 10% MeOH - 90% H₂O - 0.1% TFA; sol. B 90% MeOH - 10% H₂O - 0.1% TFA; wavelength 220 nm; flow rate 1 mL/min; gradient time 2 min; start % B = 0%, final % B = 100%, T = 40° C.

³Example 64 was obtained via chiral separation of Example 63 under following conditions (peak 1): Column: Chiralcel OD-H, 30 × 250 mm, 5 micron; Mobile Phase: 30% (1:1) IPA-MeCN/70% CO₂; Flow Conditions: 85 mL/min, 100 Bar, 40° C.; Detector Wavelength: 304 nm; Injection Details: 1.0 mL of 10 mg/mL in IPA-MeCN-Formic acid. Chiral analytical data: RT 17.25 min; chiral purity: >99.5%; Column: Chiralcel OD-H, 4.6 × 250 mm, 5 micron; Mobile Phase: 25% (1:1) IPA-MeCN/75% CO₂; Flow Conditions: 2.0 mL/min, 100 Bar, 35° C.; Detector Wavelength: 304 nm; Injection Details: 10 μL of 1 mg/mL in MeCN. HPLC conditions: Column: Phenomenex Luna C18 2.0 × 30 mm 3 micron; 40° C., sol. A 10% MeOH - 90% H₂O - 0.1% TFA; sol. B 90% MeOH - 10% H₂O - 0.1% TFA; wavelength 220 nm; flow rate 1 mL/min; gradient time 2 min; start % B = 0%, final % B = 100%, T = 40° C.

⁴Example 65 was obtained via chiral separation of Example 63 under following conditions (peak 2): Column: Chiralcel OD-H, 30 × 250 mm, 5 micron; Mobile Phase: 30% (1:1) IPA-MeCN/70% CO₂; Flow Conditions: 85 mL/min, 100 Bar, 40° C.; Detector Wavelength: 304 nm; Injection Details: 1.0 mL of 10 mg/mL in IPA-MeCN-Formic acid. Chiral analytical data: RT 24.00 min; chiral purity: >99.5%; Column: Chiralcel OD-H, 4.6 × 250 mm, 5 micron; Mobile Phase: 25% (1:1) IPA-MeCN/75% CO₂; Flow Conditions: 2.0 mL/min, 100 Bar, 35° C.; Detector Wavelength: 304 nm; Injection Details: 10 μL of 1 mg/mL in MeCN. HPLC conditions: Column: Phenomenex Luna C18 2.0 × 30 mm 3 micron; 40° C., sol. A 10% MeOH - 90% H₂O - 0.1% TFA; sol. B 90% MeOH - 10% H₂O - 0.1% TFA; wavelength 220 nm; flow rate 1 mL/min; gradient time 2 min; start % B = 0%, final % B = 100%, T = 40° C.

Biology

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%, 20%, 30%, 40%, 50%, 60%, 70%, 80%, 90%, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, p-selectin or CD40L release, or thrombosis and hemostasis models). The term "PAR4 antagonist" also includes a compound that inhibits both PAR1 and PAR4.

It is desirable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; (h) improved therapeutic index with less propensity for bleeding; and (h) factors that improve manufacturing costs or feasibility.

The term "compound", as used herein, means a chemical, be it naturally-occurring or artificially-derived. Compounds may include, for example, peptides, polypeptides, synthetic organic molecules, naturally occurring organic molecules, nucleic acid molecules, peptide nucleic acid molecules, and components and derivatives thereof.

As used herein, the term "patient" encompasses all mammalian species.

As used herein, the term "subject" refers to any human or nonhuman organism that could potentially benefit from treatment with a PAR4 antagonist. Exemplary subjects include human beings of any age with risk factors for cardiovascular disease, or patients that have already experienced one episode of cardiovascular disease. Common risk factors include, but are not limited to, age, male sex, hypertension, smoking or smoking history, elevation of triglycerides, elevation of total cholesterol or LDL cholesterol.

In some embodiments, the subject is a species having a dual PAR1/PAR4 platelet receptor repertoire. As used herein, the term "dual PAR1/PAR4 platelet receptor repertoire" means that a subject expresses PAR1 and PAR4 in platelets or their precursors. Exemplary subjects having a dual PAR1/PAR4 platelet receptor repertoire include human beings, non-human primates, and guinea pigs.

In other embodiments, the subject is a species having a dual PAR3/PAR4 platelet receptor repertoire. As used herein, the term "dual PAR3/PAR4 platelet receptor repertoire" means that a subject expresses PAR3 and PAR4 in platelets or their precursors. Exemplary subjects having a dual PAR3/PAR4 platelet receptor repertoire include rodents and rabbits.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid *communis*, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005).) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular weight heparin preparations have been approved by the FDA for these indications.

The term "pharmaceutical composition", as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy*, 20th Edition, Mack Publishing Co., Easton, Pa. (2000).

The invention includes administering to a subject a pharmaceutical composition that includes a compound that binds to PAR4 and inhibits PAR4 cleavage and/or signaling (referred to herein as a "PAR4 antagonist" or "therapeutic compound").

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The preferred dose of the PAR4 antagonist is a biologically active dose. A biologically active dose is a dose that will inhibit cleavage and/or signaling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS), Western blot or ELISA analysis using PAR4 cleavage sensitive antibodies. Alternatively, the biological activity of PAR4 is measured by assessing cellular signaling elicited by PAR4 (e.g., calcium mobilization or other second messenger assays).

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods known to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of Formula I, IA, IB, IC or ID, or preferably a compound selected from one of the examples, more preferably a compound selected from Examples 3 to 114, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

The activity of the PAR4 antagonists of the present invention can be measured in a variety of in vitro assays. Exemplary assays are shown in the Examples below.

The FLIPR assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored. See, e.g., Example A.

AYPGKF is a known PAR4 agonist. An alternative PAR4 agonist is H-Ala-Phe(4-F)-Pro-Gly-Trp-Leu-Val-Lys-Asn-Gly-$NH_2$. As shown in Example B below, H-Ala-Phe(4-F)-Pro-Gly-Trp-Leu-Val-Lys-Asn-Gly-$NH_2$ was validated as a PAR4 agonist in the FLIPR assay. A side-by-side comparison of the $IC_{50}$ values of ~180 compounds were performed using AYPGKF versus H-Ala-Phe(4-F)-Pro-Gly-Trp-Leu-Val-Lys-Asn-Gly-$NH_2$. The results demonstrated a strong correlation between the two assays. Additionally, H-Ala-Phe(4-F)-Pro-Gly-Trp-Leu-Val-Lys-Asn-Gly-$NH_2$ has improved agonist activity as compared to AYPGKF with an $EC_{50}$ that is 10 fold lower than the $EC_{50}$ for AYPGKF in the FLIPR assay. H-Ala-Phe(4-F)-Pro-Gly-Trp-Leu-Val-Lys-Asn-Gly-$NH_2$ can be synthesized using methods well known to those of skill in the art.

The FLIPR assay can also be used as a counterscreen to test agonist activity or PAR1 antagonist activity in a cell line that expresses both PAR1 and PAR4. The PAR1 antagonist activity can be tested by the ability of the compound to inhibit calcium mobilization induced by the PAR1 agonist peptide SFLLRN or other PAR1 agonist peptides.

The compounds of the current invention can be tested in vitro for their ability to inhibit platelet aggregation induced by gamma-thrombin as shown in Example C. Gamma-thrombin, a proteolytic product of alpha-thrombin which no longer interacts with PAR1, selectively cleaves and activates PAR4 (Soslau, G. et al., "Unique pathway of thrombin-induced platelet aggregation mediated by glycoprotein Ib", *J. Biol. Chem.*, 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, PAR1 agonist peptide, ADP, or thromboxane analogue U46619.

Example D is an alpha-thrombin-induced platelet aggregation assay. Alpha-thrombin activates both PAR1 and PAR4. The ability of PAR4 antagonists of the present invention to inhibit alpha-thrombin-induced platelet aggregation can be measured using a standard optical aggregometer and the method described.

Example E is a tissue factor-induced platelet aggregation assay. The conditions in this assay mimic the physiological events during thrombus formation. In this assay, platelet aggregation in human PRP was initiated by the addition of tissue factor and $CaCl_2$). Tissue factor, the initiator of the extrinsic coagulation cascade, is highly elevated in human atherosclerotic plaque. Exposure of blood to tissue factor triggers a robust generation of thrombin and induces the formation of thrombi. The ability of PAR4 antagonists of the present invention to inhibit tissue factor-induced platelet aggregation can be measured using the method described.

The efficacy of the PAR4 antagonists of the present invention in preventing thrombosis can also be measured in a variety of in vivo assays. Exemplary mammals that can provide models of thrombosis and hemostasis to test the effectiveness of the PAR4 antagonists of the present invention as antithrombotic agents include, but are not limited to, guinea pigs and primates. Relevant efficacy models include, but are not limited to, electrolytic injury-induced carotid artery thrombosis, $FeCl_3$-induced carotid artery thrombosis and arteriovenous-shunt thrombosis. Models of kidney bleeding time, renal bleeding time and other bleeding time measurements can be used to assess the bleeding risk of the antithrombotic agents described in the current invention. Example G describes an in vivo model of arterial thrombosis in cynolmolgus monkeys. Compounds of the present invention can be tested in this model for their ability to inhibit thrombus formation induced by electrolytic injury of the carotid artery. Demonstration of efficacy in this model supports the utility of PAR4 antagonists of the present invention for treatment of thromboembolic diseases.

Assays

Materials
1) PAR1 and PAR4 Agonist Peptides

SFFLRR is a known high affinity PAR1 selective agonist peptide. (Reference: Seiler, S. M., "Thrombin receptor antagonists", *Seminars in Thrombosis and Hemostasis*, 22(3):223-232 (1996).) The PAR4 agonist peptides AYPGKF and H-Ala-Phe(4-F)-Pro-Gly-Trp-Leu-Val-Lys-Asn-Gly-$NH_2$ were synthesized. H-Ala-Phe(4-F)-Pro-Gly-Trp-Leu-Val-Lys-Asn-Gly-$NH_2$ showed improved PAR4 agonist activity over AYPGKF in the FLIPR assay ($EC_{50}$ of 8 µM for H-Ala-Phe(4-F)-Pro-Gly-Trp-Leu-Val-Lys-Asn-Gly-$NH_2$ and 60 µM for AYPGKF) and in washed platelet aggregation assay ($EC_{50}$ of 0.9 µM for H-Ala-Phe(4-F)-Pro-Gly-Trp-Leu-Val-Lys-Asn-Gly-$NH_2$ and 12 µM for AYPGKF).
2) PAR4 Expressing Cells HEK293 cells stably expressing PAR4 were generated by a standard method of transfection of human F2R23 cDNA expression vector or by RAGE technology from Athersys Inc. (Cleveland, Ohio) and selected based on PAR4 protein expression of mRNA expression. Those cells demonstrated functional responses to PAR4 agonist peptide-induced intracellular calcium elevation using FLIPR® (Fluorometric Imaging Plate Reader; Molecular Devices Corp.). These cells express endogenous PAR1 and can elicit calcium signal upon stimulation with PAR1 agonist peptide. Cells were grown in Dulbecco's Modified Eagle's Medium (DMEM) (Invitrogen, Carlsbad, Calif.), 10% FBS, 1% PSG, 3 µg/ml puromycin and 25 nM Methotrexate) at 37° C. with 5% $CO_2$.
3) Preparation of Platelet Rich Plasma (PRP)

Human blood was collected in 3.8% sodium citrate at a ratio of 1 ml per 9 ml blood. The platelet rich plasma was isolated by centrifugation at 170 g for 14 minutes.
4) Preparation of Washed Platelets (WP)

Human blood was collected in ACD (85 mM tri-sodium citrate, 78 mM citric acid, 110 mM D-glucose, pH 4.4) at a ratio of 1.4 ml per 10 ml blood. PRP was isolated by centrifugation at 170 g for 14 minutes and platelets were further pelleted by centrifugation at 1300 g for 6 minutes. Platelets were washed once with 10 ml ACD containing 1 mg/ml bovine serum albumin. Platelets were resuspended at ~$2.5 \times 10^8$/ml in Tyrode's Buffer (137 mM NaCl, 2 mM KCl, 1.0 mM $MgCl_2$, 1 mM $CaCl_2$, 5 mM glucose, 20 mM HEPES pH 7.4).

Example A

FLIPR Assay in PAR4-Expressing HEK293 Cells

FLIPR-based calcium mobilization assay in HEK293 cells was used to measure PAR4 antagonism, agonism, and selectivity against PAR1. The activity of the PAR4 antagonists of the present invention were tested in PAR4 expressing cells by monitoring H-Ala-Phe(4-F)-Pro-Gly-Trp-Leu-Val-Lys-Asn-Gly-$NH_2$-induced intracellular calcium mobilization. Counter screens for agonist activity and PAR1 antagonist activity were also performed. Briefly, PAR1/PAR4-expressing HEK293 cells were grown in DMEM (Life Technology, Grand Island, N.Y.) containing 10% heat-inactivated FBS, 1% Penicillin-Streptomycin, 10 µg/mL blasticidin, and 100 µg/mL Zeocin at 37° C. with 5% $CO_2$. Cells were plated overnight prior to the experiment in a black 384-well Purecoat Amine clear bottom plate (Becton Dickinson Biosciences, San Jose, Calif.) at 10,000 cells/well in 30 µL growth medium and incubated in a humidified chamber at 37° C. with 5% $CO_2$ overnight. Prior to compound addition, the cell medium was replaced with 40 µL of 1x calcium and magnesium-containing Hank's Balanced Saline Solution (HBSS) (with 20 mM HEPES) and 1:1000 diluted fluorescent calcium indicator (Codex Biosolutions, Gaithersburg, Md.). After a 30 minute incubation period at 37° C. and a further 30 minute incubation and equilibration period at room temperature, 20 µL test compound (diluted in 1xHBSS buffer) was added at various concentrations at 0.17% dimethyl sulfoxide (DMSO) final concentration. Changes in fluorescence intensity were measured using a Functional Drug Screening System (FDSS, Hamamatsu, Japan) to determine agonist activities. The cells were then incubated for 30 minutes at room temperature followed by addition of 20 µL of agonist peptide for antagonist activity measurement. The PAR4 agonist peptide (H-Ala-Phe(4-F)-Pro-Gly-Trp-Leu-Val-Lys-Asn-Gly-$NH_2$) and the PAR1 agonist peptide (SFFLRR) were routinely tested to ensure a proper response at the $EC_{50}$ value in the assay (~5 µM for PAR4 agonist peptide and ~2 µM for PAR1 agonist peptide). Compound potency was derived from 11-point concentration-response curves.

Example B

Validation of H-Ala-Phe(4-F)-Pro-Gly-Trp-Leu-Val-Lys-Asn-Gly-$NH_2$ as a PAR4 Agonist To validate H-Ala-Phe(4-F)-Pro-Gly-Trp-Leu-Val-Lys-Asn-Gly-$NH_2$ as a PAR4 agonist in the FLIPR assay, side-by-side comparison of the $IC_{50}$ values of ~180 compounds were performed using AYPGKF versus H-Ala-Phe(4-F)-Pro-Gly-Trp-Leu-Val-Lys-Asn-Gly-$NH_2$. The results demonstrated a strong correlation between the two assays (Spearman's rank correlation coefficient rho=0.7760, p<0.0001). The relevance of the FLIPR assay in the HEK293 cells was confirmed by a direct assay connectivity to the washed platelet assay. The $IC_{50}$ values of ~200 compounds from AYPGKF FLIPR assay was strongly correlated to that from AYPGKF washed platelet aggregation assay (Spearman's rank correlation coefficient rho=0.836, p<0.001). Similar results were obtained comparing FLIPR and washed platelet data using H-Ala-Phe(4-F)-Pro-Gly-Trp-Leu-Val-Lys-Asn-Gly-NH$_2$.

Example C

Gamma Thrombin Induced Platelet Aggregation Assays

The ability of the compounds of the current invention to inhibit platelet aggregation induced by gamma-thrombin was tested in a 96-well microplate aggregation assay format. Briefly, PRP or washed platelet suspension (100 μl) was pre-incubated for 5 minutes at room temperature with varying concentrations of compounds. Aggregation was initiated by ~10-50 nM gamma thrombin (Haematologic Technologies, Essex Junction, Vt.), which was titrated daily to achieve 80% platelet aggregation. Refludan at 1 U/mL (Berlex, Montville, N.J.) was added to the gamma thrombin sample to prevent PAR1 activation induced by residual alpha-thrombin contamination. The plate was then placed into a 37° C. Molecular Devices (Sunnyvale, Calif.) SPECTRAMAX® Plus Plate Reader. The plate was mixed for 10 seconds before the first read and 50 seconds between each read for up to 15 minutes at 405 nM. Data was collected with SOFTMAX® 4.71 software. The plate also included an untreated control sample which served as ODmax, while buffer containing no platelets was the ODmin. Platelet aggregation was determined by subtracting the ODmax from the ODmin for the 100% aggregation value. In experimental samples, the observed transmission was subtracted from the minimum value and then compared to the 100% aggregation value to determine the percentage aggregation. IC$_{50}$ values are determined using Excel Fit software.

The aggregation assays were also employed to test the selectivity of the compound against other platelet receptors by using SFFLRR for PAR1, collagen (Chrono-Log, Havertown, Pa.) for collagen receptors, ADP for P2Y1 and P2Y12 and U46619 (Cayman Chemical, Ann Arbor, Mich.) for thromboxane receptors.

Example D

Alpha-Thrombin Induced Platelet Aggregation Assays

The ability of a PAR4 antagonist compound to inhibit platelet aggregation induced by alpha-thrombin can be tested using human washed platelets. The compound is pre-incubated with washed platelets for 20 min. Aggregation is initiated by addition of 1.5 nM alpha-thrombin (Haematologic Technologies, Essex Junction, Vt.) to 300 μl of washed platelets at stirring speed of 1000 rpm. Platelet aggregation is monitored using an Optical Aggregometer (Chrono-Log, Havertown, Pa.) and the area under the curve (AUC) at 6 min is measured. IC$_{50}$ is calculated using vehicle control as 0% inhibition.

Example E

Tissue Factor-Induced Platelet Aggregation Assay

The ability of PAR1 or PAR4 antagonists to inhibit platelet aggregation induced by endogenous thrombin can be tested in a tissue factor driven aggregation assay. Aggregation is initiated by addition of CaCl$_2$ and recombinant human tissue factor, which results in the generation of thrombin through activation of the coagulation pathway in the plasma. Anticoagulant agents such as corn trypsin inhibitor (Haematologic Technologies, Essex Junction, Vt.) at 50 μg/ml and PEFABLOC® FG (Centerchem, Norwalk, Conn.) are also added to the sample to prevent fibrin clot formation during the time of the study. Platelet aggregation is monitored using standard instrumentation including optical aggregometer or impedance aggregometer.

Example F

The following Table I sets out the results obtained employing various compounds of the invention tested in the FLIPR assay. As indicated above, the FLIPR assay, an in vitro assay, measures the PAR4 antagonist activity of compounds tested as described in Example A.

TABLE 1

| Example # | PAR4 FLIPR IC50 (μM) |
| --- | --- |
| 1 | 0.42 |
| 2 | 9.4 |
| 3 | 1.2 |
| 4 | 460 |
| 5 | 24 |
| 6 | 15 |
| 7 | 16 |
| 8 | 1.4 |
| 9 | 0.95 |
| 10 | 0.39 |
| 11 | 0.74 |
| 12 | 0.42 |
| 13 | 0.55 |
| 14 | 12 |
| 15 | 1.3 |
| 16 | 0.50 |
| 17 | 0.29 |
| 18 | 0.47 |
| 19 | 0.46 |
| 20 | 0.71 |
| 21 | 0.54 |
| 22 | 0.44 |
| 23 | 0.60 |
| 24 | 0.95 |
| 25 | 0.79 |
| 26 | 1.4 |
| 27 | 2.3 |
| 28 | 1.8 |
| 29 | 0.95 |
| 30 | 0.86 |
| 31 | 0.89 |
| 32 | 2.8 |
| 33 | 0.44 |
| 34 | 0.70 |
| 35 | 0.84 |
| 36 | 0.75 |
| 37 | 0.56 |
| 38 | 0.54 |
| 39 | 0.51 |
| 40 | 1.3 |
| 41 | 2.1 |
| 42 | 1.1 |
| 43 | 0.48 |
| 44 | 0.75 |
| 45 | 0.37 |
| 46 | 0.24 |
| 47 | 1.0 |
| 48 | 1.1 |
| 49 | 2.7 |
| 50 | 4.8 |
| 51 | 5.0 |
| 52 | 1.1 |
| 53 | 1.8 |
| 54 | 1.4 |
| 55 | 0.72 |
| 56 | 0.92 |
| 57 | 0.74 |

TABLE 1-continued

| Example # | PAR4 FLIPR IC50 (µM) |
|---|---|
| 58 | 1.4 |
| 59 | 1.2 |
| 60 | 2.7 |
| 61 | 1.5 |
| 62 | 1.9 |
| 63 | 0.86 |
| 64 | 0.82 |
| 65 | 1.0 |
| 66 | 1.4 |
| 67 | 3.3 |
| 68 | 2.1 |
| 69 | 3.2 |
| 70 | 3.5 |
| 71 | 1.3 |
| 72 | 1.4 |
| 73 | 47 |
| 74 | 28 |

Data in Table 1 are reported with two significant figures.

Example G

Cynomolgus Monkey Electrolytic Injury-Induced Carotid Artery Thrombosis Model

Healthy cynomolgus monkeys are used in the study. These monkeys are retired from other pharmacokinetic and pharmacodynamic studies and have at least a 4-week washout period.

On the day of the study, compounds or vehicles are administered orally at 1 to 2 hours before the experiment. Monkeys are then sedated by intramuscular administration of 0.2 mg/kg atropine, 5 mg/kg TELAZOL® (tiletamine/zolazepam) and 0.1 mg/kg hydromorphone to facilitate placement of an endotracheal tube. An intravenous catheter is placed in the left cephalic vein for fluid administration to prevent dehydration. Animals are then administered with an inhalant anesthetic, isoflurane (1-5% to effect) and oxygen, ventilated, and placed on a thermostatically controlled heating pad to maintain the body temperature at 37° C. General anesthesia is maintained at a surgical plane using inhaled isoflurane and oxygen. The left brachial artery is cannulated to record blood pressure and heart rate. Blood pressure and heart rate are monitored to maintain normal vital signs.

The carotid arterial thrombosis model in monkeys is based on a rabbit arterial thrombosis model, as described by Wong et al. (Wong, P. C. et al., "Nonpeptide factor Xa inhibitors: II. Antithrombotic evaluation in a rabbit model of electrically induced carotid artery thrombosis", J. Pharmacol. Exp. Ther., 295:212-218 (2002).) Thrombosis is induced by electrical stimulation of the carotid artery for 5 min at 10 mA using an external stainless-steel bipolar electrode. Carotid blood flow is measured with an appropriately sized TRANSONIC® flow probe and a TRANSONIC® perivascular flowmeter (TS420 Model, Transonic Systems Inc., Ithaca, N.Y.). It is continuously recorded over a 90-min period to monitor thrombosis-induced occlusion. Integrated carotid blood flow is measured by the area under the flow-time curve. It is expressed as percent of total control carotid blood flow, which would result if control blood flow has been maintained continuously for 90 min. In addition, thrombus from the injured artery is removed, blotted twice on a weighing paper to remove residual fluid, and weighed.

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

What is claimed is:
1. A compound of Formula I:

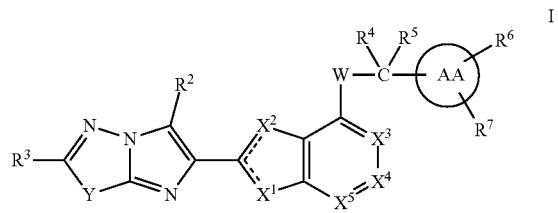

or a stereoisomer, tautomer, pharmaceutically acceptable salt, solvate or prodrug thereof, wherein:

the dashed lines represent double-bonds with the proviso that only one of the two dashed line double bonds exists at the same time;

$X^1$ is O and $X^2$ is =N— or $CR^{1a}$; or
$X^2$ is S and $X^1$ is =N— or $CR^{1a}$; or
$X^1$ is =N— and $X^2$ is O or $NR^{1b}$; or
$X^1$ is $NR^{1b}$ and $X^2$ is $CR^{1a}$; or
$X^1$ is $CR^{1a}$ and $X^2$ is $NR^{1b}$;

$X^3$, $X^4$, and $X^5$ are independently selected from $CR^{1d}$ and =N—;

$R^{1a}$ is selected from the group consisting of H, halo, cyano, $C_1$-$C_3$ alkyl, $C_3$-$C_5$ cycloalkyl, halo-$C_1$-$C_2$alkyl, and $C_1$-$C_3$ alkoxy;

$R^{1b}$ is selected from the group consisting of H, $C_1$-$C_3$ alkyl, $C_3$-$C_5$ cycloalkyl, and halo-$C_1$-$C_2$alkyl;

$R^{1d}$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $OCHF_2$, $OCH_2F$, $C_1$-$C_2$-alkoxy-$C_1$-$C_2$-alkoxy, halo-$C_1$-$C_3$-alkyl, halo-$C_{1-2}$-alkoxy, halo-$C_{1-2}$-alkylthio, benzyloxy substituted (on the phenyl of said benzyl) by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, and —$(CH_2)_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;

n is 1 or 2;

Y is S, O or —$CR^{1e}$=$CR^{1f}$—;

$R^{1e}$ is independently at each occurrence selected from the group consisting of H, halo, cyano, $C_1$-$C_3$ alkyl, $C_3$-$C_5$ cycloalkyl, halo-$C_1$-$C_2$ alkyl, $C_1$-$C_3$ alkoxy, and halo-$C_1$-$C_3$ alkoxy;

$R^{1f}$ is independently at each occurrence selected from the group consisting of H, halo, cyano, $C_1$-$C_3$ alkyl, $C_3$-$C_5$ cycloalkyl, halo-$C_1$-$C_2$ alkyl, $C_1$-$C_3$ alkoxy, and halo-$C_1$-$C_3$ alkoxy;

$R^2$ is H, halo, $C_1$-$C_3$ alkyl, halo-$C_1$-$C_2$ alkyl, $C_1$-$C_3$ alkoxy, halo-$C_1$-$C_3$ alkoxy, CN or $C_3$-$C_5$ cycloalkyl;

$R^3$ is selected from the group consisting of $C_{1-4}$ alkyl, $C_{1-4}$ alkoxy, $C_{1-4}$ alkylthio, $C_{1-2}$ haloalkyl, $C_{1-2}$ haloalkoxy, $C_{1-2}$ haloalkylthio, $C_{3-4}$ cycloalkyl, halo-$C_{3-4}$ cycloalkyl, $C_{1-4}$ alkylamino, di-$C_{1-4}$ alkylamino, ($C_{1-2}$ alkoxy) $C_{1-2}$ alkyl, halo($C_{1-2}$ alkoxy) $C_{1-2}$ alkyl, $C_{2-3}$ alkenyl, $C_{2-3}$ alkynyl, tetrahydrofuran-2-yl, and halo;

W is O or S;

$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;

is selected from the group consisting of: a piperidine ring which may be unsubstituted or substituted with 0-1 $R^6$ and 0-4 $R^7$ substituents; a piperazine ring which may be unsubstituted or substituted with 0-1 $R^6$ and 0-4 $R^7$ substituents; a morpholine ring which may be unsubstituted or substituted with 0-1 $R^6$ and 0-4 $R^7$ substituents; and an azetidine ring which may be unsubstituted or substituted with 0-1 $R^6$ and 0-4 $R^7$ substituents;

$R^6$ is selected from the group consisting of $C_6$-$C_{10}$ aryl, 5-10 membered heteroaryl, 4-8 membered saturated heterocyclic ring, or $C_3$-$C_8$ cycloalkyl ring, wherein each of said $C_6$-$C_{10}$ aryl, 5-10 membered heteroaryl, 4-8 membered saturated heterocyclic ring, or $C_3$-$C_8$ cycloalkyl ring, can be substituted with 0-4 $R^{7a}$ substituents;

$R^7$ is independently selected at each occurrence from the group consisting of halo, $C_1$-$C_4$ alkyl, $C_1$-$C_4$ alkoxy, halo $C_1$-$C_4$ alkyl, halo $C_1$-$C_4$ alkoxy, $C_1$-$C_4$ alkylthio, halo $C_1$-$C_4$ alkylthio, hydroxy, hydroxy $C_1$-$C_4$ alkyl, hydroxy $C_1$-$C_4$ alkoxy, ($C_1$-$C_6$ alkyl)carboxy-, carboxy, —C(O)Oalkyl, —C(O)NH$_2$, —C(O)NHalkyl, —C(O)N-dialkyl, —NH$_2$, (alkyl)amino-, (dialkyl)amino-, —NH-carboxy-$C_1$-$C_6$ alkyl, nitro, cyano, oxo, (haloaryl)alkyl-, $C_3$-$C_6$ cycloalkyl, —S(O)-alkyl, —S(O)-aryl, —S(O)-heteroaryl, —S(O$_2$)alkyl, —S(O$_2$)aryl, —S(O$_2$)heteroaryl, —S(O$_2$)NH$_2$, —S(O$_2$)NHalkyl, —S(O$_2$)N-dialkyl, or if two $R^7$ substituents are attached to the same carbon atom, they may be taken together with the carbon atom to which they are attached to form a $C_3$-$C_6$ cycloalkyl group or a 3-6 membered heterocyclic ring, or if two $R^7$ substituents are attached to adjacent carbon atoms, they may be taken together with the carbon atoms to which they are attached to form a $C_3$-$C_6$ cycloalkyl group or a 3-6 membered heterocyclic ring; and $R^{7a}$ is independently selected at each occurrence from the group consisting of halo, $C_1$-$C_4$ alkyl, $C_1$-$C_4$ alkoxy, halo $C_1$-$C_4$ alkyl, halo $C_1$-$C_4$ alkoxy, $C_1$-$C_4$ alkylthio, halo $C_1$-$C_4$ alkylthio, hydroxy, hydroxy $C_1$-$C_4$ alkyl, hydroxy $C_1$-$C_4$ alkoxy, ($C_1$-$C_6$ alkyl)carboxy-, carboxy, —C(O)Oalkyl, —C(O)NH$_2$, —C(O)NHalkyl, —C(O)N-dialkyl, —NH$_2$, (alkyl)amino-, (dialkyl)amino-, —NHC(O)O—$C_1$-$C_6$ alkyl, —NHC(O)-halo $C_1$-$C_6$ alkyl, nitro, cyano, oxo, $C_3$-$C_6$ cycloalkyl, —S(O)—alkyl, —S(O)-aryl, —S(O)-heteroaryl, —S(O$_2$)alkyl, —S(O$_2$)aryl, —S(O$_2$)heteroaryl, —S(O$_2$)NH$_2$, —S(O$_2$)NHalkyl, —S(O$_2$)N-dialkyl, aryl $C_1$-$C_4$ alkoxy, —C(O)aryl, —C(O)—$C_1$-$C_6$ alkyl, or if two $R^{7a}$ substituents are attached to the same carbon atom, they may be taken together with the carbon atom to which they are attached to form a $C_3$-$C_6$ cycloalkyl group or a 3-6 membered heterocyclic ring, or if two $R^{7a}$ substituents are attached to adjacent carbon atoms, they may be taken together with the carbon atoms to which they are attached to form a $C_3$-$C_6$ cycloalkyl group or a 3-6 membered heterocyclic ring.

2. The compound of claim 1, wherein:

is a piperidine ring which may be unsubstituted or substituted with 0-1 $R^6$ and 0-4 $R^7$ substituents.

3. The compound of claim 1, wherein:

is a piperazine ring which may be unsubstituted or substituted with 0-1 $R^6$ and 0-4 $R^7$ substituents.

4. The compound of claim 1, wherein:

is a morpholine ring which may be unsubstituted or substituted with 0-1 $R^6$ and 0-4 $R^7$ substituents.

5. The compound of claim 1, wherein:

is an azetidine ring which may be unsubstituted or substituted with 0-1 $R^6$ and 0-4 $R^7$ substituents.

6. The compound of claim 1, wherein Y is S.

7. The compound of claim 1, wherein Y is —C═C—.

8. The compound of claim 1, wherein said compound has the formula:

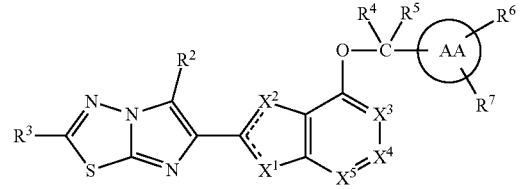

or a stereoisomer, tautomer, pharmaceutically acceptable salt, solvate or prodrug thereof, wherein:

the dashed lines represent double-bonds with the proviso that only one of the two dashed line double bonds exists at the same time;

$X^1$ is O and $X^2$ is ═N— or $CR^{1a}$; or $X^2$ is S and $X^1$ is ═N—; or $X^1$ is ═N— and $X^2$ is O;

$X^3$, $X^4$, and $X^5$ are independently selected from $CR^{1d}$ and N;

$R^{1a}$ if present, is H or Me;

$R^{1d}$ is selected from the group consisting of $C_1$-$C_4$ alkoxy, halo, CN, OCF$_3$, OCHF$_2$, OCH$_2$F, halo-$C_1$-$C_3$-alkyl, or halo-$C_{1-2}$-alkoxy;

R² is H or Me;
R³ is selected from the group consisting of C₁₋₄ alkyl, C₁₋₄ alkoxy, C₁₋₄ alkylthio, C₁₋₂ haloalkyl, C₁₋₂ haloalkoxy, C₁₋₂ haloalkylthio, C₃₋₄ cycloalkyl, halo-C₃₋₄ cycloalkyl; and
R⁴ and R⁵ are independently selected from H, C₁-C₆ alkyl, and C₁-C₄ fluoroalkyl.

9. The compound of claim 1, wherein said compound has the formula:

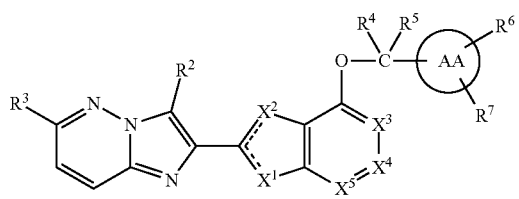

or a stereoisomer, tautomer, pharmaceutically acceptable salt, solvate or prodrug thereof, wherein:
the dashed lines represent double-bonds with the proviso that only one of the two dashed line double bonds exists at the same time;
X¹ is O and X² is =N— or CR^{1a}; or
X² is S and X¹ is =N—; or
X¹ is =N— and X² is O;
X³, X⁴, and X⁵ are independently selected from CR^{1d} and N;
R^{1a} if present, is H or Me;
R^{1d} is selected from the group consisting of C₁-C₄ alkoxy, halo, CN, OCF₃, OCHF₂, OCH₂F, halo-C₁-C₃-alkyl, or halo-C₁₋₂-alkoxy;
R² is H or Me;
R³ is selected from the group consisting of C₁₋₄ alkyl, C₁₋₄ alkoxy, C₁₋₄ alkylthio, C₁₋₂ haloalkyl, C₁₋₂ haloalkoxy, C₁₋₂ haloalkylthio, C₃₋₄ cycloalkyl, halo-C₃₋₄ cycloalkyl; and
R⁴ and R⁵ are independently selected from H, C₁-C₆ alkyl, and C₁-C₄ fluoroalkyl.

10. The compound of claim 1, wherein said compound has the formula:

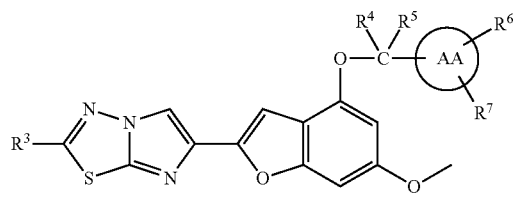

or a stereoisomer, tautomer, pharmaceutically acceptable salt, solvate or prodrug thereof, wherein:
R³ is selected from the group consisting of methyl, ethyl, methoxy, fluoroethyl, and difluoroethyl;
R⁴ and R⁵ are independently selected from H, and methyl; and AA is a piperidine, piperazine, or morpholine ring which may be unsubstituted or substituted at any open carbon atom valence with 0-1 R⁶ and 0-4 R⁷ substituents.

11. The compound of claim 1, wherein:
R⁶ is phenyl, 5-membered heteroaryl, 6-membered heteroaryl, 5-membered heterocycle, or 6-membered heterocycle, each of which can be substituted with independently selected 0-3 R^{7a} substituents.

12. The compound as defined in claim 1, wherein the compound is selected from one of the following compounds:

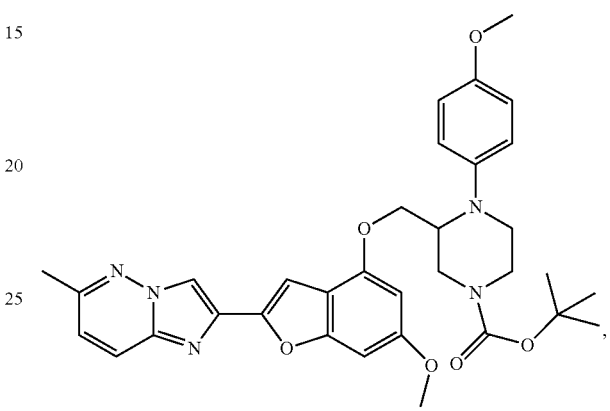

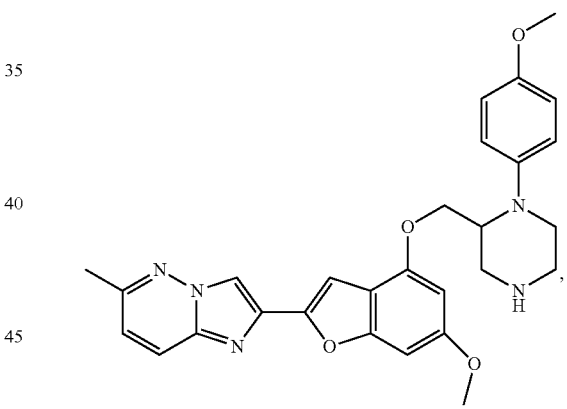

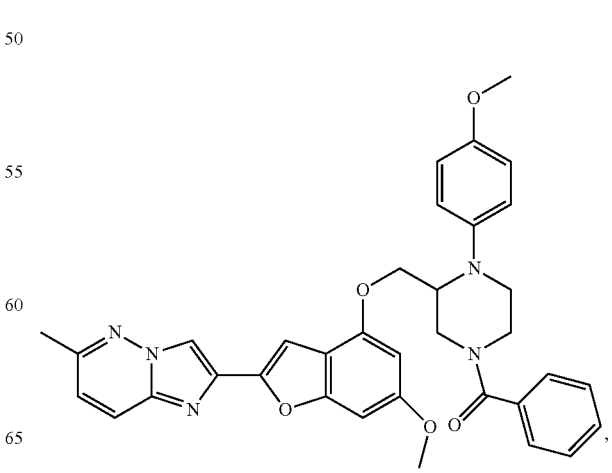

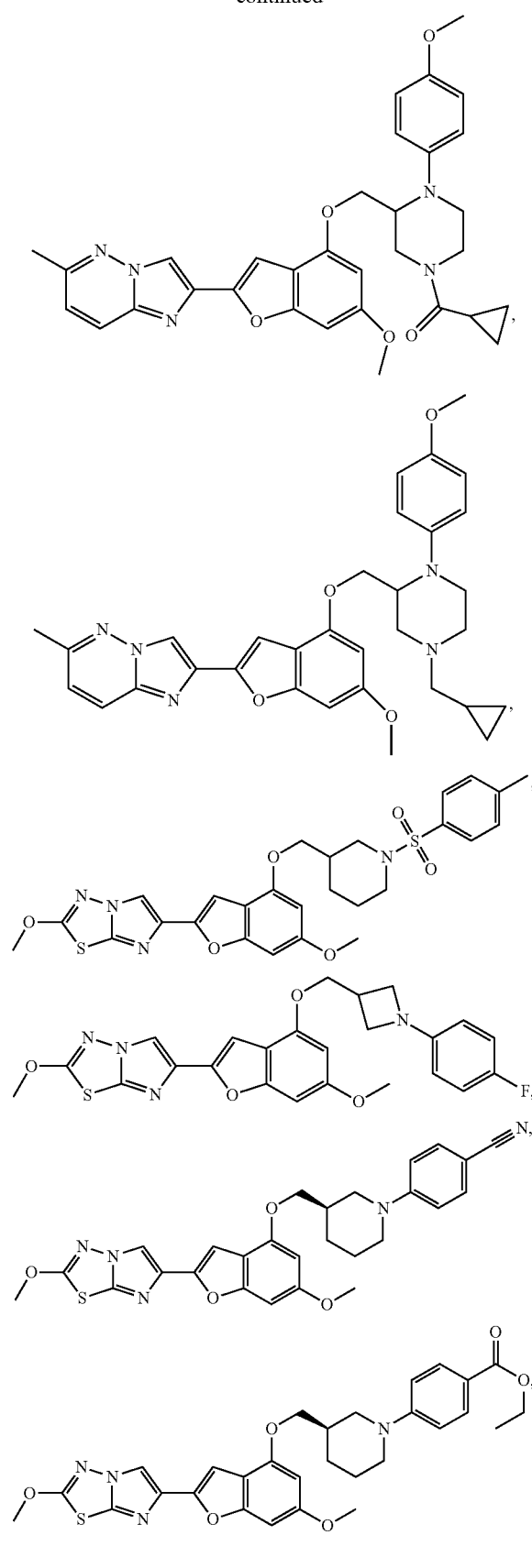
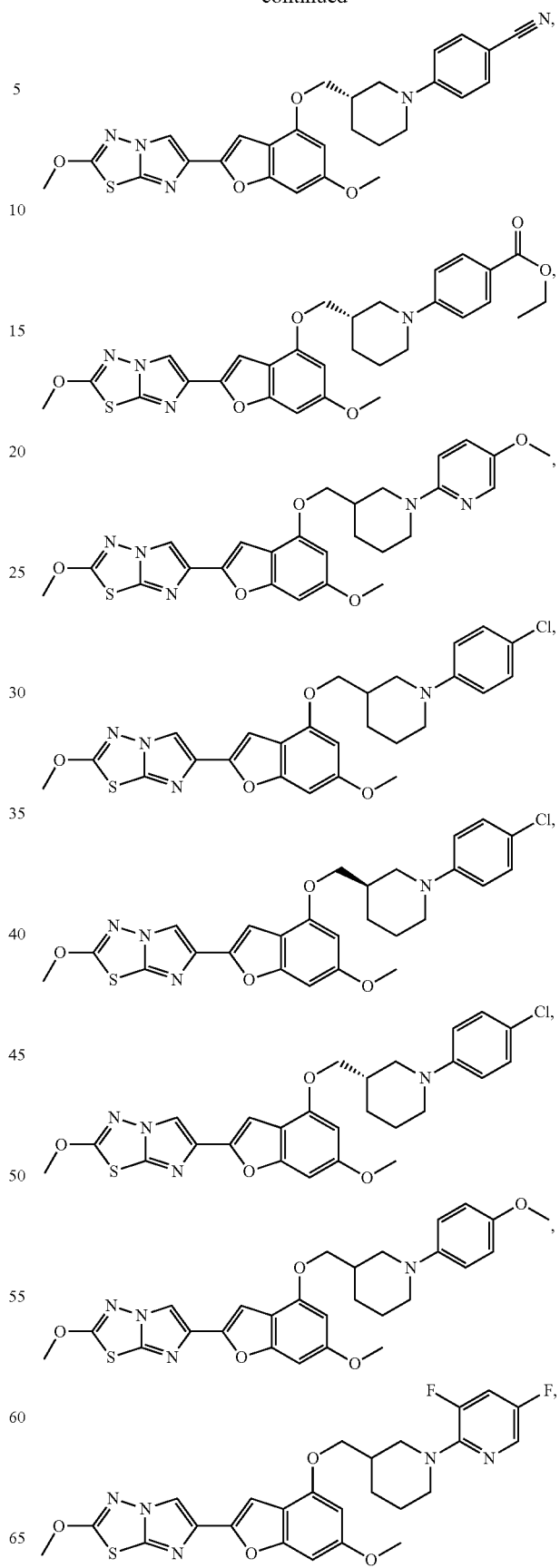

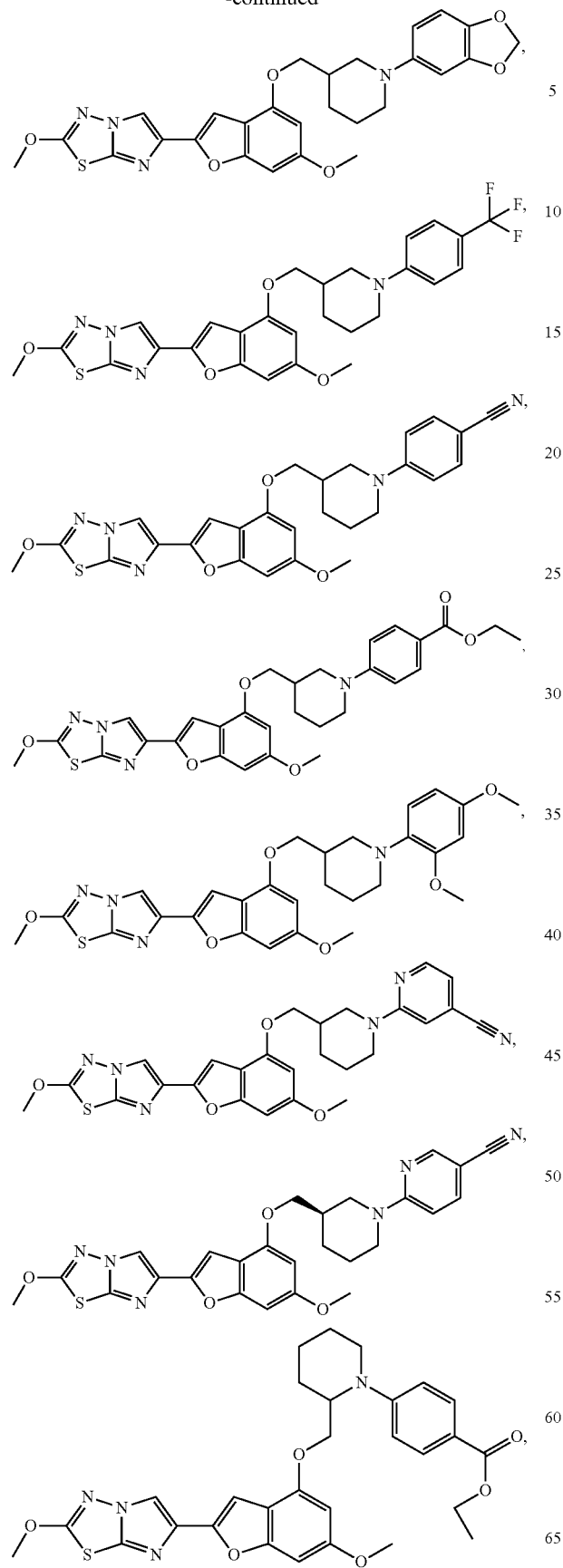
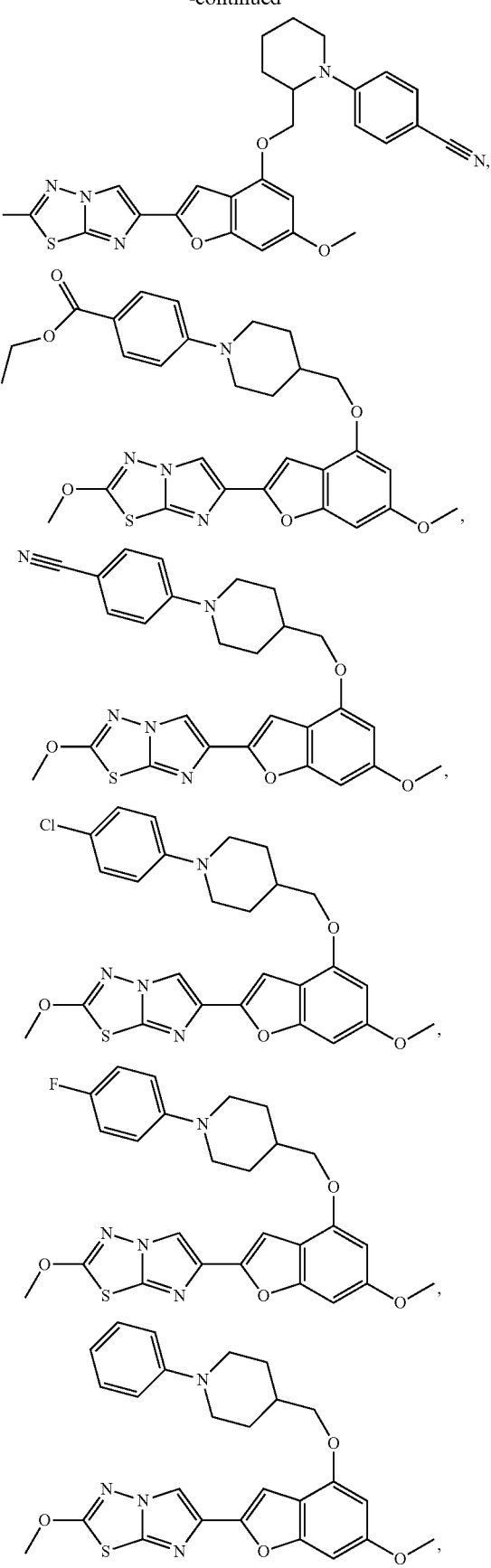

165
-continued
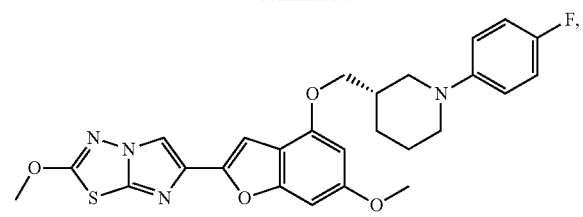
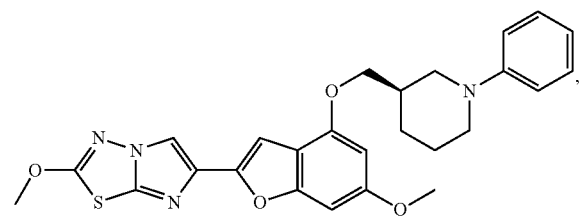
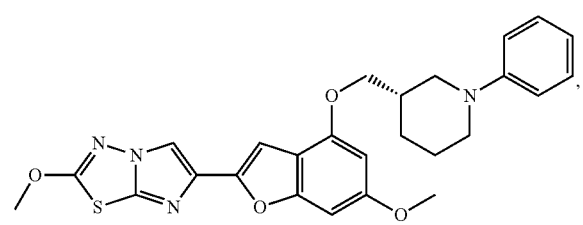
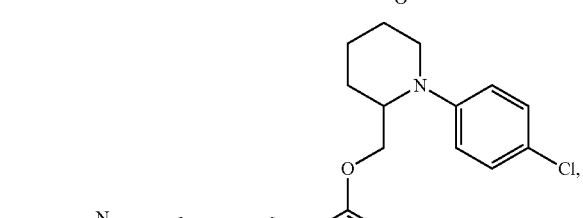
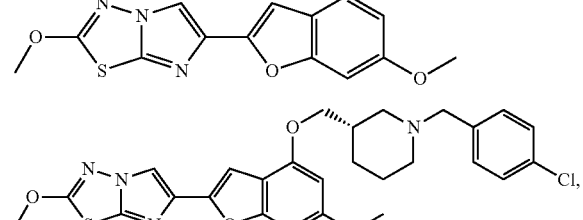
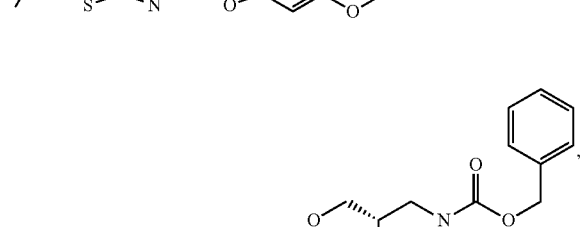
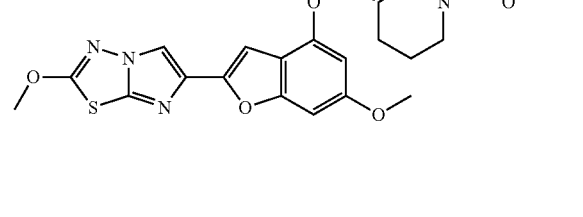
166
-continued
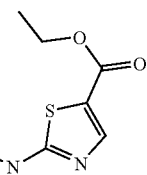
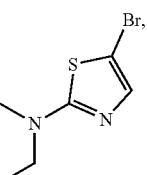
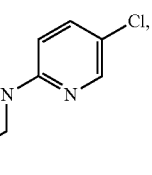
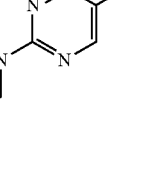
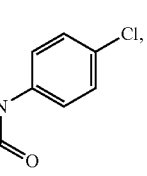
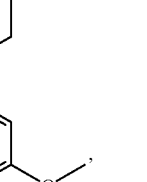

167
-continued

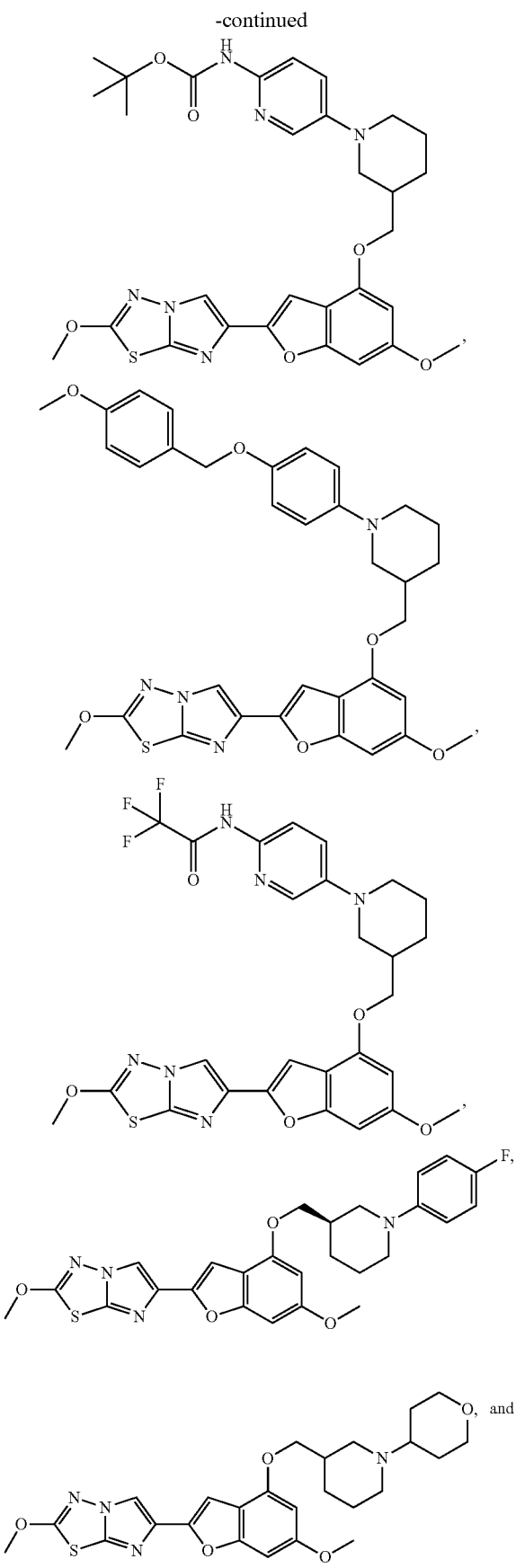

168
-continued

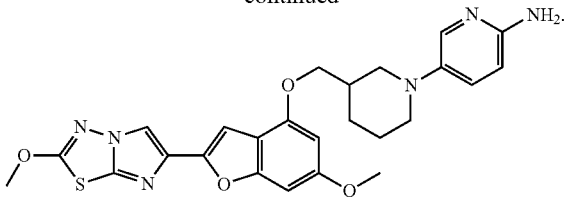

13. A pharmaceutical composition, which comprises a pharmaceutically acceptable carrier and a compound as defined in claim 1, or stereoisomers, tautomers, pharmaceutically acceptable salts, or solvates thereof, alone or in combination with another therapeutic agent.

14. A method for the treatment of a thromboembolic disorder or the primary or secondary prophylaxis of a thromboembolic disorder, which comprises the steps of administering to a patient in need thereof a therapeutically effective amount of a compound as defined in claim 1, or stereoisomers, tautomers, pharmaceutically acceptable salts, or solvates thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

15. A method of inhibiting or preventing platelet aggregation, which comprises the step of administering to a subject in need thereof a therapeutically effective amount of a protease activated receptor type 4 (PAR4) antagonist, as defined in claim 1.

16. A compound of Formula 1D:

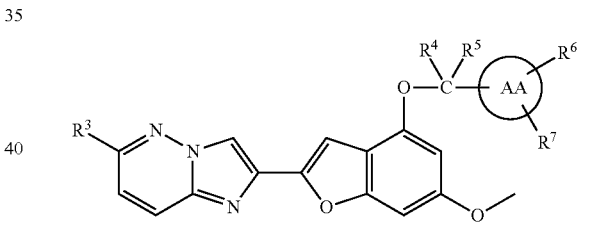

or a stereoisomer, tautomer, pharmaceutically acceptable salt, solvate or prodrug thereof, wherein:
$R^3$ is selected from the group consisting of methyl, ethyl, and chloro;
$R^4$ and $R^5$ are independently selected from H, and methyl;

is a piperidine, piperazine, morpholine, or pyrrolidine ring which may be unsubstituted or substituted at any open carbon atom valence with 0-1 $R^6$ and 0-4 $R^7$ substituents;
$R^6$ is selected from the group consisting of $C_6$-$C_{10}$ aryl, 5-10 membered heteroaryl, 4-8 membered saturated heterocyclic ring, or $C_3$-$C_8$ cycloalkyl ring, wherein each of said $C_6$-$C_{10}$ aryl, 5-10 membered heteroaryl, 4-8 membered saturated heterocyclic ring, or $C_3$-$C_8$ cycloalkyl ring, can be substituted with 0-4 $R^{7a}$ substituents;
$R^7$ is independently selected at each occurrence from the group consisting of halo, $C_1$-$C_4$ alkyl, $C_1$-$C_4$ alkoxy, halo $C_1$-$C_4$ alkyl, halo $C_1$-$C_4$ alkoxy, $C_1$-$C_4$ alkylthio, halo $C_1$-$C_4$ alkylthio, hydroxy, hydroxy $C_1$-$C_4$ alkyl, hydroxy $C_1$-$C_4$ alkoxy, ($C_1$-$C_6$ alkyl)carboxy-, carboxy, —C(O)Oalkyl, —C(O)NH$_2$, —C(O)NHalkyl, —C(O)N-dialkyl, —NH$_2$, (alkyl)amino-, (dialkyl)amino-, —NH-carboxy-$C_1$-$C_6$ alkyl, nitro, cyano, oxo, (haloaryl)alkyl-, $C_3$-$C_6$ cycloalkyl, —S(O)-alkyl, —S(O)-aryl, —S(O)-heteroaryl, —S(O$_2$)alkyl, —S(O$_2$)aryl, —S(O$_2$)heteroaryl, —S(O$_2$)NH$_2$, —S(O$_2$)NHalkyl, —S(O$_2$)N-dialkyl, or if two $R^7$ substituents are attached to the same carbon atom, they may be taken together with the carbon atom to which they are attached to form a $C_3$-$C_6$ cycloalkyl group or a 3-6 membered heterocyclic ring, or if two $R^7$ substituents are attached to adjacent carbon atoms, they may be taken together with the carbon atoms to which they are attached to form a $C_3$-$C_6$ cycloalkyl group or a 3-6 membered heterocyclic ring; and $R^{7a}$ is independently selected at each occurrence from the group consisting of halo, $C_1$-$C_4$ alkyl, $C_1$-$C_4$ alkoxy, halo $C_1$-$C_4$ alkyl, halo $C_1$-$C_4$ alkoxy, $C_1$-$C_4$ alkylthio, halo $C_1$-$C_4$ alkylthio, hydroxy, hydroxy $C_1$-$C_4$ alkyl, hydroxy $C_1$-$C_4$ alkoxy, ($C_1$-$C_6$ alkyl)carboxy-, carboxy, —C(O)Oalkyl, —C(O)NH$_2$, —C(O)NHalkyl, —C(O)N-dialkyl, —NH$_2$, (alkyl)amino-, (dialkyl)amino-, —NHC(O)O—$C_1$-$C_6$ alkyl, —NHC(O)-halo $C_1$-$C_6$ alkyl, nitro, cyano, oxo, $C_3$-$C_6$ cycloalkyl, —S(O)—alkyl, —S(O)-aryl, —S(O)-heteroaryl, —S(O$_2$)alkyl, —S(O$_2$)aryl, —S(O$_2$)heteroaryl, —S(O$_2$)NH$_2$, —S(O$_2$)NHalkyl, —S(O$_2$)N-dialkyl, aryl $C_1$-$C_4$ alkoxy, —C(O)aryl, —C(O)—$C_1$-$C_6$ alkyl, or if two $R^{7a}$ substituents are attached to the same carbon atom, they may be taken together with the carbon atom to which they are attached to form a $C_3$-$C_6$ cycloalkyl group or a 3-6 membered heterocyclic ring, or if two $R^{7a}$ substituents are attached to adjacent carbon atoms, they may be taken together with the carbon atoms to which they are attached to form a $C_3$-$C_6$ cycloalkyl group or a 3-6 membered heterocyclic ring.

17. A pharmaceutical composition, which comprises a pharmaceutically acceptable carrier and a compound as defined in claim 16, or stereoisomers, tautomers, pharmaceutically acceptable salts, or solvates thereof, alone or in combination with another therapeutic agent.

18. A method for the treatment of a thromboembolic disorder or the primary or secondary prophylaxis of a thromboembolic disorder, which comprises the steps of administering to a patient in need thereof a therapeutically effective amount of a compound as defined in claim 16, or stereoisomers, tautomers, pharmaceutically acceptable salts, or solvates thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

19. A method of inhibiting or preventing platelet aggregation, which comprises the step of administering to a subject in need thereof a therapeutically effective amount of a protease activated receptor type 4 (PAR4) antagonist, as defined in claim 16.

* * * * *